US012589170B2

(12) United States Patent
Manning et al.

(10) Patent No.: US 12,589,170 B2
(45) Date of Patent: Mar. 31, 2026

(54) DEVICES AND METHODS FOR RADIOPHARMACEUTICAL SYNTHESIS

(71) Applicant: VANDERBILT UNIVERSITY, Nashville, TN (US)

(72) Inventors: H. Charles Manning, Franklin, TN (US); Michael L. Nickels, Nashville, TN (US); Xin Zhang, Nashville, TN (US); Leon M. Bellan, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 1121 days.

(21) Appl. No.: 17/601,484

(22) PCT Filed: Apr. 7, 2020

(86) PCT No.: PCT/US2020/027019
§ 371 (c)(1),
(2) Date: Oct. 5, 2021

(87) PCT Pub. No.: WO2021/002913

PCT Pub. Date: Jan. 7, 2021

(65) Prior Publication Data
US 2022/0152230 A1 May 19, 2022

Related U.S. Application Data

(60) Provisional application No. 62/830,678, filed on Apr. 8, 2019.

(51) Int. Cl.
| | |
|---|---|
| *A61K 51/04* | (2006.01) |
| *A61K 51/08* | (2006.01) |
| *B01J 19/00* | (2006.01) |

(52) U.S. Cl.
CPC .......... *A61K 51/0446* (2013.01); *A61K 51/08* (2013.01); *B01J 19/0013* (2013.01);
(Continued)

(58) Field of Classification Search
CPC . A61K 51/0446; A61K 51/08; B01J 19/0013; B01J 19/0093; B01J 2219/00837;
(Continued)

(56) References Cited

U.S. PATENT DOCUMENTS

| | | | | |
|---|---|---|---|---|
| 2002/0079219 A1* | 6/2002 | Zhao | .......................... | B81B 1/00 204/601 |
| 2009/0275115 A1* | 11/2009 | Jury | ........................ | B01F 25/23 435/297.1 |

(Continued)

OTHER PUBLICATIONS

Ametamey, S. M.; Honer, M.; Schubiger, P. A. Chem. Rev. 2008, 108 (5), 1501-1516.
(Continued)

*Primary Examiner* — Jennifer Wecker
*Assistant Examiner* — Jonathan Bortoli
(74) *Attorney, Agent, or Firm* — troutman pepper locke; Tim Tingkang Xia, Esq.

(57) ABSTRACT

A device for synthesizing a radioisotope-labelled target tracer includes a microfluidic chip having an SCX module configured to concentrate and capture a radioisotope from a radioisotope solution and release the captured radioisotope therefrom, an SAX module configured to purify the released radioisotope from the SCX module, and an passive in-plane mixing/reaction module configured to mix the purified radioisotope with a target precursor and perform labelling reaction to synthesize the radioisotope-labelled target tracer therein. The device also includes a heating means positioned in relation to the microfluidic chip for heating the microfluidic chip during the labelling reaction; and a first valve fluidically coupled with the SCX and SAX modules and a
(Continued)

second valve fluidically coupled with the SAX module and the in-plane mixing/reaction module for operably controlling transit of various substances or mixtures among the SCX module, the SAX modules and the in-plane mixing/reaction module.

19 Claims, 24 Drawing Sheets

(52) U.S. Cl.
CPC .. *B01J 19/0093* (2013.01); *B01J 2219/00837* (2013.01); *B01J 2219/0086* (2013.01); *B01J 2219/00873* (2013.01); *B01J 2219/00889* (2013.01); *B01J 2219/00918* (2013.01); *B01J 2219/00952* (2013.01); *B01J 2219/00986* (2013.01)

(58) Field of Classification Search
CPC ...... B01J 2219/00853; B01J 2219/0086; B01J 2219/00873; B01J 2219/00889; B01J 2219/00918; B01J 2219/00952; B01J 2219/00986

See application file for complete search history.

(56) References Cited

U.S. PATENT DOCUMENTS

| | | | |
|---|---|---|---|
| 2012/0264932 A1* | 10/2012 | Van Dam | C07B 59/001 422/186 |
| 2012/0283490 A1 | 11/2012 | Gangadharmath et al. | |
| 2013/0225791 A1* | 8/2013 | Reichert | C07K 1/13 530/331 |
| 2014/0316130 A1* | 10/2014 | Brady | B01J 19/0093 422/68.1 |
| 2018/0033510 A1* | 2/2018 | Archibald | B01J 39/26 |
| 2019/0224677 A1* | 7/2019 | Smith | G01N 1/4077 |
| 2020/0179927 A1* | 6/2020 | Wang | B01J 19/0093 |

OTHER PUBLICATIONS

Fortt, R.; Gee, A. Future Med. Chem. 2013, 5 (3), 241-244.

Rensch, C.; Jackson, A.; Lindner, S.; Salvamoser, R.; Samper, V.; Riese, S.; Bartenstein, P.; Wangler, C.; Wangler, B. Molecules 2013, 18 (12), 7930-7956.

Audrain, H. Angew. Chemie Int. Ed. 2007, 46 (11), 1772-1775.

Elvira, K. S.; i Solvas, X. C.; Wootton, R. C. R.; DeMello, A. J. Nat. Chem. 2013, 5 (11), 905-915.

Philippe, C.; Pichler, V.; Hacker, M.; Mitterhauser, M.; Wadsak, W. 2018, 5997-6004.

Miller, P. W. J. Chem. Technol. Biotechnol. 2009, 84 (3), 309-315.

Chen, S.; Javed, M. R.; Kim, H.-K.; Lei, J.; Lazari, M.; Shah, G. J.; van Dam, R. M.; Keng, P.; Kim, C.-J. "CJ." Lab Chip 2014, 14 (5), 902-910.

Arima, V.; Pascali, G.; Lade, O.; Kretschmer, H. R.; Bernsdorf, I.; Hammond, V.; Watts, P.; De Leonardis, F.; Tarn, M. D.; Pamme, N.; Cvetkovic, B. Z.; Dittrich, P. S.; Vasovic, N.; Duane, R.; Jaksic, A.; Zacheo, A.; Zizzari, A.; Marra, L.; Perrone, E.; Salvadori, P. A.; Rinaldi, R. Lab Chip 2013, 13 (12), 2328.

Pascali, G.; Nannavecchia, G.; Pitzianti, S.; Salvadori, P. A. Nucl. Med. Biol. 2011, 38 (5), 637-644.

Bejot, R.; Elizarov, A. M.; Ball, E.; Zhang, J.; Miraghaie, R.; Kolb, H. C.; Gouverneur, V. J. Label. Compd. Radiopharm. 2011, 54 (3), 117-122.

Zeng, D.; Desai, A. V; Ranganathan, D.; Wheeler, T. D.; Kenis, P. J. A.; Reichert, D. E. Nucl. Med. Biol. 2013, 40 (1), 42-51.

Von Eyben, F. E.; Baumann, G. S.; Baum, R. P. Clin. Transl. Imaging 2018, 6 (2), 145-148.

Afshar-Oromieh, A.; Zechmann, C. M.; Malcher, A.; Eder, M.; Eisenhut, M.; Linhart, H. G.; Holland-Letz, T.; Hadaschik, B. A.; Giesel, F. L.; Debus, J.; Haberkorn, U. Eur. J. Nucl. Med. Mol. Imaging 2014, 41 (1), 11-20.

Afshar-Oromieh, A.; Haberkorn, U.; Eder, M.; Eisenhut, M.; Zechmann, C. M. Eur. J. Nucl. Med. Mol. Imaging 2012, 39 (6), 1085-1086.

Ahmadzadehfar, H.; Eppard, E.; Kurpig, S.; Fimmers, R.; Yordanova, A.; Schlenkhoff, C. D.; Gartner, F.; Rogenhofer, S.; Essler, M. Oncotarget 2016, 7 (11), 12477-12488.

Zhang, X.; Liu, F.; Knapp, K.-A.; Nickels, M. L.; Manning, H. C.; Bellan, L. M. Lab Chip 2018, 18, 1369-1377.

Mueller, D.; Breeman, W. A. P.; Klette, I.; Gottschaldt, M.; Odparlik, A.; Baehre, M.; Tworowska, I.; Schultz, M. K. Nat. Protoc. 2016, 11 (6), 1057-1066.

Mueller, D.; Klette, I.; Baum, R. P.; Gottschaldt, M.; Schultz, M. K.; Breeman, W. A. P. 2012.

Mueller, D.; Klette, I.; Baum, R. P.; Gottschaldt, M.; Schultz, M. K.; Breeman, W. A. P. Bioconjug. Chem. 2012, 23 (8), 1712-1717.

Korean Intellectual Property Office (ISR/KR), "International Search Report for PCT/US2020/027019", Korea, Jan. 27, 2021.

Zhang, Xin et al., "A simple microfluidic platform for rapid and efficient production of the radiotracer [18F] fallypride", Lab on a Chip, 2018, vol. 18, No. 9, pp. 1369-1377.

Alves, F., et al., "Cyclotron production of Ga-68 for human use from liquid targets: From theory to practice", AIP Conference Proceedings, 2017, vol. 1845, No. 1.

Ianovska, Margaryta, "Microfluidic tools for multidimensional liquid chromatography", Doctoral dissertation, University of Groningen, 2018, pp. 39-84.

Waldbaur, Ansgar et al., "Microfluidics on liquid handling stations (μF-on-LHS): an industry compatible chip interface between microfluidics and automated liquid handling stations", Lab on a Chip, 2013, vol. 13, No. 12, pp. 2337-2343.

* cited by examiner

FIG. 9

DEVICES AND METHODS FOR RADIOPHARMACEUTICAL SYNTHESIS

CROSS-REFERENCE TO RELATED PATENT APPLICATION

This application claims priority to and the benefit of U.S. Provisional Patent Application Ser. No. 62/830,678, filed Apr. 8, 2019, which is incorporated herein by reference in its entirety.

FIELD OF THE INVENTION

The invention relates generally to radiopharmaceutical synthesis, and more particularly to devices and methods for high-yielding radiosynthesis of $^{68}$Ga-PSMA towards on-demand production of personalized PET imaging.

BACKGROUND INFORMATION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Positron emission tomography (PET) is a powerful diagnostic and imaging technique that has found widespread use for applications such as disease diagnosis, and drug discovery. Currently, considerable efforts have been devoted to developing novel compounds that are labeled with short-lived radioisotopes, which serve as a biomarker to enable detailed mapping of certain biological processes. To date, though more than 1500 PET imaging probes have been discovered in research settings, only one tracer, [$^{18}$F]fluorodeoxyglucose (FDG), is routinely produced for more than 90% use of clinical PET scans. While PET exhibits many desirable characteristics, the availability of PET technology is severely limited by high-cost, labor-intensive and time-consuming processes associated with the production of sensitive radiotracers. Therefore, there has been a push in the field of radiochemistry to decentralize radiopharmaceuticals' synthesis and enable cost effective production of PET tracers on demand.

Recently, the use of microfluidic reactors in preparation of PET probes has been regarded as a viable strategy to expand the availability of PET scans. Compared to macroscale automated synthesis modules, microfluidic reactors exhibit many favorable advantages such as small volume consumption, rapid reaction kinetics, and small footprints, all of which makes this technology extremely attractive for synthesis of time-sensitive PET imaging agents. Previous efforts have described a number of microfluidic systems such as capillary-based microfluidic synthesis platforms and lab-on-a-chip devices. In general, these devices either illustrate improved performance on one particular step (i.e., radioisotope concentration or incorporation reaction) or demonstrate remarkable radiochemical yield for synthesis of diverse PET radiotracers. Despite reported success, the majority of these microfluidic devices unfavorably involves the addition of routine treatments such as pre-concentration of isotopes or subsequent product purification, which leads to unwanted loss of radioactivity. In addition, most of these isolated products are not suitable to be directly administrated to patient. Consequently, it is of fundamental interest to explore advanced microfluidic platforms such that PET imaging probes isolated off the chip exhibit ultrahigh radiochemical and chemical purity, making them meet rigorous quality control (QC) testing.

Therefore, a heretofore unaddressed need exists in the art to address the aforementioned deficiencies and inadequacies.

SUMMARY OF THE INVENTION

To fulfill abovementioned requirements, one of the objectives of this invention is to provide a cost effective microfluidic platform that enables synthesis of radiopharmaceuticals to a dose-on-demand level that isolated products after formulation are qualified for direct injection.

In one aspect, the invention relates to a device for synthesizing a radioisotope-labelled target tracer.

In one embodiment, the device includes a microfluidic chip formed of a patterned or etched layer on a substrate comprising a strong cation exchange (SCX) module, a strong anion exchange (SAX) module, and an passive in-plane mixing and reaction module. The SCX module is configured to cationically concentrate and capture a radio-isotope from a radioisotope solution delivered from a radio-isotope generator, and release the captured radioisotope therefrom. The SAX module in fluidic communication with the SCX module is configured to anionically purify the released radioisotope from the SCX module. The passive in-plane mixing and reaction module in fluidic communication with the SAX module is configured to mix the purified radioisotope with a target precursor, and perform labelling reaction to synthesize the radioisotope-labelled target tracer therein.

The device also includes a heating means positioned in relation to the microfluidic chip for heating the microfluidic chip during the labelling reaction; and a first valve fluidically coupled with the SCX module and the SAX module and a second valve fluidically coupled with the SAX module and the passive in-plane mixing and reaction module for operably controlling transit of various substances or mixtures among the SCX module, the SAX module, and the passive in-plane mixing and reaction module.

In one embodiment, the device further includes one or more pumps fluidically coupled with at least one of the first valves and the second valves for operably controlling flow of the various substances or mixtures.

In one embodiment, each of the SCX module and the SAX module comprises an inlet, an outlet, a microchannel formed between the inlet and the outlet, and a trapping mechanism formed in the microchannel proximate to the outlet of the microchannel.

In one embodiment, inner walls of the microchannel of at least one of the SCX module and the SAX module are coated with an inert layer.

In one embodiment, the microchannel has a length, a width, and a height, wherein the height is a micro-size. In one embodiment, the length is greater than the width, or the length is equal to or less than the width.

In one embodiment, the microchannel of at least one of the SCX module and the SAX module comprises two or more sub-chambers in parallel.

In one embodiment, the microchannel of at least one of the SCX module and the SAX module comprises a single chamber with two or more isolated sub-inlets and sub-outlets to yield enhanced packing uniformity.

In one embodiment, the trapping mechanism comprises at least one row of pillars with predefined gaps.

In one embodiment, each of the SCX module and the SAX module has columns operably formed of microparticles with desired functionality in the microchannel by the trapping mechanism, for radioactivity concentration or purification, wherein the microparticles are suspended in a solution loaded into the microchannel. In one embodiment, the microparticles in the microchannel of the SCX module comprise SCX resin, and the microparticles in the microchannel of the SAX module comprise SAX resin.

In one embodiment, the passive in-plane mixing and reaction module comprises a flow focusing means, a mixing channel and a reaction chamber, wherein the flow focusing means is formed at the entrance of the mixing channel and configured to focus flows of the purified radioisotope and the target precursor onto the mixing channel in which the purified radioisotope and the target precursor are mixed therethrough to form a mixture that is in turn loaded into the reaction chamber for labelling reaction therein.

In one embodiment, the flow focusing means comprises at least one target precursor inlet and at least two radioisotope inlets configured such that the purified radioisotope injected from the at least two radioisotope inlets into the focusing means is in two radioisotope flow directions facing one another, and the target precursor injected from at least one target precursor inlet into the focusing means is in a target precursor flow direction that has an angle relative to the radioisotope flow directions, wherein the angle is greater than zero degree. In one embodiment, the mixing channel is a zigzag mixing microchannel and/or has a plurality of obstructions formed therein.

In one embodiment, the heating means comprises a hot plate placed under the substrate.

In one embodiment, the heating means comprises an on-chip resistive heater and an on-chip resistive temperature detector (RTD) to enable closed-loop control of a reaction temperature in a predefined range. In one embodiment, the on-chip resistive heater comprises metal electrodes patterned on the substrate, and the on-chip RTD comprises metal electrodes patterned on the substrate proximate to the metal traces of the on-chip resistive heater. In one embodiment, the metal electrodes of the on-chip resistive heater and the metal electrodes of the on-chip RTD are formed of a same metal or different metals. In one embodiment, the heating means further comprises a protective layer formed over the metallic electrodes of the on-chip resistive heater and the on-chip RTD.

In one embodiment, the device also includes a microcontroller configured to read a temperature measured by the on-chip RTD and control a solid state relay (SSR) to rapidly connect or disconnect the on-chip resistive heater from a power supply by using a PID (proportional, integral, differential) library.

In one embodiment, the microcontroller is configured further to control operations of the first and second valves, and the one or more pumps so as to control the transit of various substances or mixtures among the SCX module, the SAX module, and the passive in-plane mixing and reaction module.

In one embodiment, the microcontroller is configured such that the operations of the first and second valves, the one or more pumps, and/or the heating means are controllable via one or more user interfaces in a computer or a mobile device in a wired or wireless communication.

In one embodiment, the radioisotope comprises $^{68}$Ga or $^{177}$Lu, and the target precursor comprises prostate-specific membrane antigen (PSMA). The radioisotope-labelled target tracer is $^{68}$Ga-labelled PSMA or $^{177}$Lu-labelled PSMA.

In another aspect, the invention relates to a method of synthesizing a radioisotope-labelled target tracer using the device above.

In one embodiment, the method comprises introducing a radioisotope solution generated from a radioisotope generator into the SCX module at a first predetermined loading rate followed by injecting a first amount of air into the SCX module to push all liquid through the SCX module, thereby concentrating and capturing the radioisotope inside the SCX module; injecting an eluting solution into the SCX module at a second predetermined loading rate to release the concentrated and captured the radioisotope from the SCX module, and simultaneously directing the released radioisotope into the SAX module, followed by injecting a second amount of air into the SCX module to enable all solution sequentially through the SCX module and SAX module; injecting DI water into the SAX module at a third predetermined loading rate to release trapped radioisotope off the SAX module; mixing the released radioisotope with a target precursor solution in the mixing channel to form a mixture therein and loading the mixture into the reaction chamber; and heating the microfluidic chip at a predetermined temperature for a period of time to perform labelling reaction in the reaction chamber so as to synthesize the radioisotope-labelled target tracer therein.

In one embodiment, the eluting solution is a mixture of 5M NaCl and 5.5M HCl.

In one embodiment, the method further comprises, prior the step of mixing the released radioisotope with the target precursor in the mixing channel, focusing flows of the purified radioisotope and the target precursor via the flow focusing means onto the mixing channel.

In one embodiment, the precursor solution contain PSMA-11 ligand dissolved in sodium acetate buffer.

In one embodiment, the radioisotope comprises $^{68}$Ga or $^{177}$Lu, and the radioisotope-labelled target tracer is $^{68}$Ga-labelled PSMA or $^{177}$Lu-labelled PSMA.

In a further aspect, the invention relates to an automated system for production of customizable, dose-on-demand radiotracers.

In one embodiment, the automated system includes a stage; a plurality of microfluidic chips, each microfluidic chip configured to operably produce a customized radiotracer, wherein in operation, one of the plurality of microfluidic chips is selected based on the customized radiotracer to be produced and placed on the stage; and an interface array fluidically coupled to the selected microfluidic chip and configured to selectively deliver at least one reagent and at least one radioisotope based on the customized radiotracer into the selected microfluidic chip, and collect the customized radiotracer produced from the selected microfluidic chip.

In one embodiment, the automated system further comprises a microcontroller unit (MCU) configured to control selection of the plurality of microfluidic chips, delivery of the at least one reagent and the at least one radioisotope.

In one embodiment, the MCU is configured to further control operations of valves, pumps, and/or liquid handling systems. In one embodiment, the valves comprises off-chip mechanical valves, and/or on-chip rotary planar valves, the pumps comprise syringe pumps, and/or microcontroller-driven peristaltic pumps including on-chip rotary planar peristaltic micropumps.

In one embodiment, the MUC is configured to further control and/or schedule dose production requests via an online web or smartphone app interface.

In one embodiment, the automated system further comprises a plurality of sensors for process monitoring.

In one embodiment, the automated system further comprises means for washes and gas purges between batches to ensure cleanliness of fluid paths and prevent cross-contamination.

In one embodiment, the automated system further comprises a robotic handling system configured to operably dispense specified dosages into multiple separate containers.

In one embodiment, the robotic handling system is further configured to operably move unused and used microfluidic chips in corresponding magazines.

In one embodiment, the automated system further comprises photomultipliers interfaced to the process controller at multiple desired locations to perform at least one of monitoring an amount of radioactivity captured in the on-chip concentration column; ensuring that purge steps adequately eliminate residual isotope in the tubing; verifying that used microfluidic chips have undergone an adequate cool-down time period and no longer exhibit dangerous levels of radioactivity before they are ejected into a disposal bin; and as part of an interlock system prohibiting users from opening shielded boxes unless radiation levels are safe.

In one embodiment, the automated system further comprises electrical contacts to on-chip thermal control using pogo-pins.

In one embodiment, the automated system further comprises an array of needles configured such that when in use the array of needles is pressed against a microfluidic chip, the needles form fluidic connections with ports (inlets and outlets) on the microfluidic chip.

In one embodiment, the automated system further comprises in-line pressure and flow sensors configured to operably monitor any batch-to-batch variation, and operably check to ensure backpressure is not too high (indicating clogging) or too low (indicating membrane damage).

In one embodiment, the automated system further comprises in-line sterile filters placed in a fluidic path between the microfluidic chip outlet and the robotic system for dispensing into sterile vials.

In one embodiment, the automated system is capable of producing multiple, unique doses of ready-to-use radiotracers that are reliably pass all FDA-acceptable release criteria.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

(FIG. 3A) concentration of generator-obtained $^{68}$Ga$^{3+}$ using an on-chip SCX column, (FIG. 3B) $^{68}$Ga$^{3+}$ elution from the SCX, followed by trapping on the SAX in the form of $[^{68}$GaCl$_4]^-$, (FIG. 3C) release $^{68}$Ga$^{3+}$ with water, followed by mixing with PSMA precursor to accomplish the formation of $^{68}$Ga-PSMA, according to one embodiment of the invention.

FIG. 9 shows synthesis process for the production of $[^{18}$F]fallypride, according to one embodiment of the invention.

(FIG. 11A) concentrate [$^{18}$F]fluoride using anion-exchange column, (FIG. 11B) release trapped [18F]fluoride off the column and transfer into reaction cavity, (FIG. 11C) evaporate to achieve an anhydrous environment by heating and N2 drying, (FIG. 11D) [$^{18}$F]fallypride fluorination, (FIG. 11E) isolate undesired products using purification column, and (FIG. 11F) collect purified [$^{18}$F]fallypride off chip.

FIG. 18A is an image of the on-chip heater and RTD. FIG. 18B shows a microcontroller and associated hardware (MAX31865 and SSR) for providing PID-based closed-loop control of local temperature. FIGS. 18C and 18D are respectively IR thermal and regular optical images of the on-chip heater and RTD in operation.

FIG. 19A is a packed bed geometry as disclosed in EXAMPLE 1, with frit at the bottom. FIG. 19B is an alternative embodiment that has an equivalent volume as that of FIG. 19A, but shorter and wider to reduce fluidic resistance. FIG. 19C shows a architecture having three smaller chambers in parallel, leading to reduced fluidic resistance but more uniformity in each chamber. FIG. 19D shows a single chamber with three isolated inlets and outlets to yield enhanced packing uniformity and avoid unequal pressure between chambers. Arrows indicate differences between architectures of FIGS. 19C and 19D.

FIG. 22A is a photograph of two staggered rows of 4 PEEK needles each (1/16″ outer diameter). FIG. 22B shows using the needle array to interface to microfluidic channels. Four different colors of food coloring (yellow, green, red, blue) are introduced into a series of extended microfluidic loops using one row of the needle array (interfacing to laser-drilled ports, not visible), and begin to exit the device via the other row of the needle array.

DETAILED DESCRIPTION OF THE INVENTION

Figure 1:
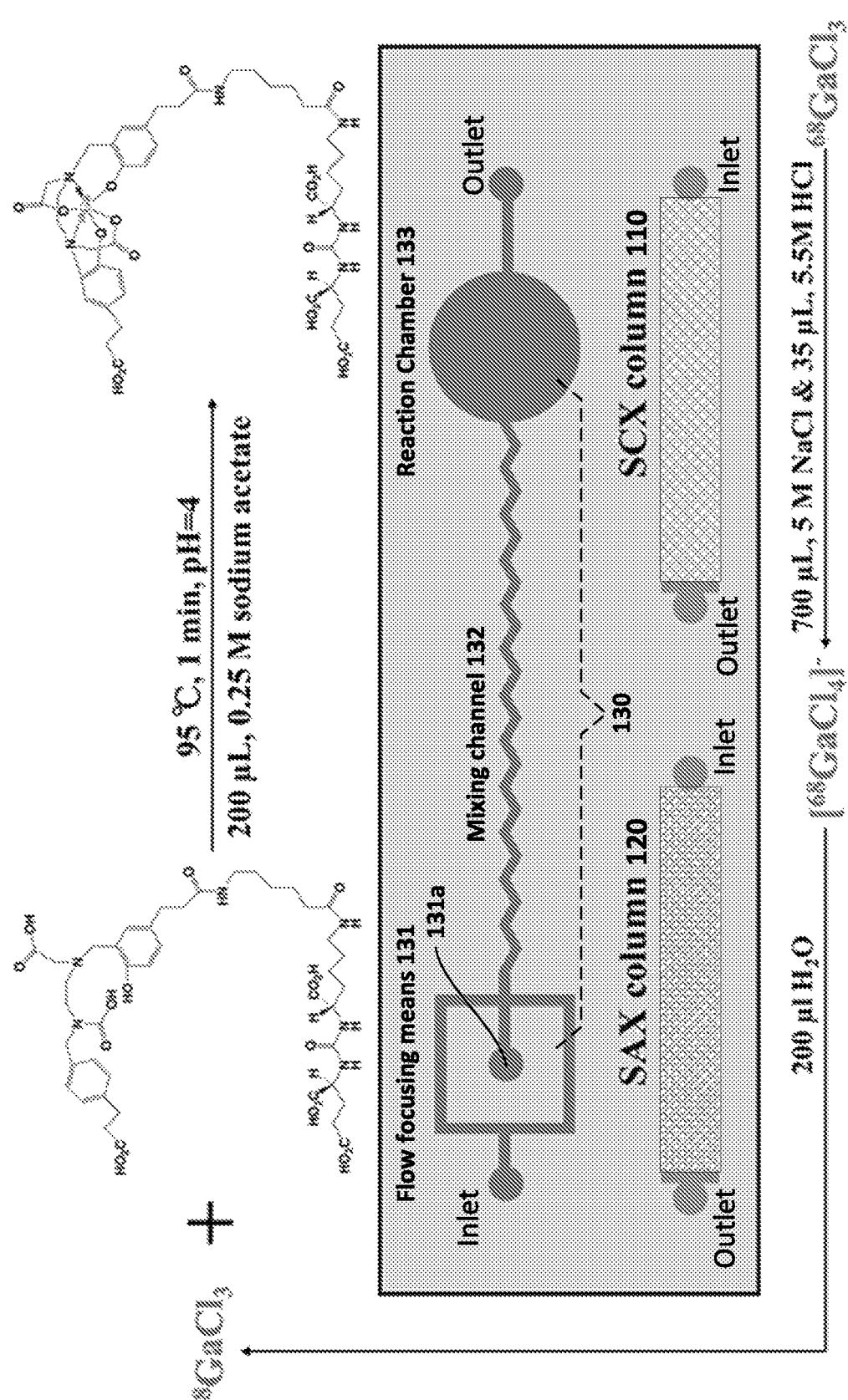
FIG. 1 shows a schematic representation of a microfluidic chip designed for the synthesis of $^{68}$Ga-PSMA-11, including an SCX column, SAX column, passive mixing module and reactor for the labelling reaction according to one embodiment of the invention.

The invention will now be described more fully hereinafter with reference to the accompanying drawings, in which exemplary embodiments of the invention are shown. The invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used in this invention, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Positron Emission Tomography (PET) is a non-invasive imaging modality that allows for the in vivo quantification of biochemical processes using radiolabeled compounds or "tracers". These tracers typically undergo synthesis using an automated synthesis module (ASM) that requires an infrastructural link to a cyclotron, a lead-shielded fume hood known as a hot cell, and a large amount of precious laboratory real estate. These requirements have created a bottleneck in PET tracer development, leading a search for a new type of system that can decrease system costs while increasing radiochemical and chemical purities, specific activities, and/or radiochemical yields of the final tracer.

Microfluidic systems have the potential to enable a dose-on-demand (DOD) system of PET tracer distribution, allowing for individual tracer production at the demand of the PET imaging facility. This has the potential to decrease the cost of the tracer and enable the increase of specialized PET tracer production. The first human use of a radiotracer produced by a microfluidic batch-reactor has been reported recently. However, while this recent report did use a microfluidic chip as microreactor for the fluorination step, the fluoride concentration subsystem utilized a commercial ion-exchange cartridge (off-chip), and final purification step was accomplished via conventional HPLC (also off-chip), thereby missing the opportunity of integrating all steps of the production within a single, compact microfluidic chip. Although there has been exciting progress employing microfluidic technology for PET tracer synthesis, most efforts focus primarily on the investigation of a single step in the process (mostly on-chip radiosynthesis), leaving other essential steps to be performed off-chip.

To address the aforementioned deficiencies and inadequacies, one aspect of this invention is to integrate all the essential modules onto a single microfluidic chip, enabling the synthesis of PET tracer from the very beginning (radioactive reagent mixture) to the final stage (radiotracer ready for injection). The goals of this highly-integrated microfluidic platform would include the following: (1) The entire production process should be fast and efficient, minimizing the decay of radionuclide and consuming minimal reagents. (2) The shield needed to protect users from radiation on the microfluidic chip should be simply achieved by using lead bricks, avoiding the need for large, bulky hot cells. (3) The microfluidic chip should be low-cost and disposable, and a fresh chip should be used for each individual radiotracer production run. (4) The microfluidic chip should be able to produce purified products in sufficient doses, ready for animal or human imaging. (5) The technique to produce the on-chip columns should be flexible enough to enable the production of various PET radiotracers by simply switching the materials packed inside the microchannel.

To achieve these goals and facilitate the development of novel PET tracers for both research and clinical applications, a simple microfluidic system is disclosed, which integrates several modules on a single chip to accomplish all principal steps for radiotracer production.

Specifically, in one aspect of the invention discloses a RAPID chip for producing $^{68}$Ga-PSMA on-demand for personalized PET imaging. The reproducibility and ease-of-use can be improved by incorporating closed loop, on-chip thermal control.

Another aspect of the invention discloses a RAPID chip for high throughput radiofluorination of radiotracers with various fluidic architectures, which improve the throughput of the microfluidic device for $^{18}$F radiochemistries, and enable clinically relevant radiotracer production of at least 50 mCi of ready-to-use $^{18}$F-fallypride and $^{18}$F-FSPG in under 30 minutes.

A further aspect of the invention discloses a system/platform and method of automation of the RAPID chip operations for customizable, dose-on-demand PET radiopharmaceutical production: In certain embodiments, the automated platform includes, but is not limited to, robotic handling of RAPID chips from magazines, automated fluidic control, monitoring of residual radioactivity in used chips to ensure adequate "cool-down" time, time-stamping of dosages produced to provide real-time knowledge of activity and expiration times, and completely autonomous functionality with a WiFi interface for scheduling and maintenance. The automated platform around the RAPID chip allows a clinician to remotely schedule automated production yielding ready-to-inject PET tracers as needed.

In one aspect, the invention relates to a device for synthesizing a radioisotope-labelled target tracer.

In one embodiment, the device includes a microfluidic chip formed of a patterned or etched layer on a substrate comprising a strong cation exchange (SCX) module, a strong anion exchange (SAX) module, and an passive in-plane mixing and reaction module. The SCX module is configured to cationically concentrate and capture a radioisotope from a radioisotope solution delivered from a radioisotope generator, and release the captured radioisotope therefrom. The SAX module in fluidic communication with the SCX module is configured to anionically purify the released radioisotope from the SCX module. The passive in-plane mixing and reaction module in fluidic communication with the SAX module is configured to mix the purified radioisotope with a target precursor, and perform labelling reaction to synthesize the radioisotope-labelled target tracer therein.

The device also includes a heating means positioned in relation to the microfluidic chip for heating the microfluidic chip during the labelling reaction; and a first valve fluidically coupled with the SCX module and the SAX module and a second valve fluidically coupled with the SAX module and the passive in-plane mixing and reaction module for operably controlling transit of various substances or mixtures among the SCX module, the SAX module, and the passive in-plane mixing and reaction module.

In one embodiment, the device further includes one or more pumps fluidically coupled with at least one of the first valves and the second valves for operably controlling flow of the various substances or mixtures.

In one embodiment, each of the SCX module and the SAX module comprises an inlet, an outlet, a microchannel formed between the inlet and the outlet, and a trapping mechanism formed in the microchannel proximate to the outlet of the microchannel.

In one embodiment, inner walls of the microchannel of at least one of the SCX module and the SAX module are coated with an inert layer.

In one embodiment, the microchannel has a length, a width, and a height, wherein the height is a micro-size. In one embodiment, the length is greater than the width, or the length is equal to or less than the width.

In one embodiment, the microchannel of at least one of the SCX module and the SAX module comprises two or more sub-chambers in parallel.

In one embodiment, the microchannel of at least one of the SCX module and the SAX module comprises a single chamber with two or more isolated sub-inlets and sub-outlets to yield enhanced packing uniformity.

In one embodiment, the trapping mechanism comprises at least one row of pillars with predefined gaps.

In one embodiment, each of the SCX module and the SAX module has columns operably formed of microparticles with desired functionality in the microchannel by the trapping mechanism, for radioactivity concentration or purification, wherein the microparticles are suspended in a solution loaded into the microchannel. In one embodiment, the microparticles in the microchannel of the SCX module comprise SCX resin, and the microparticles in the microchannel of the SAX module comprise SAX resin.

In one embodiment, the passive in-plane mixing and reaction module comprises a flow focusing means, a mixing channel and a reaction chamber, wherein the flow focusing means is formed at the entrance of the mixing channel and configured to focus flows of the purified radioisotope and the target precursor onto the mixing channel in which the purified radioisotope and the target precursor are mixed therethrough to form a mixture that is in turn loaded into the reaction chamber for labelling reaction therein.

In one embodiment, the flow focusing means comprises at least one target precursor inlet and at least two radioisotope inlets configured such that the purified radioisotope injected from the at least two radioisotope inlets into the focusing means is in two radioisotope flow directions facing one another, and the target precursor injected from at least one target precursor inlet into the focusing means is in a target precursor flow direction that has an angle relative to the radioisotope flow directions, wherein the angle is greater than zero degree. In one embodiment, the mixing channel is a zigzag mixing microchannel and/or has a plurality of obstructions formed therein.

In one embodiment, the heating means comprises a hot plate placed under the substrate.

In one embodiment, the heating means comprises an on-chip resistive heater and an on-chip resistive temperature detector (RTD) to enable closed-loop control of a reaction temperature in a predefined range. In one embodiment, the on-chip resistive heater comprises metal electrodes patterned on the substrate, and the on-chip RTD comprises metal electrodes patterned on the substrate proximate to the metal traces of the on-chip resistive heater. In one embodiment, the metal electrodes of the on-chip resistive heater and the metal electrodes of the on-chip RTD are formed of a same metal or different metals. In one embodiment, the heating means further comprises a protective layer formed over the metallic electrodes of the on-chip resistive heater and the on-chip RTD.

In one embodiment, the device also includes a microcontroller configured to read a temperature measured by the on-chip RTD and control a solid state relay (SSR) to rapidly connect or disconnect the on-chip resistive heater from a power supply by using a PID (proportional, integral, differential) library.

In one embodiment, the microcontroller is configured further to control operations of the first and second valves, and the one or more pumps so as to control the transit of various substances or mixtures among the SCX module, the SAX module, and the passive in-plane mixing and reaction module.

In one embodiment, the microcontroller is configured such that the operations of the first and second valves, the one or more pumps, and/or the heating means are controllable via one or more user interfaces in a computer or a mobile device in a wired or wireless communication.

In one embodiment, the radioisotope comprises $^{68}$Ga or $^{177}$Lu, and the target precursor comprises prostate-specific membrane antigen (PSMA). The radioisotope-labelled target tracer is $^{68}$Ga-labelled PSMA or $^{177}$Lu-labelled PSMA.

In another aspect, the invention relates to a method of synthesizing a radioisotope-labelled target tracer using the device above.

In one embodiment, the method comprises introducing a radioisotope solution generated from a radioisotope generator into the SCX module at a first predetermined loading rate followed by injecting a first amount of air into the SCX module to push all liquid through the SCX module, thereby concentrating and capturing the radioisotope inside the SCX module; injecting an eluting solution into the SCX module at a second predetermined loading rate to release the concentrated and captured the radioisotope from the SCX module, and simultaneously directing the released radioisotope into the SAX module, followed by injecting a second amount of air into the SCX module to enable all solution sequentially through the SCX module and SAX module; injecting DI water into the SAX module at a third predetermined loading rate to release trapped radioisotope off the SAX module; mixing the released radioisotope with a target precursor solution in the mixing channel to form a mixture therein and loading the mixture into the reaction chamber; and heating the microfluidic chip at a predetermined temperature for a period of time to perform labelling reaction in the reaction chamber so as to synthesize the radioisotope-labelled target tracer therein.

In one embodiment, the eluting solution is a mixture of 5M NaCl and 5.5M HCl.

In one embodiment, the method further comprises, prior the step of mixing the released radioisotope with the target precursor in the mixing channel, focusing flows of the purified radioisotope and the target precursor via the flow focusing means onto the mixing channel.

In one embodiment, the precursor solution contain PSMA-11 ligand dissolved in sodium acetate buffer.

In one embodiment, the radioisotope comprises $^{68}$Ga or $^{177}$Lu, and the radioisotope-labelled target tracer is $^{68}$Ga-labelled PSMA or $^{177}$Lu-labelled PSMA.

In a further aspect, the invention relates to an automated system for production of customizable, dose-on-demand radiotracers.

In one embodiment, the automated system includes a stage; a plurality of microfluidic chips, each microfluidic chip configured to operably produce a customized radiotracer, wherein in operation, one of the plurality of microfluidic chips is selected based on the customized radiotracer to be produced and placed on the stage; and an interface array fluidically coupled to the selected microfluidic chip and configured to selectively deliver at least one reagent and at least one radioisotope based on the customized radiotracer into the selected microfluidic chip, and collect the customized radiotracer produced from the selected microfluidic chip.

In one embodiment, the automated system further comprises a microcontroller unit (MCU) configured to control selection of the plurality of microfluidic chips, delivery of the at least one reagent and the at least one radioisotope.

In one embodiment, the MCU is configured to further control operations of valves, pumps, and/or liquid handling systems. In one embodiment, the valves comprises off-chip mechanical valves, and/or on-chip rotary planar valves, the pumps comprise syringe pumps, and/or microcontroller-driven peristaltic pumps including on-chip rotary planar peristaltic micropumps.

In one embodiment, the MUC is configured to further control and/or schedule dose production requests via an online web or smartphone app interface.

In one embodiment, the automated system further comprises a plurality of sensors for process monitoring.

In one embodiment, the automated system further comprises means for washes and gas purges between batches to ensure cleanliness of fluid paths and prevent cross-contamination.

In one embodiment, the automated system further comprises a robotic handling system configured to operably dispense specified dosages into multiple separate containers.

In one embodiment, the robotic handling system is further configured to operably move unused and used microfluidic chips in corresponding magazines.

In one embodiment, the automated system further comprises photomultipliers interfaced to the process controller at multiple desired locations to perform at least one of monitoring an amount of radioactivity captured in the on-chip concentration column; ensuring that purge steps adequately eliminate residual isotope in the tubing; verifying that used microfluidic chips have undergone an adequate cool-down time period and no longer exhibit dangerous levels of radioactivity before they are ejected into a disposal bin; and as part of an interlock system prohibiting users from opening shielded boxes unless radiation levels are safe.

In one embodiment, the automated system further comprises electrical contacts to on-chip thermal control using pogo-pins.

In one embodiment, the automated system further comprises an array of needles configured such that when in use the array of needles is pressed against a microfluidic chip, the needles form fluidic connections with ports (inlets and outlets) on the microfluidic chip.

In one embodiment, the automated system further comprises in-line pressure and flow sensors configured to operably monitor any batch-to-batch variation, and operably check to ensure backpressure is not too high (indicating clogging) or too low (indicating membrane damage).

In one embodiment, the automated system further comprises in-line sterile filters placed in a fluidic path between the microfluidic chip outlet and the robotic system for dispensing into sterile vials.

In one embodiment, the automated system is capable of producing multiple, unique doses of ready-to-use radiotracers that are reliably pass all FDA-acceptable release criteria.

In certain aspects, the invention also includes, among other things, the following embodiments and implementations.

Device Materials: The materials used to form a PET tracer synthesis module are chosen to avoid unwanted interactions between reagents and construction materials, which such potential interactions include not only chemical reactions, but physical interactions such as swelling as well as radio-chemistry-specific interactions such as radiolysis. The construction materials need to be compatible with the chemistry of the synthesis, keeping the overall chemical stability, radiological stability, and solvent compatibility in mind while also ensuring that the material remains thermally stable, retains its mechanical properties, withstands high pressures, and can be reliably sourced with known quality controls.

To meet these criteria, microfluidic devices for radiopharmaceutical production have been constructed from glass, metals, silicon, quartz, polymers, elastomers, plastics, ceramics, inorganic materials, and combinations of the above. Early systems used various types of glass, but their capacity to adsorb fluoride during synthesis led to the investigation of the use of plastics and polymers such as polydimethylsiloxane (PDMS), polytetrafluoroethylene (PTFE or Teflon™), fluorinated ethylene propylene (FEP), polyether ether ketone (PEEK), and SU-8. PDMS is one of the most popular materials for producing microfluidic devices, having been used in many systems due to its low cost and simple fabrication while also allowing for solvent exchange via evaporation through thin gas permeable films. Its elastomeric properties permit it to conform and easily seal to other surfaces either reversibly or irreversibly, depending on surface treatment. PDMS can swell when exposed to some solvents, however, and thus some have chosen to avoid this polymer when employing harsh reaction conditions, instead choosing to form devices from SU-8, (an epoxy-based negative photoresist which is easily micropatterned and has superior chemical and mechanical properties including a limited uptake of fluoride and a high resistance to radioactivity) or cyclic olefin co-polymers (COCs), which are also expected to be compatible with the wide range of extreme conditions necessary for fluoride radiochemistry. Many groups including the inventors' lab, however, have reported impressive results when using PDMS devices for radiopharmaceutical production, suggesting that swelling and other interactions with PDMS have negligible impact on tracer production in these platforms. When devices are considered single-use and thus long-term exposure is unimportant. Indeed, as disclosed in EXAMPLE 2 below, interactions between [18F] and PDMS using radionuclide quantities, timeframes, temperatures, and fluidic geometries relevant to PET tracer production are evaluated. For the high activities of interest to clinical PET tracer production, less than 1% of the [18F] introduced into a PDMS chip is retained after a single elution, and no residual activity could be measured after a second elution.

In alternative embodiments, all exposed surfaces of the assembled device can be coated with parylene that is a completely conformal, pinhole-free, biocompatible and inert material exhibiting exceptional barrier properties for most solvents. In addition, the channel walls may be coated with a thin silica glass coating using a TEOS-based approach for example.

Channel/Continuous flow microreactors: In certain embodiments, the microfluidic platforms/chips conceptualized for radiosynthesis application are of the continuous flow or "channel" microreactor, including branching channel networks made with materials resistant to high pressure. Movement through the system is typically pressure-controlled as the reaction proceeds through the in-capillary reaction module. Continuous flow systems boast a very high surface-to-volume ratio with a wide range of material choice with enhanced fluorination as demonstrated by increased reaction yield. By reducing the channel diameter to below the positron interaction range, radiolysis can be significantly reduced; an additional benefit of decreased radiation exposure is provided by the constant movement of the reaction bolus. In certain embodiments, procedures including optimization of chip material, passivation procedures, cleaning cycles and/or precise reagent flow control are performed to minimize clogging due to small channel dimensions and reactants/impurities crashing out of solution due to high surface-to-volume ratios. Additional units may be required to perform the necessary procedures.

Chamber microreactors: Batch mode or "chamber" microreactors are systems developed for radiosynthesis application. These systems can be considered micro-versions of the conventional automated synthesis modules, taking advantage of the benefits of microfluidics while remaining directly scalable to the traditional scale processes. These systems are considerably less prone to clogging than the channel microreactor systems as they employ larger channels and thus lower surface-to-volume ratio (though still considerably higher than conventional systems) and, due to higher mixing efficiencies, can achieve production times as good as or better than traditional scale systems. Processes that are difficult in flow-through systems, such as evaporative solvent exchange and efficient purification, can be integrated into a single microfluidic system using a batch reactor. Isolation of distinct regions prevents cross-contamination and allows for precise reagent loading and delivery. In comparison to continuous flow systems, this approach allows for better radionuclide concentration and lower reagent volumes.

While the above approaches have demonstrated important steps towards microfluidic-based chamber microreactors, they had significant limitations. These include the need for either off-chip column for radionuclide concentration or purification (i.e., not all components are integrated within a single chip and traditional macroscale modules are still needed), limited product quantity or quality (incapable of being directly injected into an animal or human for imaging and thus requiring further refinement), or excessive fabrication complexity and thus high cost, or the need for a large number of interconnects with off-chip pumping, pneumatics, and other components. It is noted that multiplexed, repeatable interconnectivity with off-chip components is, to date, still non-trivial in the field of microfluidics, and while ribbon cables and associated connectors provide facile multiplexed interconnectivity for electrical circuits (hard disk cables, VGA and HDMI cables, etc.), the options for similar standardized, reproducible, and inexpensive repeatable multiplexed interconnectivity for fluidics are quite limited. Recently, to overcome the additional complexity associated with production steps (radionuclide concentration, product purification, etc.) requiring off-chip modules, and with the goal of simplifying the platform to reduce the number of fluidic/pneumatic interconnects with off-chip components, we developed a PDMS-based chamber microreactor system that can successfully produce a full dose of purified tracer that can be directly injected into a rat for imaging. This system provides one of the few examples of a synthesis platform that sequentially performs all of the tracer production processes entirely on-chip, from the [$^{18}$F]fluoride ion concentration to the purification of the tracer prior to injection, and yields a product of sufficient, clinically useful quantity and quality.

Digital Microfluidics: Instead of using mechanical valves, pumps, and channels, approaches employing the concept of "digital microfluidics" on electrowetting-on-dielectric (EWOD) devices utilize electric potentials applied either between two parallel surfaces (a "closed" system) or between electrodes on a single plate (an "open" system) to move, combine, and split individual droplets of liquid. The plates are generally composed of an indium tin oxide (ITO) layer on both the top and bottom glass plates with various gold, silicon nitride, and amorphous fluoroplastic (Teflon) components and coatings. This allows for diverse chemical synthesis processes to be carried out with a single type of EWOD chip. In response to the significant expense, difficulty of construction, and unreliability of the EWOD systems, however, there has recently been a shift in focus towards systems employing passive droplet manipulation for PET tracer synthesis. These systems rely on geometric designs to optimize the motion of the droplets while utilizing the properties of hydrophobicity and hydrophilicity to drive movement. This approach in particular has been suggested to provide a way to routinely produce high molar activity [$^{18}$F]fluorine tracers.

Briefly, the significance of the invention for high-yielding synthesis of radiotracers on-demand production of personalized PET imaging is as follows. Currently, PET tracer production relies upon a centralized facility that generates the radioisotope and produces a large batch of radiotracer to be shipped out to various facilities in the area. This limits production to either large quantities of a single tracer at low cost or a single-batch of a boutique tracer that ends up being prohibitively expensive despite its clinical benefits. Over the past decade or so, engineers have looked to microfluidic technologies to address these limitations. The invention, however, provides solutions to decentralize production sites, leveraging novel microfluidic technology and extensive automation. Accordingly, the inventors envision raw radioisotope delivered directly from the cyclotron to radiopharmacies and on-site, on-demand automated production of ready-to-inject tracers using disposable inexpensive microfluidic chips, thereby allowing the use of boutique, specialized tracers without the significant additional cost currently required. In particular, the proposed microfluidic approach is particularly attractive due to the decreased costs of the synthesis system, the reduced shielding and apparatus footprint, and the reduced amounts of expensive reagents needed. The reduced cost burden has the potential to impact not only clinical production, but is likely to enable more rapid research and development of novel tracers by reducing or eliminating infrastructure needed to embark upon such studies. At Vanderbilt, the inventors have developed a program dedicated to the decentralization of PET tracer distribution pipeline through Vanderbilt University-Radiopharmaceuticals As Precision Imaging Diagnostics (VU-RAPID), a microfluidic-based approach to enabling dose-on-demand production of a range of PET tracers. This novel platform that has the potential for high throughput, complete automation, enhanced product quality and reaction efficiency, is capable of handling multiple different radionuclides and radiochemistries, and supports all necessary tracer production steps on a single chip; radionuclide and commercially available reagents are supplied to the chip input and a ready-to-inject clinically useful PET tracer dose is the eluted product.

These and other aspects of the present invention are further described below. Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

High-Yielding Radiosynthesis of 68GA-PSMA Using a Multiuse Microfluidic Device: Towards on-Demand Production of Personalized Pet Imaging Prostate cancer (PC) is the second most leading cause of deaths among adult males worldwide and the fourth most common cancer overall. Because of its high expression on the surface of prostate cancer cells, prostate-specific membrane antigen (PSMA) has been identified to act as a target for PET molecular imaging and for targeted radioligand therapy.

For diagnostic imaging of PC, one favorable radionuclide is gallium-68 due to several intrinsic advantages. First, it has a physical half-life of 68 min, which is suitable to be applied in macroscale synthesis systems. Second, instead of relying on an on-site cyclotron, $^{68}$Ga can be conveniently obtained from a $^{68}$Ge/$^{68}$Ga generator. Moreover, recent studies have suggested that $^{68}$Ga-PSMA likely possesses more sensitivity than $^{18}$F-fluoromethylcholine or $^{11}$C-choline for evaluation of recurrent prostate cancer. For targeted radiotherapy, $^{177}$Lu-labelled PSMA ligand represents a promising approach in treatment of patients with recurrent and metastatic PC. As a consequence, there has been a growing demand in use of $^{68}$Ga- and $^{177}$Lu-labelled PSMA for imaging and therapy of PC.

In this exemplary example, an inexpensive, high-yielding and multiuse microfluidic device, "RAPID" (Radiopharmaceuticals As Precision Imaging Diagnostics) platform/system, is disclosed, which enables radiosynthesis of both $^{68}$Ga- and $^{177}$Lu-PSMA at substantially reduced cost.

The microfluidic system according to embodiments of the invention includes several miniaturized modules, which can be used to achieve all critical steps such as radioisotope concentration, passive on-chip mixing and heat-aided labeling reaction without the need of any off-chip steps. By starting with a full elution from the $^{68}$Ge/$^{68}$Ga generator, the microfluidic device can generate several doses of $^{68}$Ga-PSMA qualified for direct administration to patients. Furthermore, rapid and high-yielding radiosynthesis of $^{177}$Lu-PSMA has also been demonstrated using the identical microfluidic chip, illustrating the versatility of this platform. Besides, isolated final products are thoroughly examined following standard quality control (QC) conditions to ensure its compliance with Good Manufacturing Practice (GMP) guidelines. Towards the dose-on-demand concept, the invented device/platform would aid in the expansion and availability of PET technology by enabling cost-effective production of various radiopharmaceuticals.

Device Fabrication

In the microfluidic device fabrication, the microchannel pattern was fabricated using facilities within the cleanroom affiliated with the Vanderbilt Institute of Nanoscale Science and Engineering (VINSE). A laser writer (Heidelberg μPG 101) was utilized to create patterns on a silicon wafer. Polydimethylsiloxane (PDMS) (Sylgard 184, part A and part B mixed in 10:1 ratio and degassed) was employed. Briefly, soft lithography was employed to pattern channels in PDMS, which was then bonded to a glass slide (substrate) after exposing to oxygen plasma. Off-chip mechanical valves (Upchurch Valves, V-100D) were used to control the transit of reagents between modules. Syringe pumps (New Era Pump System, NE-300) was used to load solution at controlled flow rate. A hot plate (IKA, Control-VISC) was used to heat the entire microfluidic device during on-chip mixing and labeling reaction.

As schematically illustrated in FIG. 1, the microfluidic chip was constructed with three key components/modules: an on-chip strong cation exchange (SCX) column 110, an on-chip strong anion exchange (SAX) column 120, and a passive in-plane mixing/reaction module 130. Specifically, it is designed to sequentially complete steps: concentrate gallium-68 delivered from the gallium-68 generator, mix eluted gallium-68 with PSMA-11 precursor, and perform heat-aided labelling reaction.

In the exemplary example, each of the on-chip SCX and SAX columns 110 and 120 was about 5 mm in width, about 20 mm in length, and about 100 μm in height. Each of Maxi-Clean SCX and SAX resins (GRACE, about mg, particle size about 50 c) were suspended in ethanol (about 5 w/v %) and loaded into a respective column of the on-chip SCX and SAX columns 110 and 120 using syringe pumps (loading rate: about 100 μl/min). All resins can be trapped by rows of PDMS obstructions, e.g., one or more row of rhombus-PDMS pillars with desired gap formed near the outlet of the on-chip SCX/SAX column 110/120 thus allowing for the construction of columns with demanded functionalities. It should be appreciated that the pillars can be any geometric shape such as square, rectangle, circle, and so on. The in-plane passive mixing module adopted a flow-focusing geometry 131 at the entrance. The dimension of a zigzag mixing channel 132 was about 500 μm in width, about 34 mm in length and about 100 μm in height. In addition, the width and height of rhombus-shaped obstructions were about 50 μm and about 100 μm, respectively. The sizes of all of mixers were equal. The on-chip reaction cavity (chamber) 133 was fabricated using an 8-mm-diameter punch (Ted Pella) and a 1-mm thick PDMS membrane was aligned and plasma bonded on top of the reactor 133, allowing for maximum volume of 500 μl.

Figures 2A, 2B, 2C, 2D:
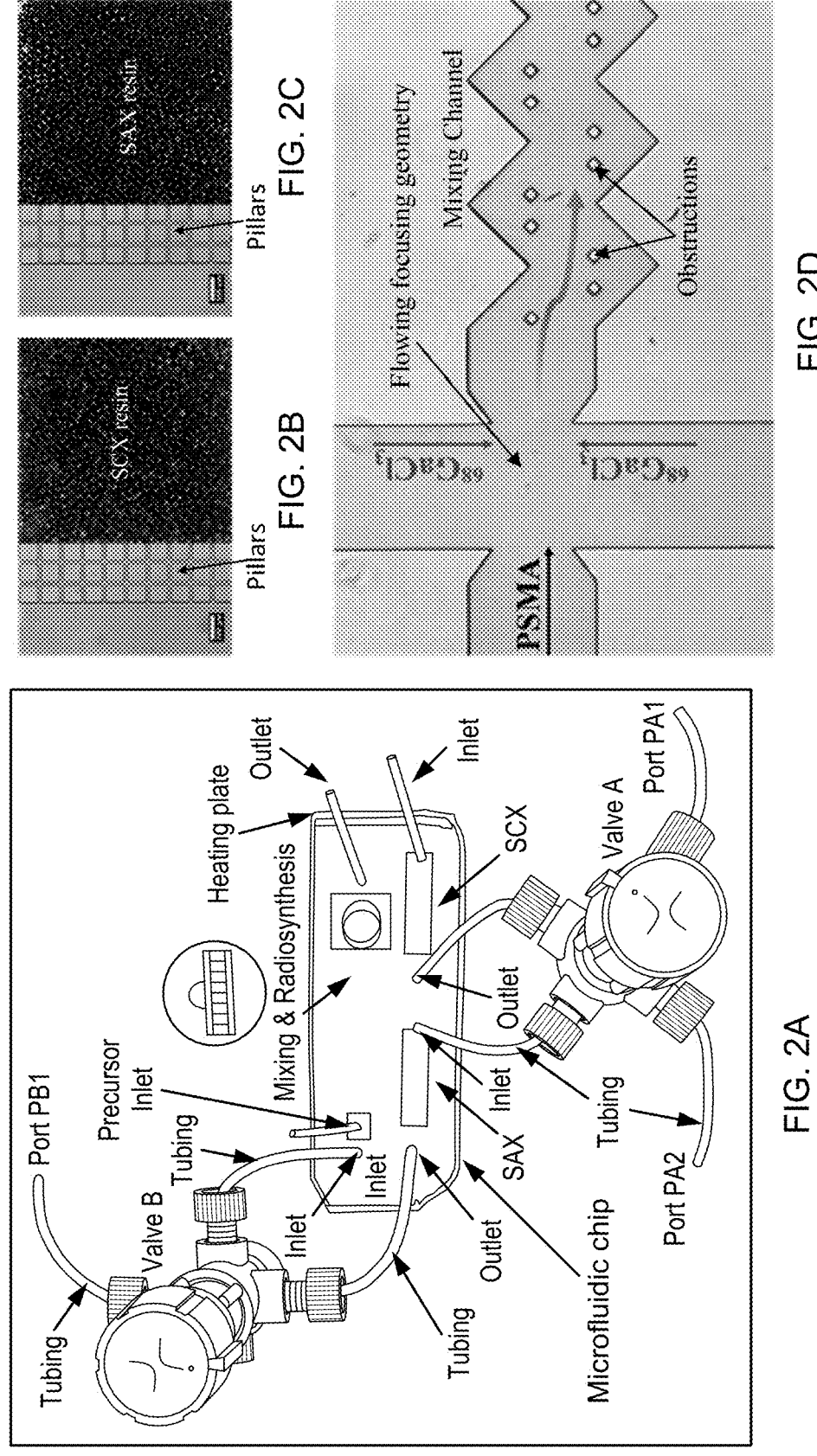
FIGS. 2A-2D are photographs of the fabricated microfluidic device for the radiosynthesis of $^{68}$Ga-PSMA-11 (FIG. 2A), SCX (FIG. 2B) and SAX (FIG. 2C) resins trapped inside microchannels, and the entrance of mixing module (FIG. 2D) with diamond-shape obstructions inserted throughout the zigzag microchannel, according to one embodiment of the invention.

FIG. 2A is photographs of the fabricated microfluidic device for the radio synthesis of $^{68}$Ga-PSMA-11. FIGS. 2B-2C show SCX and SAX resins trapped inside the microchannels of the on-chip SCX and SAX columns, respectively. FIG. 2D shows the entrance of the mixing chamber with diamond-shape obstructions inserted throughout the zigzag microchannel.

In this exemplary embodiment, the microfluidic chip is formed of a patterned PDMS layer on a glass slide/substrate. It should be appreciated that the microfluidic chip can be formed of any suitable materials, for example, a patterned layer on the top of a non-patterned polymer layer/substrate or a non-patterned glass slide/substrate, or an etched glass slide on the top of a non-patterned polymer layer/substrate or a non-patterned glass slide/substrate. The polymer can be any polymer in addition to PDMS.

In the exemplary embodiment, off-chip mechanical valves, e.g., valves A and B (Upchurch Valves, V-100D), as shown in FIG. 2A, are used to control the transit of reagents among these three modules. A syringe pump (New Era Pump Systems, NE-300, not shown herein) is used to control flow of the various reagents.

In some embodiments, on-chip valves such as on-chip rotary planar valves (RPV), and/or on-chip pump such as on-chip rotary planar peristaltic micropump (RPPM) can also be utilized to control the transit of reagents among these three modules, and flow of the various reagents.

Reagents and Materials

All other reagents were of analytical grade, and purchased from commercial source and used as received. For all experiments, gallium-68 was obtained from a $^{68}$Ge/$^{68}$Ga-generator (Eckert & Ziegler, Berlin, Germany) that was eluted using sterile, GMP certificated 0.05 M HCl solution. The amount of radioactivity loaded at the beginning was about 30 mCi. The GMP-grade PSMA-11 precursor was purchased from ABX (Dresden, Germany). About 0.25 M sodium acetate buffer was injected and fully mixed with PSMA-11 precursor prior to labeling reaction. Resins obtained from Maxi-Clean SCX/SAX (GRACE, about 600 mg, particle size about 50 μm) cartridges were used to form on-chip columns. On-chip SCX and SAX modules were preconditioned using about 1 mL 5.5 M HCl, followed by rinsing with about 5 mL DI water (18 MΩ, Milli-Q Integral ultrapure water). Notably, all experiments were performed using facilities with the lowest possible metal content to avoid unfavorable interference with $^{68}$Ga-PSMA labelling reaction.

Analytical Facilities

A Hitachi HPLC (LaChrom Elite, Pump L-2130) equipped with a wavelength UV detector (L-2400, 254 nm) and inline radiation detector (Inline Carroll & Ramsey) was used to evaluate radiochemical purity. A $C_{18}$ column (Phenomenex Gemini, particle size about 10 μm, 150×4.6 mm) was used. For the mobile phase, acetonitrile (referred as A1) mixed with water containing about 0.1% trifluoroacetic acid (TFA) was used with gradient as following: 0% A1/100% TFA for about 0-2 min, 100% A1/0% TFA for about 8-10 min. The flow rate was constantly set as about 1 mL/min. Moreover, radiochemical purity was also examined by radio thin layer chromatography (TLC) using ITLC (instant TLC) paper strips (Varian). The TLC buffer included a mixture of about 70% ethanol and about 0.9% saline in about 1:3 volume ratio. All experiments that involved radioactivities were performed in a lead-shielded hot cell. The value of radioactivity was measured using a calibrated dose calibrator (Capintec, CRC-25PET). The radiochemical yields were evaluated as a percentage of total activity of $^{68}$GaCl$_3$ initially delivered from the generator. Unless specified elsewhere, all efficiencies are calculated based on decay-corrected values.

Mixing Simulation

COMSOL Multiphysics was used to carry out numerical simulation of mixing of two streams in the microchannel. Mixture model (transport of diluted species) was used to extract the concentration profile of PSMA-11 precursor throughout the mixing zone. The dispersion of two miscible streams in a laminar-flow channel was driven by the velocity profile of the flow. The initial loading velocities from all three inlets were set to be about 100 μl/min. The initial concentration of PSMA-11 precursors and gallium-68 was set to be 100 and 0, respectively. To simplify the model, the properties of two streams were defined as incompressible water. The boundary condition for the inner walls of microchannels was set as no slip condition.

Microfluidic Chip Operation

Figure 3A:
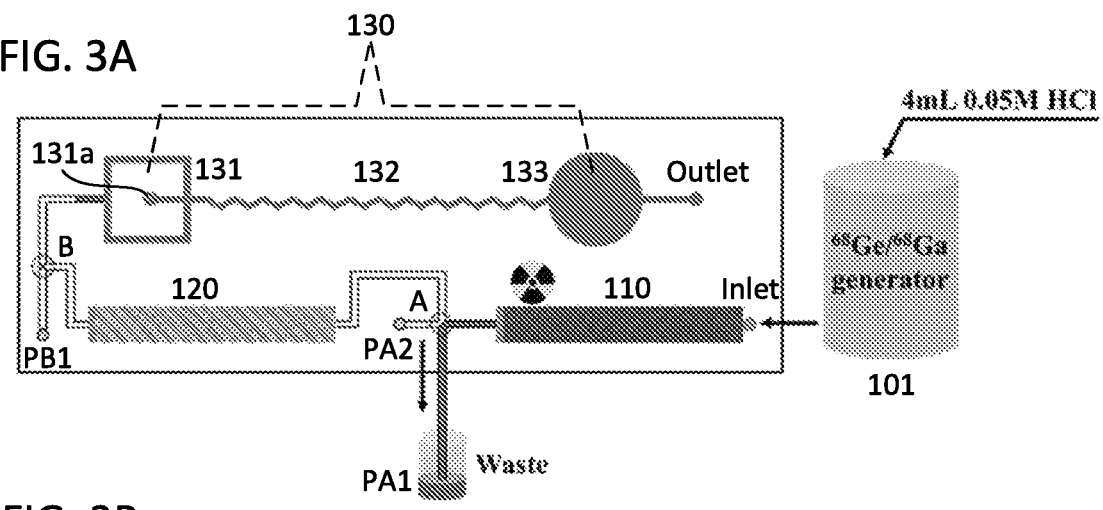
FIGS. 3A-3C are schematic diagrams showing the three sequential labelling steps.
Figure 3B:
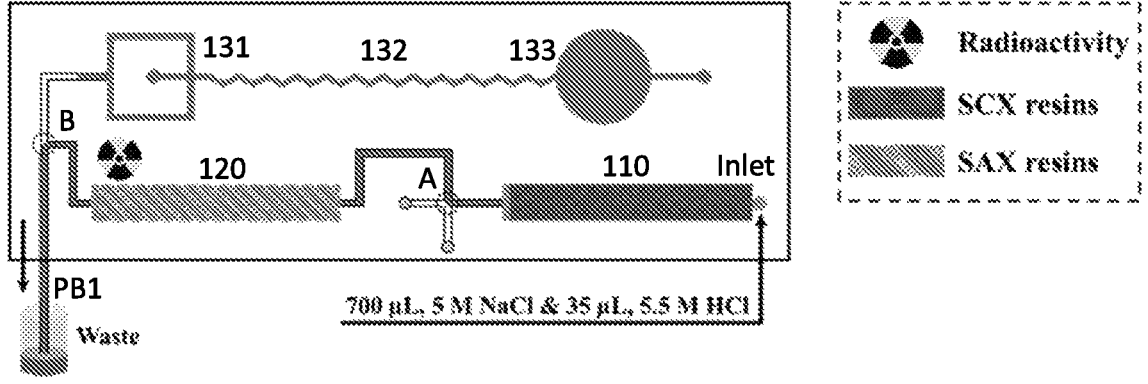
Figure 3C:
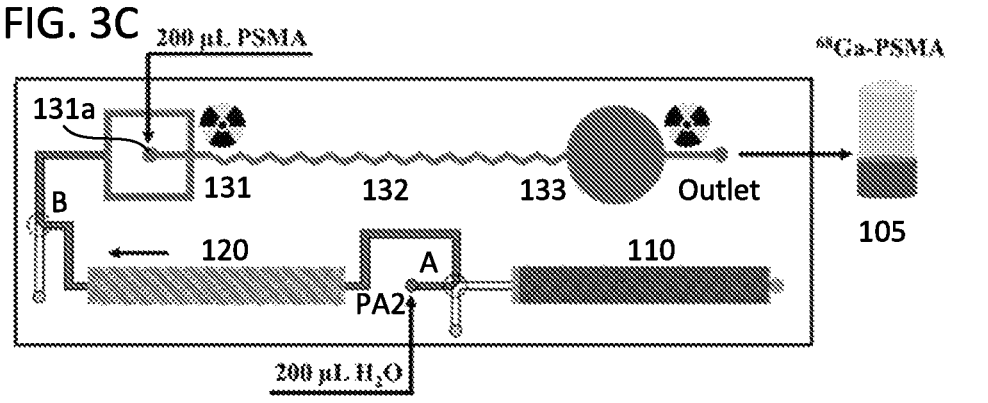

FIGS. 3A-3C are schematic diagrams that show the three most critical steps of $^{68}$Ga-PSMA production in the microfluidic device according to one embodiment of the invention. The amount of radioactivity of eluted gallium-68 used in experiments was 29.8±1.15 mCi in about 4 ml 0.05 M HCl elution. First, a full elution of the gallium-68 generator 101 was concentrated by the on-chip SCX column using a syringe pump with an about 800 µl/min loading rate via the inlet of the on-chip SCX column 110 (FIG. 3A). Then, about 0.1 mL air was loaded at the same loading rate to ensure that all liquid completely passed through the on-chip SCX column 110. The isolated waste was collected in a glass vial via port PA1 of valve A and the remaining activity was immediately measured. The amount of radioactivity of the initial gallium-68 elution for injection, concentrated on the SCX column 110, and collected in the glass vial was separately measured. Thus, the correlation between the mass of packed SCX resins and the concentration efficiency can be mapped out.

Second, elution off of the SCX column 110 and onto the SAX column 120 was achieved using a mixture of about 700 µl of 5M NaCl and about 35 µl of 5.5M HCl. As shown in FIG. 3B, the solution was injected from the inlet of the SCX column 110 at a loading rate of about 200 µl/min. Meanwhile, released solution was controlled by an off-chip valve A to slowly pass through the SAX column 120. Similarly, another about 0.1 mL air was injected from the inlet of the SCX column 110 to enable all solution to flow sequentially through all columns 110 and 120.

Next, to release trapped isotopes off the on-chip SAX module/column 120, about 200 µl DI water was injected from the inlet (via port PA2 of valve A) of the SAX column 120 with a loading rate of about 200 µl/min, as shown in FIG. 3C. Simultaneously, the released gallium-68 was mixed with PSMA-11 precursor, loaded via the precursor inlet of the in-plane passive mixing geometry 131, by flowing through an in-plane mixing channel 132. The precursor solution was prepared by dissolving about 10 µg PSMA-11 ligand in about 1 mL of 0.25 M sodium acetate buffer, resulting in an about 10 µg/mL concentration. Next, the microfluidic chip was heated at about 95° C. on a preheated hot plate to complete labelling reaction. The final volume of synthesized product 105 was about 400 µL, which can be further diluted to desired volume for dose administration and imaging injection.

Results and Discussion

Direct on-chip concentration of $^{68}$Ga: The goal of the concentration step focuses on effectively capturing majority of $^{68}$Ga from a full elution of the generator (about 4 mL) using miniaturized microfluidic columns. While numerous methods have already been developed and employed in clinical production, most of these methods primarily rely on the use of commercially available cation/anion exchange cartridges. More importantly, marginal effort has been devoted to determining advantages and disadvantages of these approaches when applied in a microfluidic system.

Previous studies have reported several different strategies that are routinely used for efficient $^{68}$Ga concentration in practical production. Since the goal here is to process a full elute of $^{68}$Ga from the original generator, the invention hence employs a two-step approach that relies on combined effects of cationic concentration and anionic purification. This approach is extremely advantageous when applied in a microfluidic system due to the following aspects: first, it does not involve the addition of buffer solution or organic solvents, thus eliminating the necessity of purification; second, the combination of the SCX and SAX provides the capability to handle a full elution of $^{68}$Ga, demonstrating the capability to produce several imaging doses; third, released $^{68}$Ga in small volume of pure water exhibits high radionuclide and chemical quality, and low acidity, thereby allowing for direct use for a variety of radiolabeling reactions.

In this example, both on-chip SCX and SAX columns were constructed by trapping different functional resins inside the microchannels with a trapping mechanism, which in some embodiments, includes rows of square pillars with predefined gaps near the outlet of microchannel. It should be appreciated that the pillars can be any geometric shape. FIGS. 2B-2C show optical images of SCX and SAX resins densely packed by the end (outlet) of the microchannels. To examine the performance of on-chip columns, trapping and releasing trials were carried out separately on each column. Based on the measured radioactivity using a dose calibrator, the radioactivity concentration efficiency (RCE) and radioactivity release efficiency (RRE) was determined by the following expression.

$$RCE = \frac{\text{On-chip trapped radioactivity}}{\text{Initially loaded radioactivity}}$$

$$RRE = \frac{\text{Released radioactivity}}{\text{On-chip trapped radioactivity}}$$

Additionally, several operating parameters including mass of loaded resins, solution loading rate, and volume of releasing buffer were comprehensively studied. Since the underlying mechanism for $^{68}$Ga concentration relies on the fact that $^{68}$Ga$^{3+}$ eluted off the generator should be absorbed on the surface of silica-based SCX resins, it is thus critical to determine the correlation between mass of loaded resins and concentration efficiency. Rigorous testing revealed that about 8 mg of the SCX resins (RCE=96%, n=5) and about 10 mg of the SAX resins (RCE=91%, n=5) were required to achieve efficient trapping performance over a loading duration of about 5 min.

Figure 8:
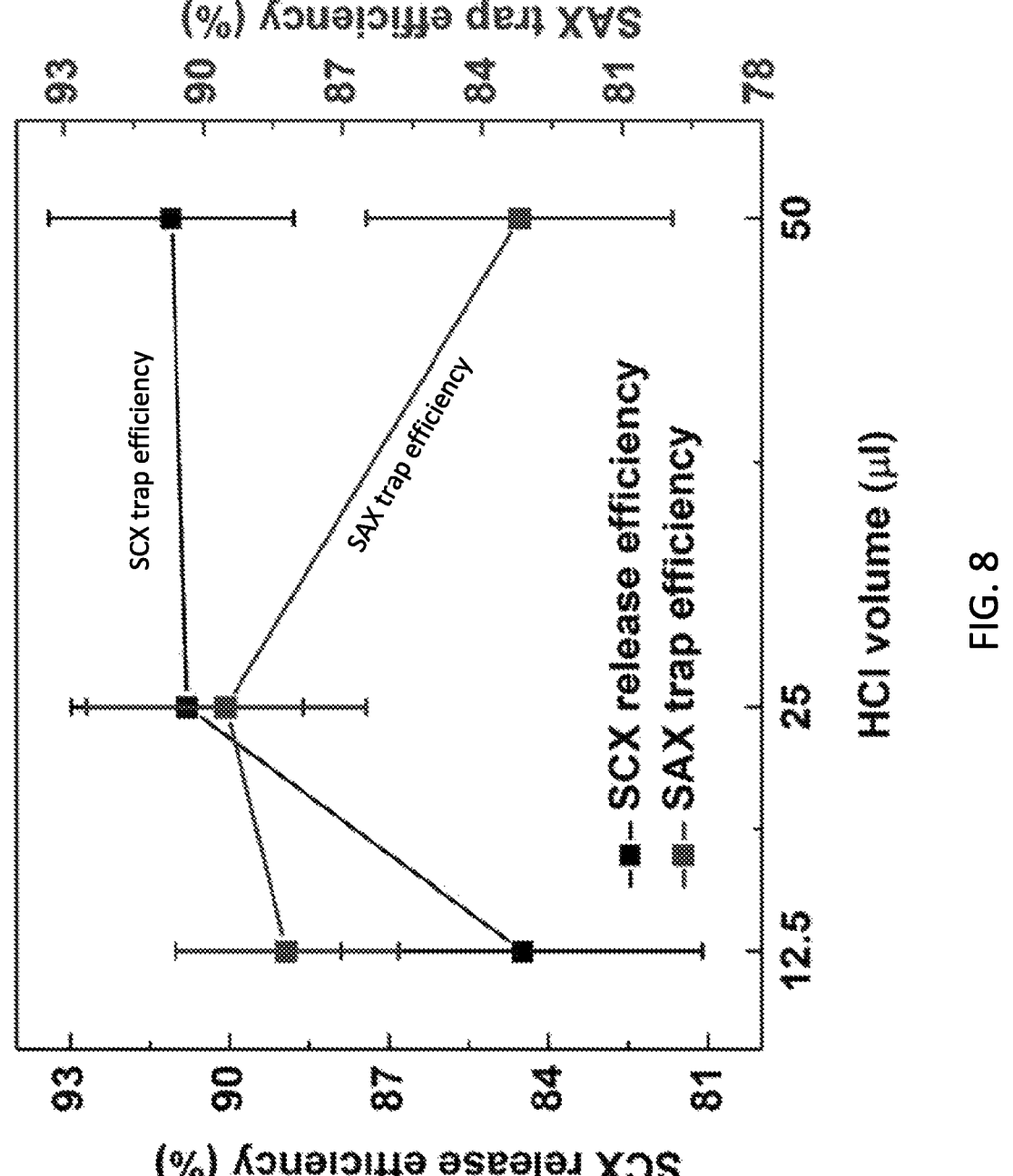
FIG. 8 shows the relationship between volume of HCl and both SCX release efficiency and SAX trap efficiency, according to one embodiment of the invention.

To release pre-trapped $^{68}$Ga$^{3+}$ off the SCX column, a method described by Mueller et al. was employed, where a concentrated NaCl solution containing a very low amount of HCl was used to convert the cationic $^{68}$Ga$^{3+}$ to the anionic $[^{68}$GaCl$_4]^{-}$. As illustrated in FIGS. 1 and 3B, elution released off the SCX column was immediately directed to pass through the SAX column, where $[^{68}$GaCl$_4]^{-}$ can be absorbed by SAX resins. Hence, it is critical to optimize elution solution to enable both efficient desorption of $^{68}$Ga$^{3+}$ and efficient adsorption of $[^{68}$GaCl$_4]^{-}$. By adjusting the volume ratio of 5.5 M HCl relative to 5 M NaCl, it was found that an elute including about 700 µL of 5M NaCl and about 35 µL of 5.5M HCl enabled the best performance (SCX RRE=90.8%, n=5 and SAX RCE=89.5%, n=5), as shown in FIG. 8. As the solution was slowly loaded through the SAX column, the excess of HCl can be directly removed from the microfluidic chip. After eluting with about 200 µL pure water, the collected isotope, now in the form of $^{68}$Ga$^{3+}$, exhibited a high chemical and radiochemical purity.

As summarized in Table 1, the alteration of radioactivity was measured at critical steps to assess the efficiency of each process and identify potential areas for optimization. Starting from a full $^{68}$Ga elution from the generator, the total trapping efficiency of the combination of SCX and SAX columns is about 73.7%. The total time period required for completing gallium-68 concentration is about 12 min. It is noteworthy to mention that additional optimization on factors such as the selection of SCX and SAX materials (e.g., use of resins with higher porosity and larger surface area) and microchannel design could lead to better overall RCE performance.

TABLE 1

Experimental results of the efficiency of
miniaturized SCX and SAX columns at critical steps.
All efficiencies are calculated based on decay-corrected values.

| Parameter | Run 1 | Run 2 | Run 3 | Run 4 | Run 5 | Average |
|---|---|---|---|---|---|---|
| Loaded activity (mCi) | 30.2 | 28.4 | 31.4 | 29.1 | 30.1 | 29.8 ± 1.15 |
| SCX RCE (%) | 96.8 | 97.0 | 97.1 | 97.9 | 93.8 | 96.5 ± 1.58 |
| SCX RRE (%) | 87.3 | 90.4 | 91.0 | 92.5 | 92.7 | 90.8 ± 2.18 |
| SAX RCE (%) | 87.6 | 93.3 | 92.3 | 87.3 | 87.2 | 89.5 ± 3.00 |
| SAX RRE (%) | 93.0 | 94.2 | 95.0 | 93.5 | 93.7 | 93.9 ± 0.76 |
| Total loss (%) | 31.2 | 22.9 | 22.5 | 26.1 | 29 | 26.3 ± 3.75 |
| Total trapping (%) | 68.8 | 77.1 | 77.5 | 73.9 | 71 | 73.7 ± 3.78 |

Evaluation of on-chip mixing performance: Because of the short time period required for gallium-68 incorporation reaction in a microfluidic system shown in FIG. 2A, it is therefore crucial to achieve thorough mixing prior to heating in reactors. It is known that mixing of several streams of solution inside a microfluidic channel depends primarily on diffusion, which occurs in an unfavorably slow manner due to the small Reynolds number (Re<<1). In this example, a passive microfluidic mixing system that combined the effect of in-plane obstructions inside microchannels and repetitively wavy microchannels was employed, as shown in FIG. 2D. Due to the fact that passive mixing neither complicates device fabrication nor requires additional power, such system hence provides a simple yet efficient fashion to achieve enhanced mixing performance.

As shown in FIG. 2D, a flowing focusing geometry was used at the entrance of mixing section by simultaneously loading released $^{68}$Ga$^{3+}$ from the top and bottom channels and PSMA-11 precursor from the middle channel. In order to characterize its mixing performance, fluorescent beads suspended in water was injected from the middle channel while pure water was injected at the same time from the other two channels. The solution was loaded using two syringe pumps at the rate of about 100 µL/min. A digital microscope camera (Zeiss) was used to record and visualize the mixing performance along the flow direction at different positions.

Figures 4A, 4B, 4C, 4D, 4E, 4F:
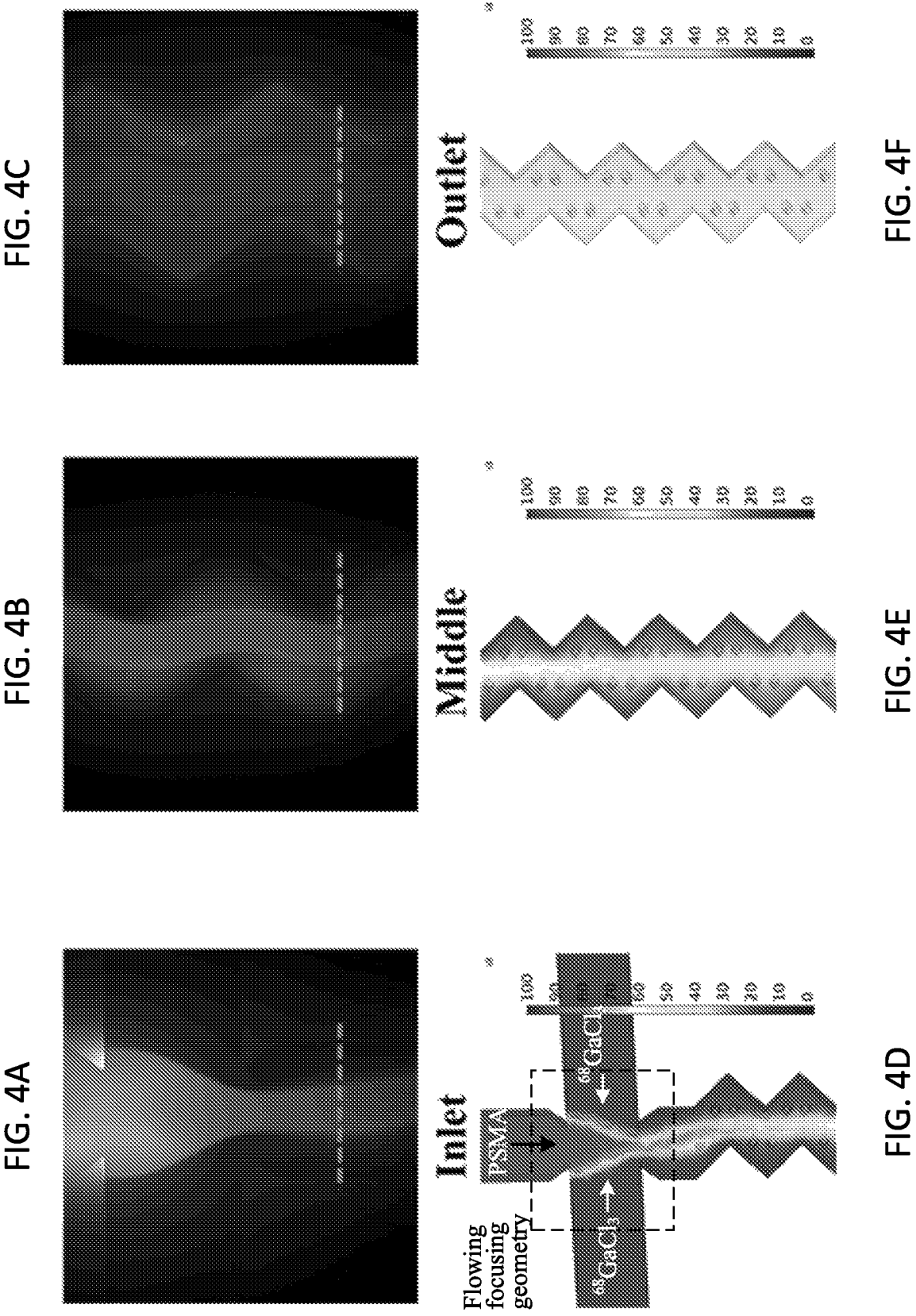
FIGS. 4A-4F show experimental evaluations of the mixing performance using the combination of inserted obstructions and zigzag microchannels, according to one embodiment of the invention. The captured fluorescent images indicate mixing results at inlet (FIG. 4A), middle (FIG. 4B) and outlet (FIG. 4C), respectively, which are in good agreement with corresponding numerical simulation. The variation of concentration profiles at various positions at inlet (FIG. 4D), middle (FIG. 4E) and outlet (FIG. 4F) along the microchannel are shown in FIGS. 4D-4F.
Figure 4G:
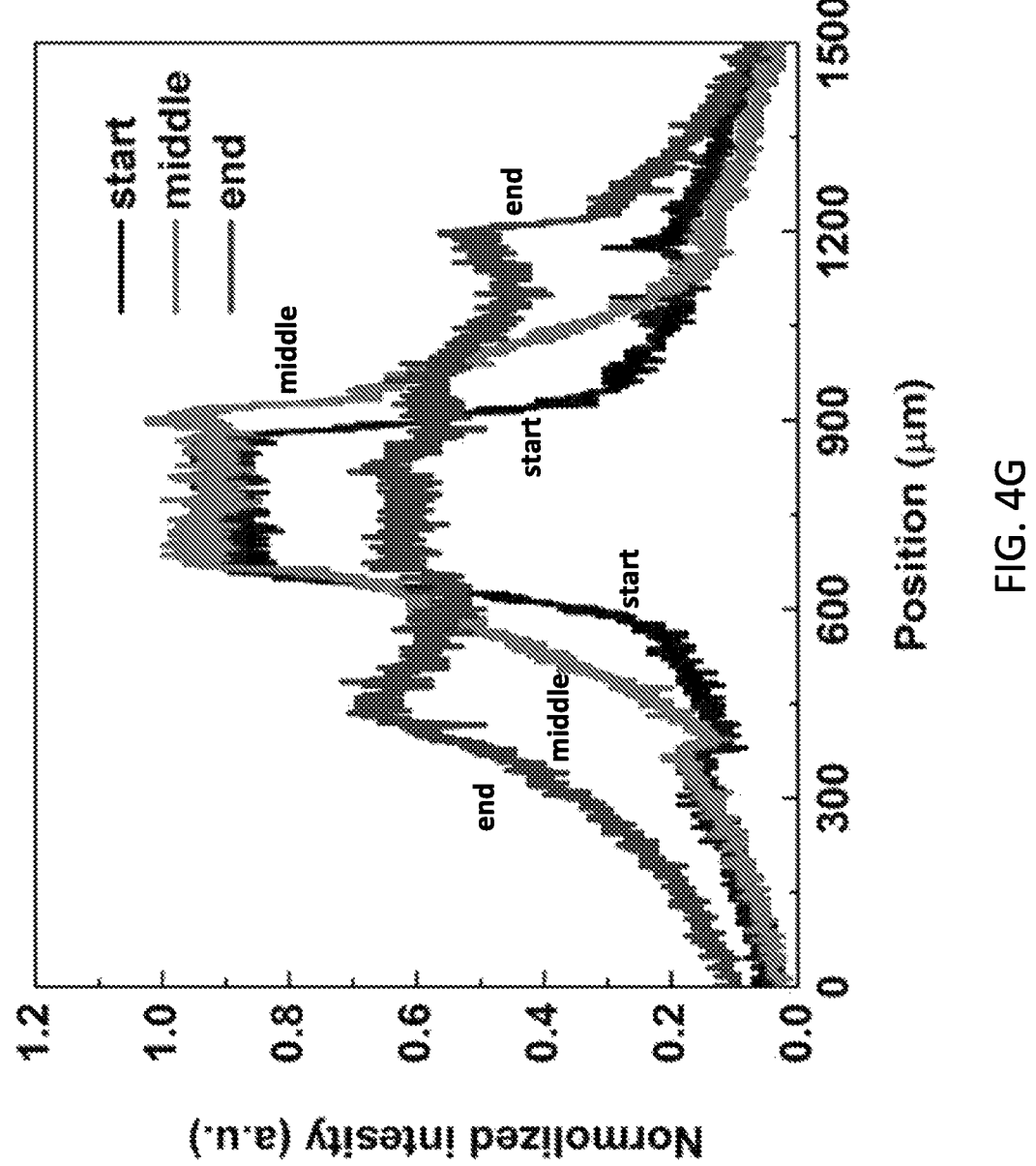
FIG. 4G shows normalized fluorescent intensities for characterization of mixing performance after passing through the on-chip mixing module, according to one embodiment of the invention.

FIGS. 4A-4C describe captured fluorescent images at the inlet, middle, and outlet of the mixing channel. By visually observing the width alteration of the middle fluorescent stream, it is clear to conclude that sufficient mixing is achieved near the end of the mixing channel. Moreover, the mixing performance was quantified by measuring the fluorescent intensity perpendicular to the flow direction (illustrated by red dashed lines in FIGS. 4A-4C). FIG. 4G depicts measured results of the normalized fluorescent intensity versus the width of fluorescent stream. Additionally, COMSOL numerical simulation was performed to predict the mixing tendencies of two solutions based on devised micro-mixers. The red stream injected from the middle channel represents PSMA-11 precursor and the blue streams injected from two side channels represent pre-concentrated gallium-68. The variation of concentration profiles at various positions along the microchannel are shown in FIGS. 4D-4F. As expected, simulated mixing patterns are in good agreement with experimental results, indicating the realization of complete mixing after flowing through the micromixer.

Optimal radiosynthesis conditions: Because of enhanced mass and heat transfer in a microfluidic system, traditional reaction conditions that are routinely adopted for macroscale synthesis are not optimal for microfluidic systems. In order to improve microfluidic-based RCY without affecting labelling efficiency, a systematic study was conducted by examining a variety of reaction parameters such as reaction time, reaction temperature, pH, and precursor concentration. The preliminary investigation started from well-established macroscale protocols, specifically heating the mixture including about 100 µL concentrated $^{68}$Ga and about 100 µL, about 10 µg/mL PSMA-11 precursor in a sealed vial at about 100° C. for about 10 min. Subsequently, only one reaction factor at a time was altered, leaving the other factors unchanged. Therefore, the impact of targeted parameter can be determined using radio-TLC analysis.

Figures 5A, 5B, 5C, 5D:
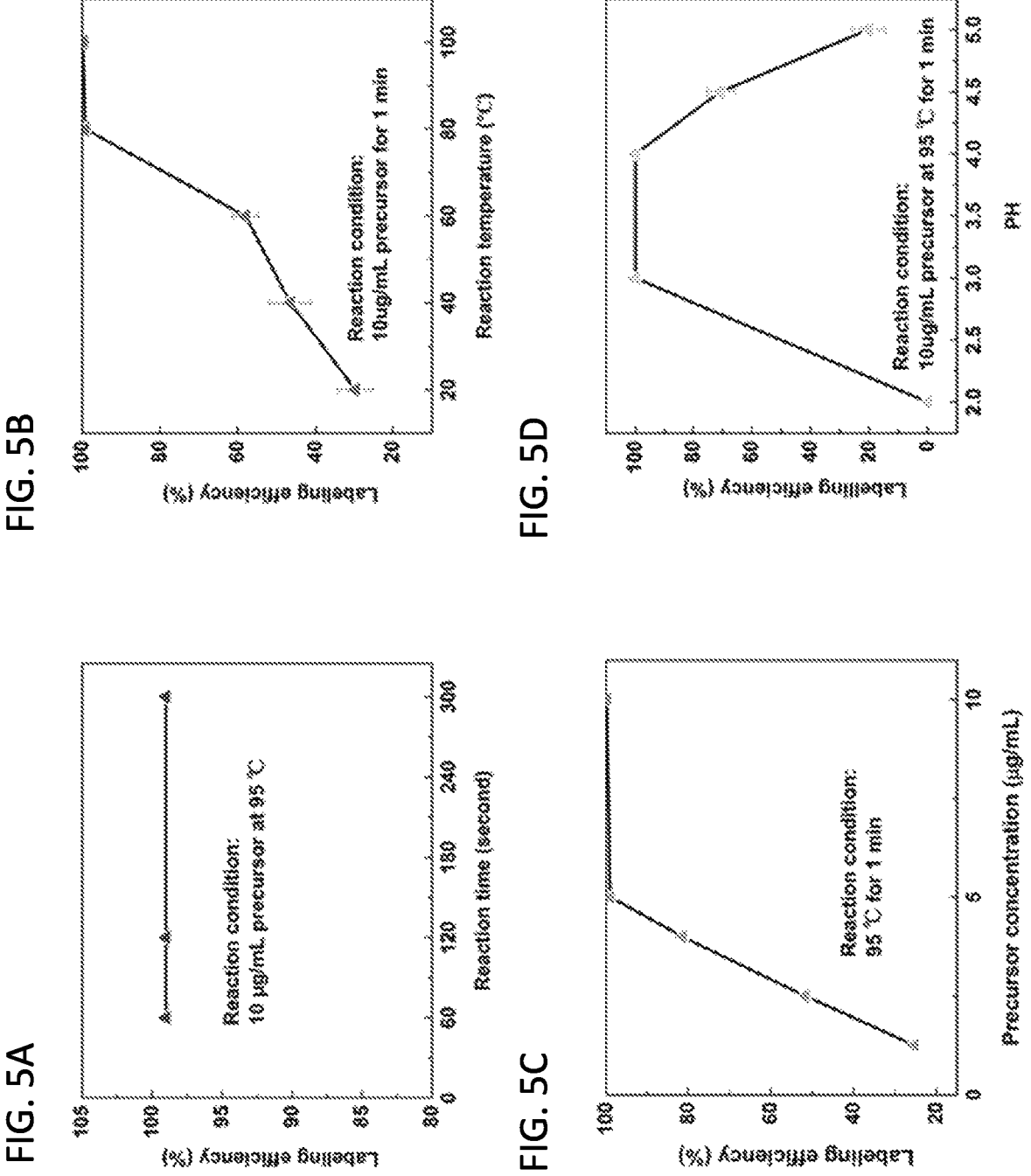
FIGS. 5A-5D show investigation on optimal reaction conditions for $^{68}$Ga labeling reaction in the microfluidic device, according to one embodiment of the invention. Several parameters including reaction time (FIG. 5A), reaction temperature (FIG. 5B), precursor concentration (FIG. 5C), and pH (FIG. 5D) are studied.

In the efforts to reduce total synthesis time, the correlation between reaction time and resulting reaction efficiency was first investigated, as shown in FIG. 5A. It was found that the microfluidic system can obtain high conversion efficiency at substantially reduced duration. Specifically, labeling efficiency of about 99% was achieved by heating at about 100° C. for about min, which consumed one-tenth of the time taken by clinically relevant reactors. Afterwards, the impact of reaction temperature was studied by performing radiosynthesis at diverse temperatures ranging from about 20 to about 100° C. for about 1 min. As shown in FIG. 5B, it is clear that sufficient heating is indispensable in order to obtain exceptionally high labeling efficiency. Interestingly, it was observed that there might exist a threshold temperature (about 80° C.) above which labeling efficiency of 99% can be reliably achieved.

Specific activity of PET tracers is one of the most critical factors that are typically used to evaluate the portion of nonradioactive form of the tracer, which can saturate rare biological receptors, and worsen image quality. In the attempt to achieve high specific activity, experiments focusing on lowering the concentration of PSMA-11 precursor were conducted by performing radiosynthesis under identical conditions (heating at about 100° C. for about 1 min) except varying on concentration of precursor. As shown in FIG. 5C, it is found that about 5 µg/mL PSMA-11 precursor is sufficient to result in labeling efficiency of about 99%. Furthermore, the specific activity of isolated product is about 20 mCi/µg, which is 16 times greater than that of routinely produced doses in clinical environment. Additionally, the appropriate range of pH that enabled high-efficiency reaction was found to be 3-4 (FIG. 5D), which is constant with macroscale production.

Building on abovementioned results, the optimal reaction conditions in the microfluidic system involve the use of about 5 µg/mL PSMA-11 precursor by heating at about 100° C. for about 1 min. To guarantee high success, it is essential to note that the complete synthesis must be carried out without the presence of any trace of heavy-metal contaminations. Using developed protocol, tens of synthesis runs have been successfully obtained.

Full production and quality control: To evaluate the overall radiochemical yield of isolated $^{68}$GAa-PSMA-11, full production runs including concentration, radiosynthesis, and formulation were performed using reported microfluidic platform. The final formulated product was collected as a clear, sterile, and injectable solution. As listed in Table 2, total production time, radiochemical yield, and specific activities are compared to those that are routinely obtained in clinical environment. Generally, the developed microfluidic platform demonstrates improved overall performance in terms of reaction efficiency, overall yield, and specific activity than macroscale automated production.

TABLE 2

Production performance comparison between routinely employed
system and reported microfluidic system.

| | Traditional | This report |
|---|---|---|
| Reactor type | Glass vial (5-20 mL) | Microfluidic device |
| Radiolabeling conditions | 100° C., 10 min | 100° C., 1 min |
| Radiochemical purity (%) | >95 | >99 |
| Purification | Solid phase purification | Not required |
| Total time (min) | 25-20 | 15 |
| Average RCY (%) | 90 | 70 |
| Specific activity (mCi/ug) | 1.25 | 20 |

Figure 6:
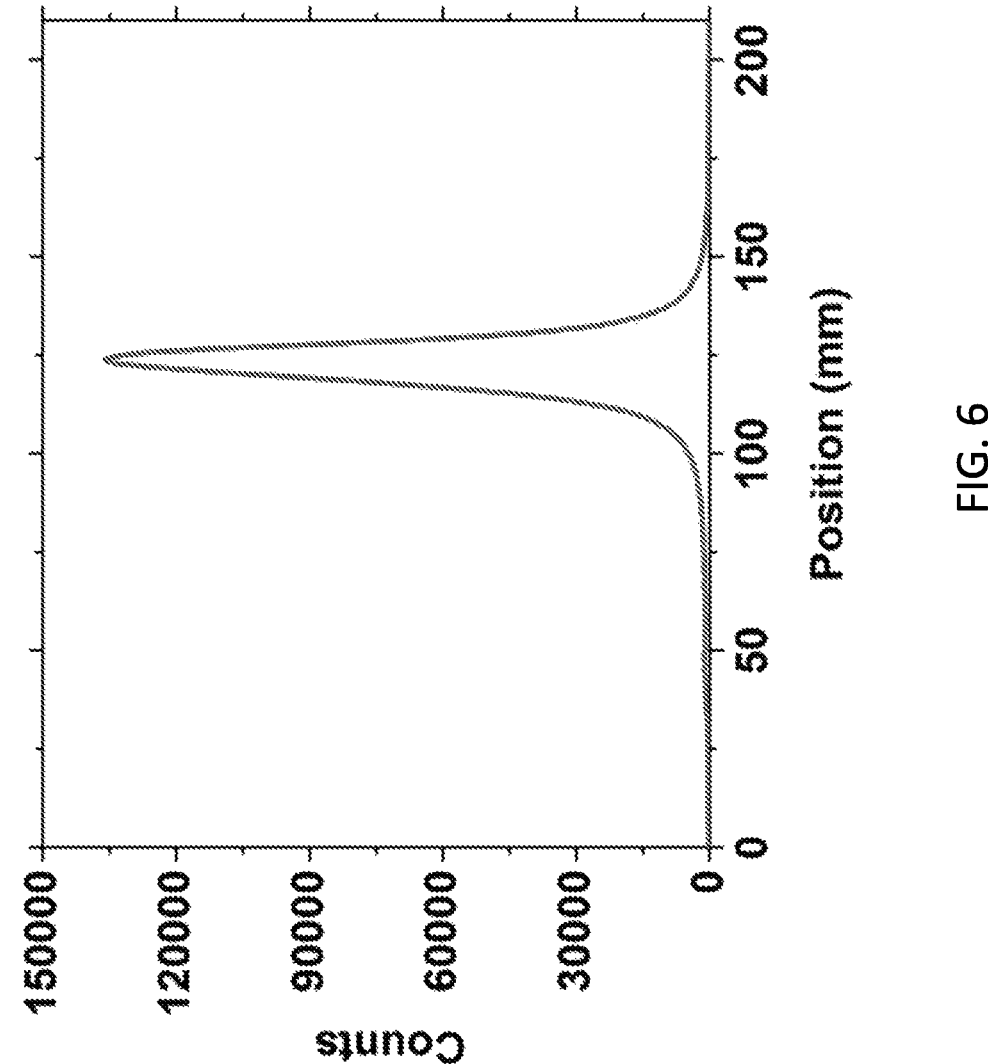
FIG. 6 shows an analytical TLC profile of $^{68}$Ga-PSMA-11 synthesized using the microfluidic chip, showing quantitative conversion, according to one embodiment of the invention.
Figures 7A, 7B:
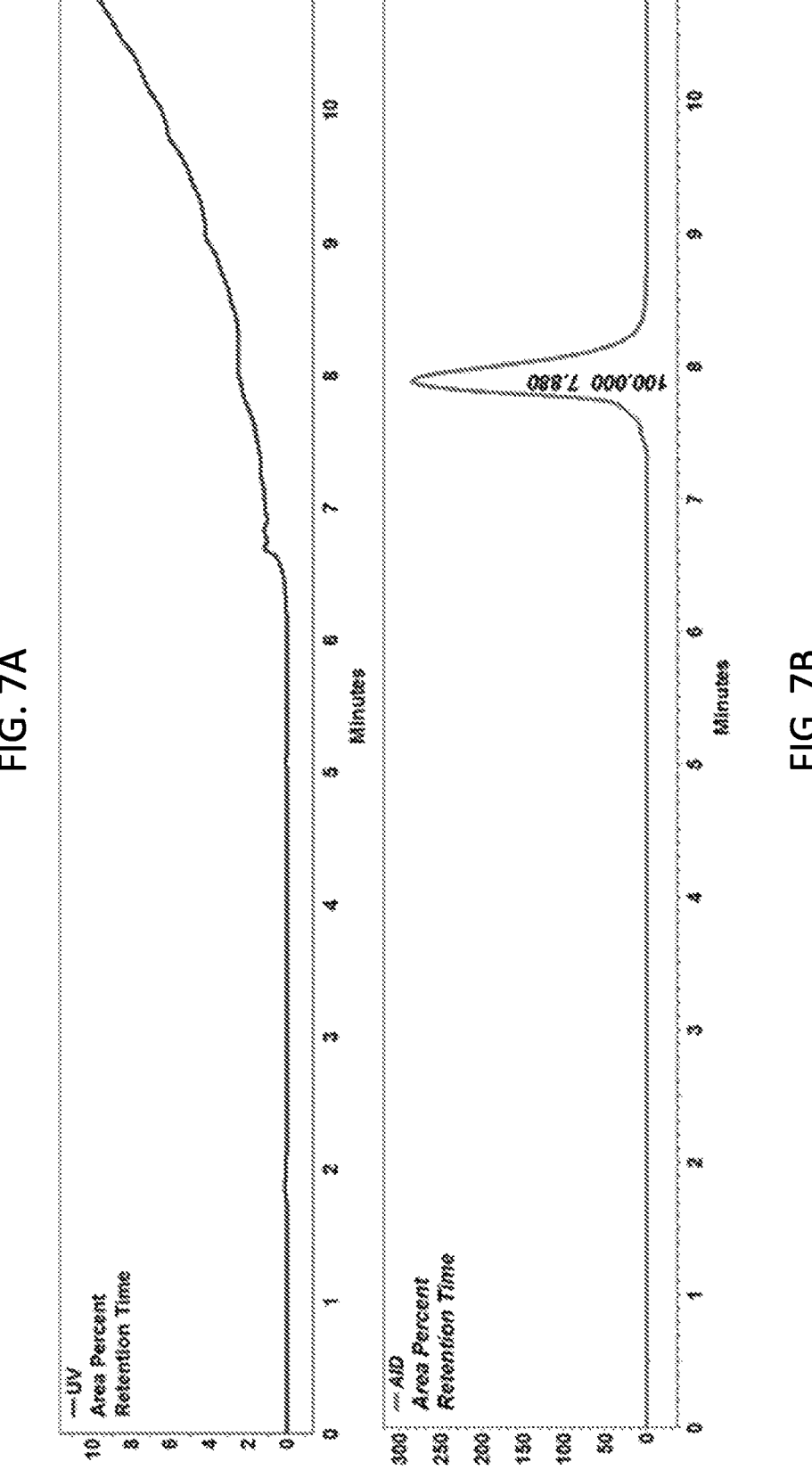
FIGS. 7A-7B. Analytical HPLC trace of $^{68}$Ga-PSMA, according to one embodiment of the invention. The top blue curve (FIG. 7A) and bottom red curve (FIG. 7B) chemical and radiochemical purity, respectively. The retention time of $^{68}$Ga-PSMA is about 7.88 min.

A radio-TLC chromatogram of synthesized product is shown in FIG. 6 and the $^{68}$Ga-labelled peptide has an approximate retardation factor of about 0.8-1.0. Using the microfluidic device, the incorporation efficiency of 100% can be consistently achieved as determined by radio HPLC chromatogram (FIG. 7B). The only peak at about 7.88 min corresponds to the retention time for synthesized $^{68}$Ga-PSMA-11, indicating no remaining of free $^{68}$Ga. It is noteworthy to mention that such high chemical and radiochemical purities allow for further simplification of synthesis procedures as it can eliminate the need of HPLC purification which is routinely required in macroscale system. Additionally, the stability of final product at room temperature was examined by radio-HPLC for duration up to about 4 hours. Based on obtained results, no discrepancy on retention time or product purity was observed, suggesting good stability.

After adding about 2 mL sodium acetate buffer into isolated reaction mixture, the final pH of formulated product was 6-7. After sterile filtration, the reaction mixture exhibited a radiochemical purity of 100% that satisfied the standard release criterion and the final product can be diluted for dose administration to any desired volume for animal or clinical use. The formulated solution was examined by standard quality control tests to assess its compliance with U.S. Food and Drug Administration requirements for injectable PET tracers, as listed in Table 3.

TABLE 3

Quality control tests of synthesized $^{68}$Ga-PSMA
using developed microfluidic system

| Clinical QC test | Clinical acceptance criteria | Analysis of on-chip synthesized PET probes |
|---|---|---|
| Appearance | Clear and particle-free | Clear and particle-free |
| Filter integrity | Meet pressure specify by manufacture | Meet pressure specify by manufacture |
| pH | 4-8 | 4 |
| Radiochemical purity (%) | >90 | >99 |
| Identity | Matches retention time of standard (TLC) | Matches retention time of standard (TLC) |

TABLE 3-continued

Quality control tests of synthesized $^{68}$Ga-PSMA
using developed microfluidic system

| Clinical QC test | Clinical acceptance criteria | Analysis of on-chip synthesized PET probes |
|---|---|---|
| Half-life (min) | 64-72 | 68 |
| Sterility | No growth observed for 14 days | No growth observed for 14 days |
| 68Ge breakthrough | <0.01% of the total radioactivity is 68-Ge at the time of product expiration | <0.01% of the total radioactivity is 68-Ge at the time of product expiration |
| Residual solvents | Dependent on methodology | Not required |

Quality control of synthesized radiopharmaceutical: After labeling reaction, final isolated products were further processed by quality control, neutralization, and sterile filtration prior to being administered to patients. Standard quality control procedures including TLC, HPLC and measurement of pH value are conducted.

Briefly, this exemplary example discloses, among other things, a high-yielding and cost-effective microfluidic synthetic platform that can be easily adaptable to clinical environment in synthesis of $^{68}$Ga-PSMA for molecular imaging and $^{177}$Lu-PSMA for targeted therapy. The microfluidic device demonstrated many desirable characteristics by enabling preparation of diverse radiopharmaceuticals in a fast, efficient and cost-effective manner. Without the need of any additional procedures, isolated final products were in superior compliance with QC requirements, thus allowing for direct administration to patients. Notably, achieving radiosynthesis of highly demanded $^{68}$Ga-PSMA and $^{177}$Lu-PSMA in a low-cost fashion represent a significant advancement towards the realization of personalized medicine.

Example 2

Microfluidic Device for Rapid and Efficient
Production of Radiotracer [$^{18}$F]Fallypride The first human use of a [$^{18}$F]fallypride tracer produced by a microfluidic batch-reactor has been reported recently. However, while this recent report did use a microfluidic chip as microreactor for the fluorination step, the fluoride concentration subsystem utilized a commercial ion-exchange cartridge (off-chip), and final purification step was accomplished via conventional HPLC (also off-chip), thereby missing the opportunity of integrating all steps of the production within a single, compact microfluidic chip. Although there has been exciting progress employing microfluidic technology for PET tracer synthesis, most efforts focus primarily on the investigation of a single step in the process (mostly on-chip radiosynthesis), leaving other essential steps, such as concentration of the [$^{18}$F]fluoride mixture and radiotracer product purification, to be performed off-chip.

Figure 9:
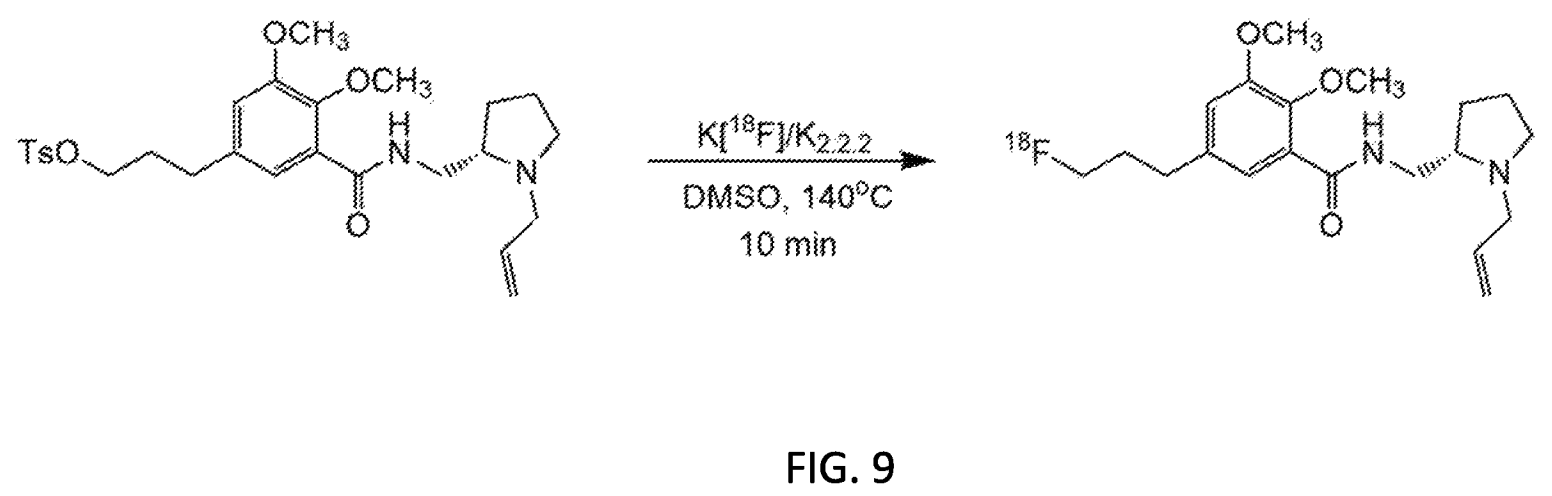

In this exemplary example, a simple microfluidic system is disclosed, which integrates several modules on a single chip to accomplish all principal steps for radiotracer production. To demonstrate the utility of this microfluidic chip, [$^{18}$F]fallypride, a widely used radiotracer in PET imaging, is synthesized starting with [$^{18}$F]fluoride retrieved from a nearby cyclotron shown in FIG. 9. Instead of relying on complicated on-chip flow control components that require multiple levels of lithography and feature alignment (e.g., elastomer valves formed via aligned multilayer PDMS), the invention in some embodiments employs simple off-chip mechanical valves to provide convenient and reliable control of reagent transfer between various modules. The invention also uses an on-chip ion-exchange column that is capable of concentrating a quantity of fluoride sufficient for several human doses. In some embodiments, the invention employs an on-chip cavity that facilitates rapid drying and enables subsequent fluorination reaction. However, unlike previous efforts where HPLC or commercial $C_{18}$ cartridges were utilized for purification of the final product, the invention employs an on-chip $C_{18}$ column that is integrated with the previous modules. It is noteworthy that the microfluidic chip, incorporating all the on-chip modules for [$^{18}$F]fally-pride radiotracer production, is low-cost and disposable, allowing an operator to use a fresh chip for each on-demand PET radiotracer production run. The flow control elements, e.g., but are not limited to, syringe pumps and mechanical valves, can be easily cleaned using ethanol or other appropriate solvents and are thus reusable. Using this microfluidic device, a small shielded space composed of several lead bricks would satisfy the requirements for radiation shielding, eliminating the need for a standard hot cell. Moreover, further automation of the pumps and valves could accelerate the entire process and shorten the overall synthesis time period, minimizing the loss of imaging reagents due to the decay of radionuclides. Variation of either the solid phase extraction (SPE) material or the elution methodology could allow our microfluidic platform to produce additional radiotracers. To adapt this microfluidic chip to a clinical setting, further development of the purification method is also required to achieve sufficient chemical purity. With excellent throughput, radiochemical purity and disposability, the invented microfluidic system represents a viable means to facilitate the production of radiotracers on demand and promote both the distribution and use of PET technology.

Device Fabrication

In this exemplary example, a microfluidic device, "RAPID" (Radiopharmaceuticals As Precision Imaging Diagnostics) platform/system, is developed. The RAPID platform utilizes a polydimethylsiloxane (PDMS) microfluidic chip with a chamber microreactor that is used to produce the tracer [$^{18}$F]fallypride of sufficient quality for PET imaging, where reaction processes occur on-chip with reagent delivery reliant on off-chip syringe pumps and valves. The RAPID platform is constructed using PDMS and borosilicate glass, and each of the three main steps for [$^{18}$F] fallypride production has a designated area, i.e., a designated module. [$^{18}$F]Fluoride trapping and release is located in a designated concentration column filled with an ion exchange resin/beads with trapping and release of the fluoride controlled by the solvent. The chamber microreactor (reaction cavity) is a small hole covered with a thin PDMS layer to enable fast and reliable solvent evaporation without the loss of radiation. Following the reaction, the reaction products are run through a $C_{18}$ column (purification column) to initiate purification, allowing for the removal of some reaction byproducts and unreacted [$^{18}$F]fluoride.

Specifically, the microchannel pattern is fabricated using facilities within the cleanroom affiliated with the Vanderbilt Institute of Nanoscale Science and Engineering (VINSE). A laser writer (Heidelberg μPG 101) is utilized to create patterns on a silicon wafer using an about 60 μm thick layer of mr-DWL 40 resist. Then, liquid PDMS (Sylgard 184, part A and part B mixed in 10:1 ratio and degassed) is poured onto the resist-patterned silicon wafer located in a petri dish to produce an about 1 cm thick layer. After curing in an oven (Thermo Scientific Lindberg/Blue M) at about 65° C. for about 12 h, the PDMS layer is peeled off the resist mold, and holes are punched at the inlet and outlet of the microchannels using an about 1.5 mm internal diameter punch (Ted Pella). The patterned PDMS layer, along with a substrate such as a glass microscope slide (Fisher Scientific, Premium Plain Glass Microscope Slides), is exposed to an oxygen plasma (Harrick Plasma, PDC-001) for about 60 seconds. Then, the two plasma-treated surfaces are bonded together and baked on a hot plate at about 60° C. for about 1 h before use. Next, the top surface of the microfluidic chip and an about 0.2 mm thick PDMS film with an about 1.5 mm size hole in the center are plasma treated again. The PDMS film is aligned such that the hole on the PDMS film is located at the center of a reaction cavity, and subsequently bonded to the top of the reaction cavity. A coned NanoPort assembly (IDEX, N-333) is aligned and placed on the top of the PDMS layer. Well-mixed PDMS is used as an adhesive and applied on the edge of the coned assembly, and then baked in an oven at about 65° C. for about 2 hours, such that the NanoPort is firmly attached to the top of the PDMS film. The microbore tubing (about 0.02" ID and about 0.06" OD) is purchased from Cole-Parmer and inserted directly into the PDMS layer without using any tubing connectors. The average length of tubing used between the chip and the external valves is about 5 cm. In all experiments, the microfluidic chip, hot plate and syringe pump are set inside a hot cell and the syringe is switched and reconnected for loading different reagents and $N_2$ behind the hot cell.

In this exemplary embodiment, the microfluidic chip is formed of a patterned PDMS layer on a glass slide/substrate. It should be appreciated that the microfluidic chip can be formed of any suitable materials, for example, a patterned layer on the top of a non-patterned polymer layer/substrate or a non-patterned glass slide/substrate, or an etched glass slide on the top of a non-patterned polymer layer/substrate or a non-patterned glass slide/substrate. The polymer can be any polymer in addition to PDMS.

Figures 10A, 10B, 10C, 10D:
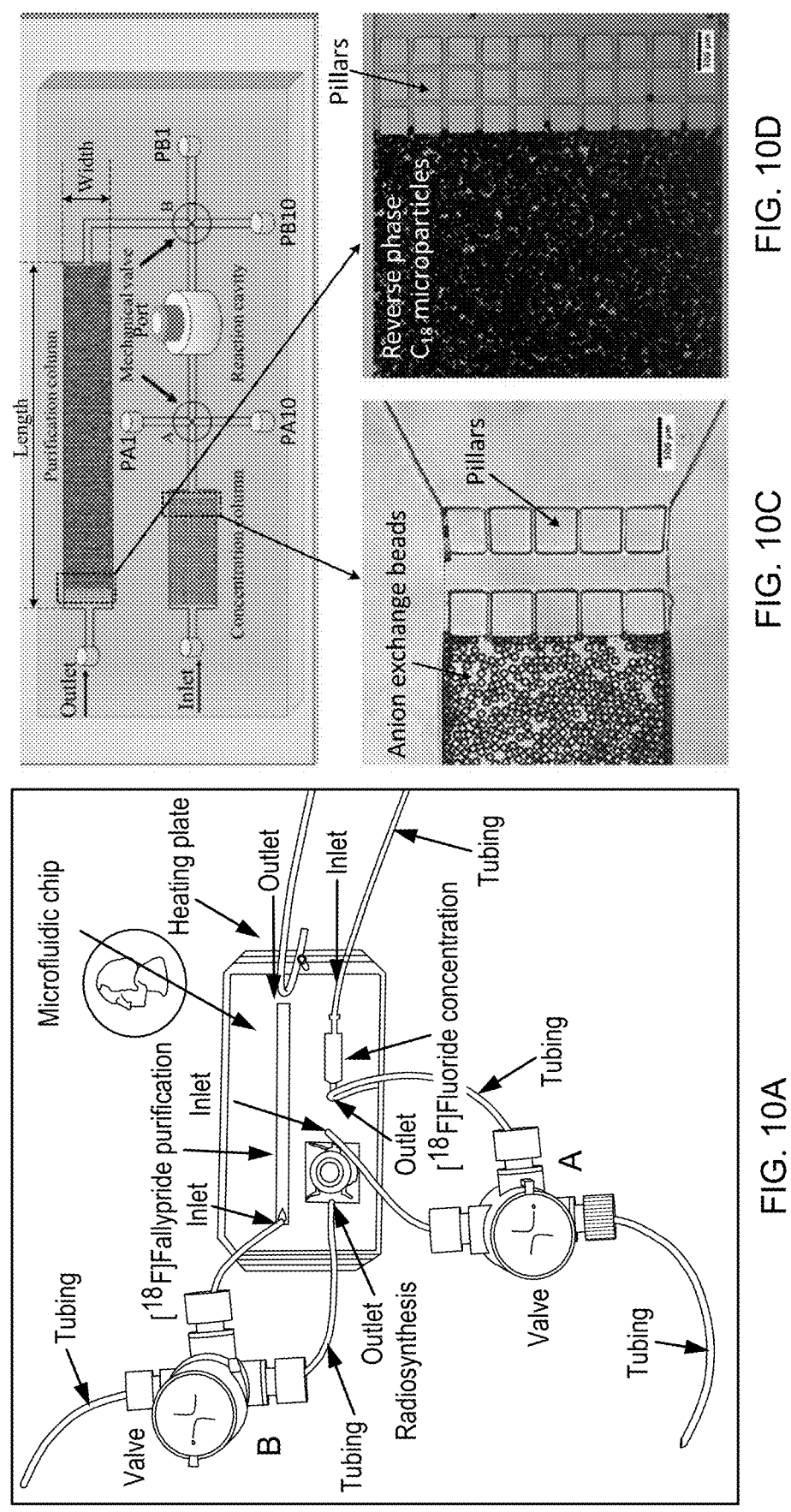
FIG. 10A shows a photograph of the microfluidic chip according to one embodiment of the invention, with an American twenty-five cent coin placed above.
FIG. 10B shows a schematic illustration of the microfluidic chip employed for $[^{18}$F]fallypride production, including a $[^{18}$F]fluoride concentration column, fluorination reaction cavity and $[^{18}$F]fallypride purification column, according to one embodiment of the invention.
FIG. 10C shows a photograph of anion exchange beads trapped inside a microchannel by about 10 μm gap PDMS pillars, according to one embodiment of the invention.
FIG. 10D shows a photograph of reverse phase $C_{18}$ microparticles trapped inside a microchannel with about 40 μm gap PDMS pillars, according to one embodiment of the invention.

FIGS. 10A-10D show a schematic illustration and images of the microfluidic chip used for fallypride synthesis according to some embodiments of the invention. As shown in FIGS. 10A-10B, the microfluidic chip device includes three main modules: a concentration column (module), a fluorination reaction cavity (chamber) and a purification column (module) that serve to concentrate the diluted [$^{18}$F]fluoride mixture, perform the heat-assisted fallypride fluorination reaction and purify the synthesized [$^{18}$F]fallypride, respectively.

In some exemplary embodiments, the on-chip concentration column (i.e., concentration module) is about 5 mm in width, about 10 mm in length and about 60 μm in height. Anion exchange beads (Source 15Q, GE healthcare) are packed into the concentration column by introducing an about 20% ethanol solution containing suspended beads into the concentration microchannel through the inlet of the concentration microchannel. The desired quantity (about 3 μl) of anion exchange beads is trapped by a double or triple row of square PDMS pillars with about 10 μm gap near the outlet of the concentration microchannel to form the desired column therein, as shown in FIG. 10C of a photograph of anion exchange beads trapped inside the concentration microchannel by about 10 μm gap PDMS pillars. Then, the anion exchange beads are activated using about 1.0 M of $KHCO_3$ (potassium hydrogen carbonate, about 0.2 ml) followed by flushing with about 0.5 ml DI water (18 MCI, Milli-Q Integral ultrapure water).

In some exemplary embodiments, the central reaction cavity (i.e., reaction chamber) is fabricated using an about 8 mm inner diameter punch (Ted Pella). The coned NanoPort assembly (IDEX, N-333) is placed on the top of the PDMS layer and aligned with the punch thereon. As the microfluidic chip device has an about 1 cm thick PDMS top layer, the maximum volume allowed inside the reaction cavity is about 500 µl.

In some exemplary embodiments, the fallypride purification column (i.e., purification module) is prepared using the same technique used to form the concentration column, inserting a triple row of square PDMS pillars with about 40 µm gap near the outlet of the purification microchannel. Silica gel (Fisher Scientific, Acros Organics, size 40-63 µm), suspended in pure ethanol, is introduced through the inlet of the purification microchannel, and is trapped inside to form the desired column. The dimension of the fallypride purification column is about 4.8 cm in length, about 4 mm in width and about 60 µm in height, allowing about 7.2 µl (about 20 mg) silica gel to be packed inside. The purification column is activated before the experiment by flowing about 0.5 ml DI water through it. FIG. 10D is a photograph showing reverse phase $C_{18}$ microparticles trapped inside the purification microchannel with the square PDMS pillars with about 40 µm gap.

In some exemplary embodiments, off-chip mechanical valves, e.g., valves A and B (Upchurch Valves, V-100D), as shown in FIGS. 2A-2B, are used to control the transit of reagents among these three modules. A syringe pump (New Era Pump Systems, NE-300, not shown herein) is used to control flow of the various reagents. A hot plate (IKA, Control-VISC), as shown in FIG. 10A, placed under the microfluidic chip is used to heat the entire device during solvent evaporation and fluorination reaction steps.

In other embodiments, on-chip valves such as on-chip rotary planar valves (RPV), and/or on-chip pump such as on-chip rotary planar peristaltic micropump (RPPM) can also be utilized to control the transit of reagents among these three modules, and flow of the various reagents.

Reagents and Materials

In the exemplary examples, [¹⁸F]Fluoride ion was obtained by cyclotron (GE Healthcare PETtrace 880) irradiation of [¹⁸O]-enriched water. Anhydrous acetonitrile (MeCN, about 99.8%), anhydrous methanol (MeOH, 99.8%) were purchased from Sigma Aldrich and used without further purification. Fallypride precursor was purchased from ABX Chemicals (Dresden, Germany). $K_{222}/K_2CO_3$ eluting solutions was prepared in the mixture of about 250 mg of $K_{222}$ dissolved in about 6 ml acetonitrile and about 140 mg of $K_2CO_3$ in DI water. All experiments were performed in compliance with the Vanderbilt University Medical Center policy on animal use and ethics, and complied with the relevant national/international guidelines (AAALAC-accredidation, United States). These studies were approved by the Vanderbilt Institutional Care and Use Committee (IACUC).

Analytical Facilities

In the exemplary examples, a Hitachi HPLC (LaChrom Elite, Pump L-2130) equipped with a wavelength UV detector (L-2400) and inline radiation detector (Inline Carroll & Ramsey) was used for radiochemical analysis. A Phenomenex $C_{18}$ column (Luna 5 µm C18(2) 100 Å LC Column 250×4.6 mm) was utilized and the flow rate of isocratic mobile phase of about 55% ethanol and about 45% 15 mM $Na_2PO_4$ buffer was about 0.9 ml/min. Total radioactivity was measured using calibrated dose calibrators (Capintec, CRC-25PET).

Microfluidic Chip Operation

Figures 11A, 11B, 11C, 11D, 11E, 11F:
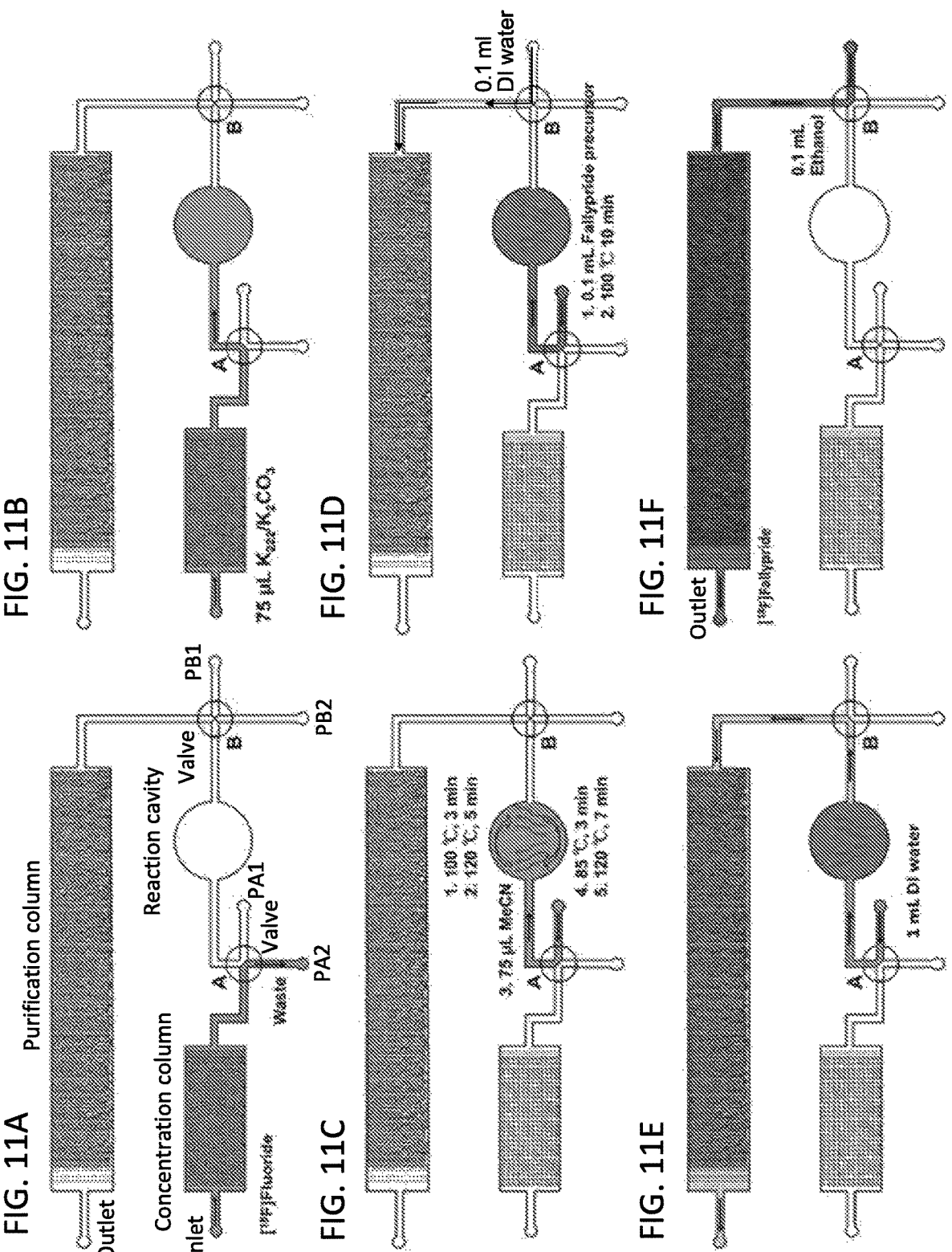
FIGS. 11A-11F shows a schematic representation of the steps used for the production of [$^{18}$F]fallypride on the integrated microfluidic chip, according to one embodiment of the invention. The six steps shown are.

FIGS. 11A-11F illustrates the steps for fallypride radiosynthesis on the microfluidic chip according to some embodiments of the invention. Radioactive [¹⁸F]fluoride in [¹⁸O]-enriched water was obtained immediately after cyclotron irradiation. Unless noted elsewhere, the amount of radioactivity used in in these exemplary experiments was about 30 mCi in about 0.1 ml irradiated target wash water. As shown in FIG. 11A, the [¹⁸F]fluoride mixture was introduced into the inlet of the on-chip concentration column using the syringe pump with an about 30 µl/min loading rate followed by about 0.1 ml of air at a loading rate of about 50 µl/min allowing all liquid to be pushed through the tubing connection and the concentration column. The liquid coming out from the concentration column was collected in a glass vial at port PA2 fluidically connecting valve A, and typically contained a negligible amount of radioactivity (less than about 2 µCi), i.e., waste. The radioactivity of the initial [¹⁸F]fluoride loading, captured inside the concentration column, and the [¹⁸F]fluoride residue left in the syringe were measured separately via a dose calibrator. The efficiency of the concentration column was calculated after accounting for the decay of the radioisotope.

Figure 15B:
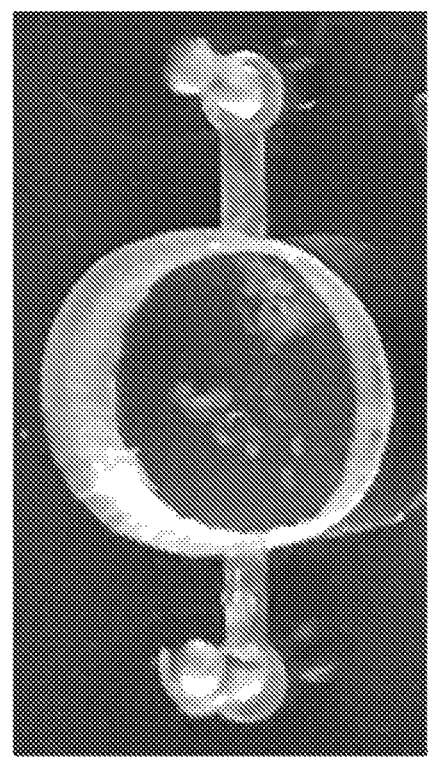
FIG. 15A-15B are photographs of on-chip reaction cavity with no reagent inside (FIG. 15A) and after water evaporation (FIG. 15B), according to one embodiment of the invention.

To release the captured [¹⁸F]fluoride inside the concentration column, about 75 µl of $K_{222}/K_2CO_3$ eluting solution was injected into the inlet of the concentration column at an about 30 µl/min loading rate, as shown in FIG. 11B. At the same time, the mechanical valve A, fluidically connected between the concentration column and the reaction cavity (batch reactor), was set to direct the released reagent into the reaction cavity. Another 0.1 ml air was injected from the inlet of the concentration column to push all the remaining liquid into the reaction cavity. Because the fluorination reaction requires anhydrous conditions shown in FIG. 11C, the microfluidic chip was first placed on a hot plate at about 100° C. for about 3 minutes and then at about 120° C. for about 5 minutes. The heated water inside the reaction cavity evaporated through the about 1.5 mm hole on the top. The microfluidic chip was then removed from the hot plate for about 2 minutes, allowing the entire chip to cool down below the boiling point of acetonitrile. To completely remove residual moisture inside the reaction cavity, about 75 µl anhydrous acetonitrile (MeCN) was loaded from the inlet (denoted as PA1 in FIG. 11A) of the reaction cavity and the entire microfluidic chip was placed on another hotplate at about 85° C. for about 3 minutes, and then at about 120° C. for about 7 minutes. Constant $N_2$ flow at about 0.2 psi was applied through the inlet (via port PA1 of valve A) of the reaction cavity to facilitate the removal of residual moisture during the entire evaporation process. After these drying steps, solid residue was observed at the bottom of the reaction cavity (FIG. 15B). The on-chip radioactivity after evaporation was measured and the loss of radioactivity was less than about 5%.

After achieving the anhydrous conditions necessary for fallypride fluorination, about 0.1 ml dimethyl sulfoxide (DMSO) containing fallypride precursor (about 3 mg), vortex-mixed for about 30 minutes in advance, was injected from the inlet (via port PA1 of valve A) of the reaction cavity and the reaction cavity was immediately sealed by screwing in a male nut (Fisher Scientific) into the NanoPort, minimizing the loss of radioactivity during the fluorination process. As shown in FIG. 3D, the microfluidic chip was heated at about 100° C. for about 10 minutes to produce the radioactive fallypride. The successful synthesis of [¹⁸F]

fallypride was validated via radio-HPLC analysis, the radioactive peak eluting at about 11~12 minutes matching the reference standard.

To obtain chemically pure [$^{18}$F]fallypride suitable for PET imaging, the crude production material was purified using a column containing monodiperse $C_{18}$ stationary phase. Before transferring all liquid through the on-chip purification column, about 0.1 ml DI water was loaded from the inlet (via port PB1 of valve B) of the purification column to fully rinse the $C_{18}$ gel. Subsequently, valve A was closed and the valve B was open, creating unidirectional flow from the reaction cavity to the purification column, as shown in FIG. 11E. The flow rate produced by the syringe pump was about 50 µl/min. The tight seal of the reaction cavity provided by the male nut allowed the synthesized compound to be injected into the purification column without leakage. Undesired compounds, including unreacted fallypride precursor, any remaining [$^{18}$F]fluoride, and various by-products were thereby pushed off-chip, only leaving the desired [18F]fallypride trapped on-chip. Next, as shown in FIG. 11E, another 1 ml DI water was loaded from the inlet (via port PA1 of valve A) of the reaction chamber and passed over the reaction chamber to totally remove unreacted [$^{18}$F]fluoride ion, which would lower the overall radiochemical purity and confound imaging procedures. Finally, trapped [$^{18}$F]fallypride was eluted off of the chip using about 0.1 ml pure ethanol and collected in a glass vial at the outlet of the purification column, as shown in FIG. 11F.

Results and Discussions

[$^{18}$F]Fluoride Concentration: According to the invention, to synthesize [$^{18}$F]fallypride or other radiotracers with the microfluidic chip, the first critical step is to concentrate [$^{18}$F]fluoride that is provided as a diluted solution in [$^{18}$O]-enriched water. In this exemplary study, PDMS pillars are employed to form physical barriers near the end (outlet) of the concentration microchannel, thus trapping desired anion exchange microparticles inside the concentration column. FIG. 10C shows an optical image of anion exchange beads packed inside the concentration column. Experimental results listed in Table 4 suggested that the on-chip concentration column can accomplish efficient enrichment of a sufficient quantity of [$^{18}$F]fluoride with minimal radioactivity loss, comparable or better than performance achieved with a commonly used purification cartridge (Waters Sep-Pak QMA).

TABLE 4

The relationship between the volume of anion exchange beads inside the concentration column and the radioactivity trapped on the microfluidic chip. All listed values are decay-corrected to the time point of initial radioactivity in the syringe.

| Volume of beads (µl) | Initial syringe radioactivity (mCi) | Final syringe radioactivity (mCi) | Waste vial radioactivity (mCi) | Radioactivity trapped on chip(mCi) | Efficiency |
|---|---|---|---|---|---|
| 0.62 | 10.3 | 0.6 | 0.9 | 8.93 | 90.1% |
| 0.62 | 8.7 | 0.6 | 0.7 | 7.5 | 92.2% |
| 0.62 | 35.8 | 1.8 | 12.6 | 21.5 | 65% |
| 0.62 | 39.1 | 1.5 | 14.3 | 20.9 | 59.7% |
| 3 | 95.7 | 0.34 | 0.01 | 93.0 | 97.7% |
| 3 | 128.6 | 4.8 | 0.1 | 123.0 | 95.9% |

As expected, the maximum quantity of [$^{18}$F]fluoride that is captured by the concentration column was related to the volume of anion exchange beads packed inside the microchannel. Considering that the goal of the microfluidic chip is to synthesize multiple doses of radiotracer sufficient for human imaging, the on-chip concentration module, must be capable of capturing radioactivity in the range of about 100 mCi (3700 MBq). To determine the relationship between the volume of anion exchange resins and the captured radioisotope, several versions of ion exchange columns with varying dimensions were fabricated. Raw [$^{18}$F]fluoride with radioactivity values as high as about 130 mCi (4810 MBq) was then loaded into each column to evaluate the trapping efficiency and determine the optimal dimension. Table 5 summarizes the results of these exemplary experiments. It turned out that about 3 µl (about 10 mg) of anion exchange resin captured over about 100 mCi [$^{18}$F]fluoride with the efficiency near about 98% over a loading period of about 6 minutes. However, a reduced timespan may be achieved with additional optimization of column geometry (i.e., wider microchannel) to allow higher reagent loading rate.

Solvent Exchange: To release the captured [$^{18}$F]fluoride from the concentration column, about 75 µl of $K_{222}$/$K_2CO_3$ solution was introduced into the anion exchange column channel, after which the released solution was directed to the reaction cavity. During reagent transfer process, valve A and valve B were set in the fashion shown in FIG. 3B to minimize the liquid stuck in the tubing connection. In the attempt to reduce the overall synthesis time, the volume of $K_{222}$/$K_2CO_3$ eluting solution required to fully release all [$^{18}$F]fluoride off the concentration column was optimized. In this system, a large portion of the production time is devoted to achieving a completely anhydrous state prior to the synthesis reaction, and thus optimizing the volume of eluting solution helps promote the overall production efficiency and minimizes the decay of radioisotope. The release efficiency with various volumes was compared and the results indicated that about 75 µl of the $K_{222}$/$K_2CO_3$ was the optimal amount for releasing [$^{18}$F]fluoride with radioactivity loss less than about 5%, as listed in Table 5.

TABLE 5

The relationship between the volume of $K_{222}$/$K_2CO_3$ used for releasing trapped [$^{18}$F]fluoride off the concentration column and the releasing efficiency. The efficiency is calculated accounting for the decay of the radionuclide over time.

| Volume of $K_{222}$ (µl) | On-chip radioactivity (mCi) | Released radioactivity (mCi) | radioactivity left on-chip (mCi) | Efficiency |
|---|---|---|---|---|
| 50 | 7.5 | 4.8 | 1.7 | 74% |
| 50 | 4.6 | 3.58 | 0.94 | 77% |
| 75 | 4.25 | 3.84 | 0.23 | 95% |
| 100 | 6.2 | 5.48 | 0.1 | 98% |

Figure 15A:
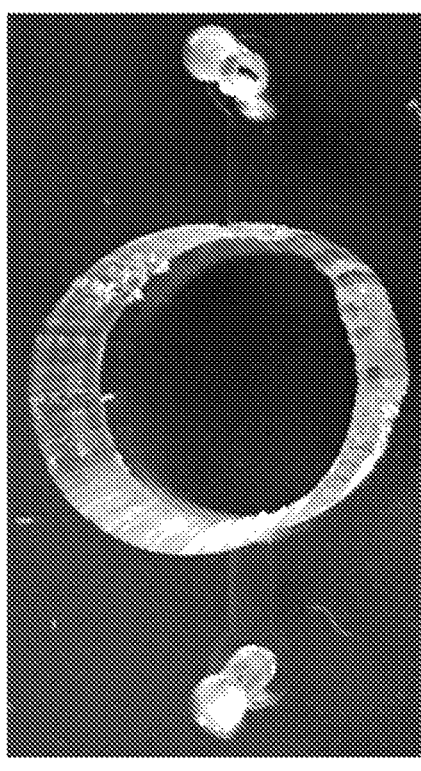

To achieve anhydrous conditions inside the reaction cavity, the entire chip was placed on a hotplate and a temperature gradient (about 100° C. for about 3 minutes and about 120° C. for about 5 minutes) was set, instead of direct heating at extremely high temperature, to avoid violent boiling, which could result in the liquid splashing out from the upper hole. A slow nitrogen flow was introduced via the inlet (via port PA1 of valve A) of the reaction cavity (FIG. 11C) to facilitate the evaporation process. After the first round of heating, azeotropic distillation was employed by injecting about 75 µl anhydrous MeCN into the reaction cavity (FIG. 11C) to completely remove any remaining moisture. In conventional macroscopic radiotracer production, 2-3 cycles of azeotropic distillation are typically performed to guarantee an anhydrous environment. In contrast, using the microfluidic platform according to the invention, only one cycle of azeotropic distillation is sufficient to enable the subsequent nucleophilic substitution reactions, thus shortening the required production timeframe. FIGS. 15A-15B are photographs of the on-chip reaction cavity with no reagent inside (FIG. 15A) and after water evaporation (FIG. 15B), where the solid salt was deposited on the bottom of the reaction cavity after evaporation.

Figure 12:
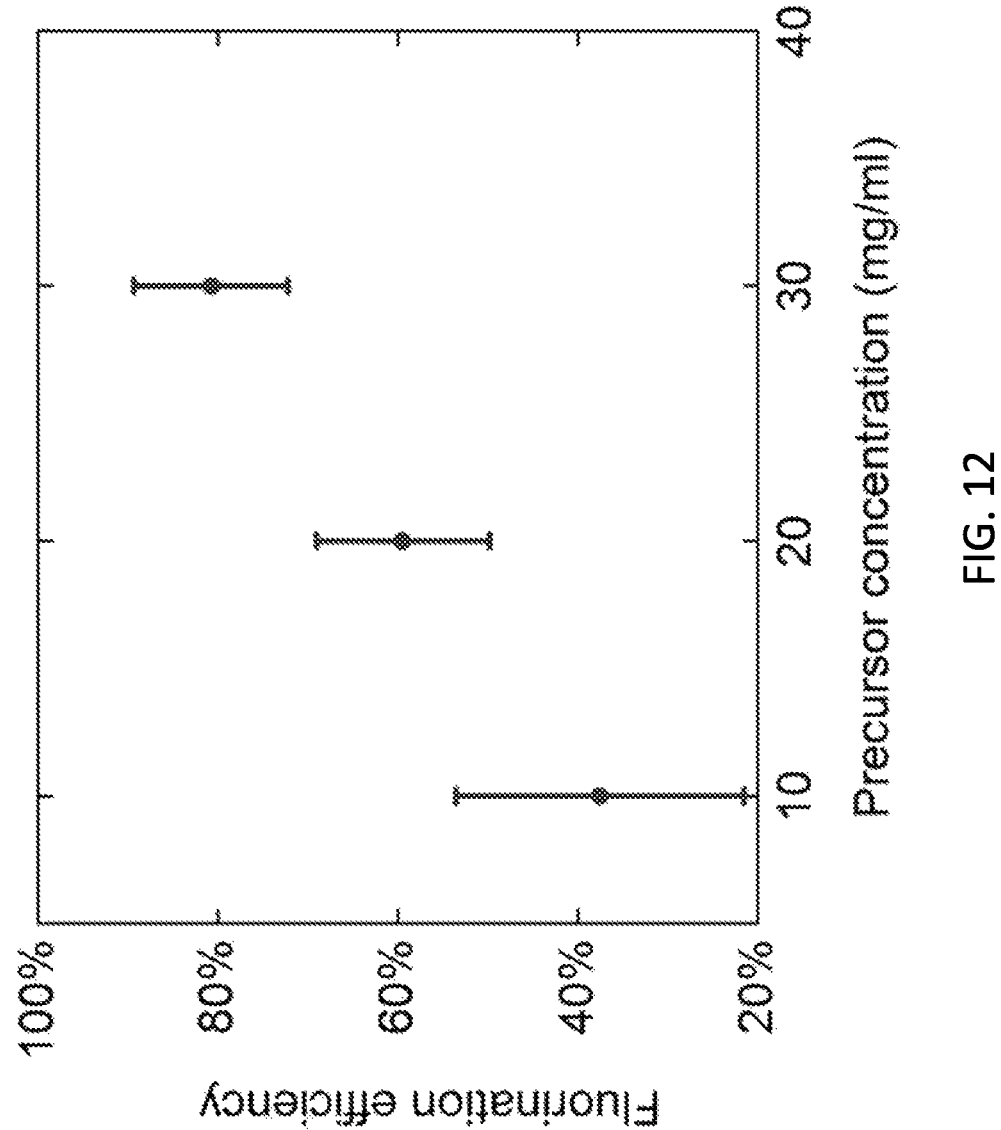
FIG. 12 shows the relationship between precursor concentration and fluorination efficiency, according to one embodiment of the invention.
Figures 13A, 13B:
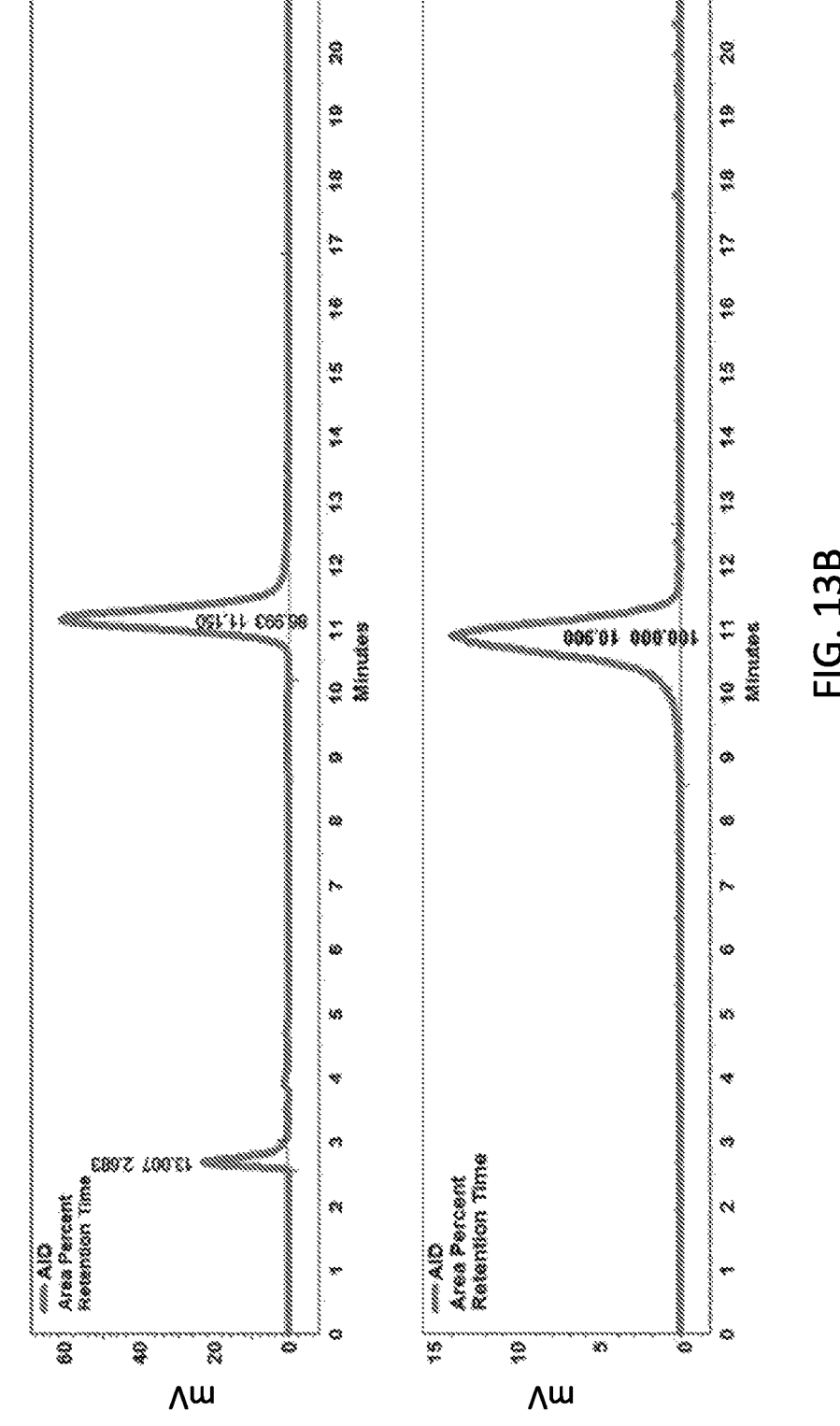
FIG. 13A shows crude radio-HPLC of [$^{18}$F]fallypride synthesized inside the reaction cavity, according to one embodiment of the invention.
FIG. 13B shows radio-HPLC of [$^{18}$F]fallypride eluted from the on-chip purification column, according to one embodiment of the invention.
Figure 14A:
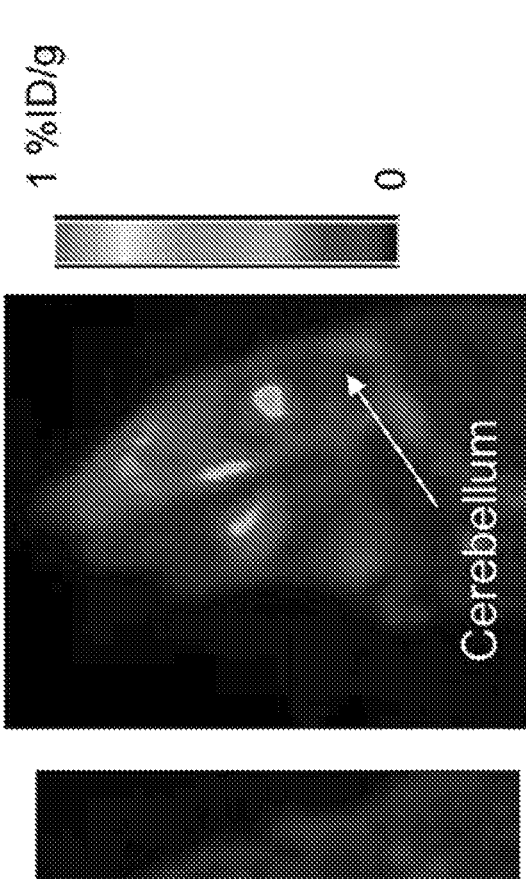
FIG. 14A shows PET image of rat brain using [$^{18}$F] fallypride produced in a microfluidic chip, according to one embodiment of the invention.
Figure 14A:
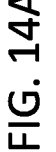
Figure 14A:
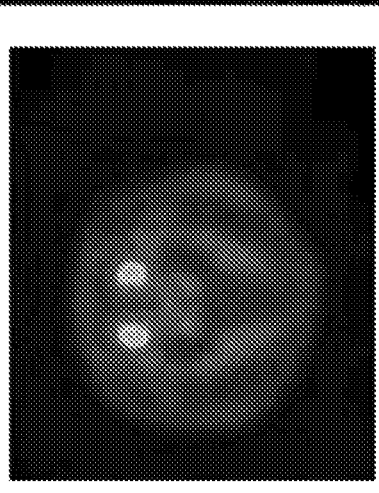
Figure 14B:
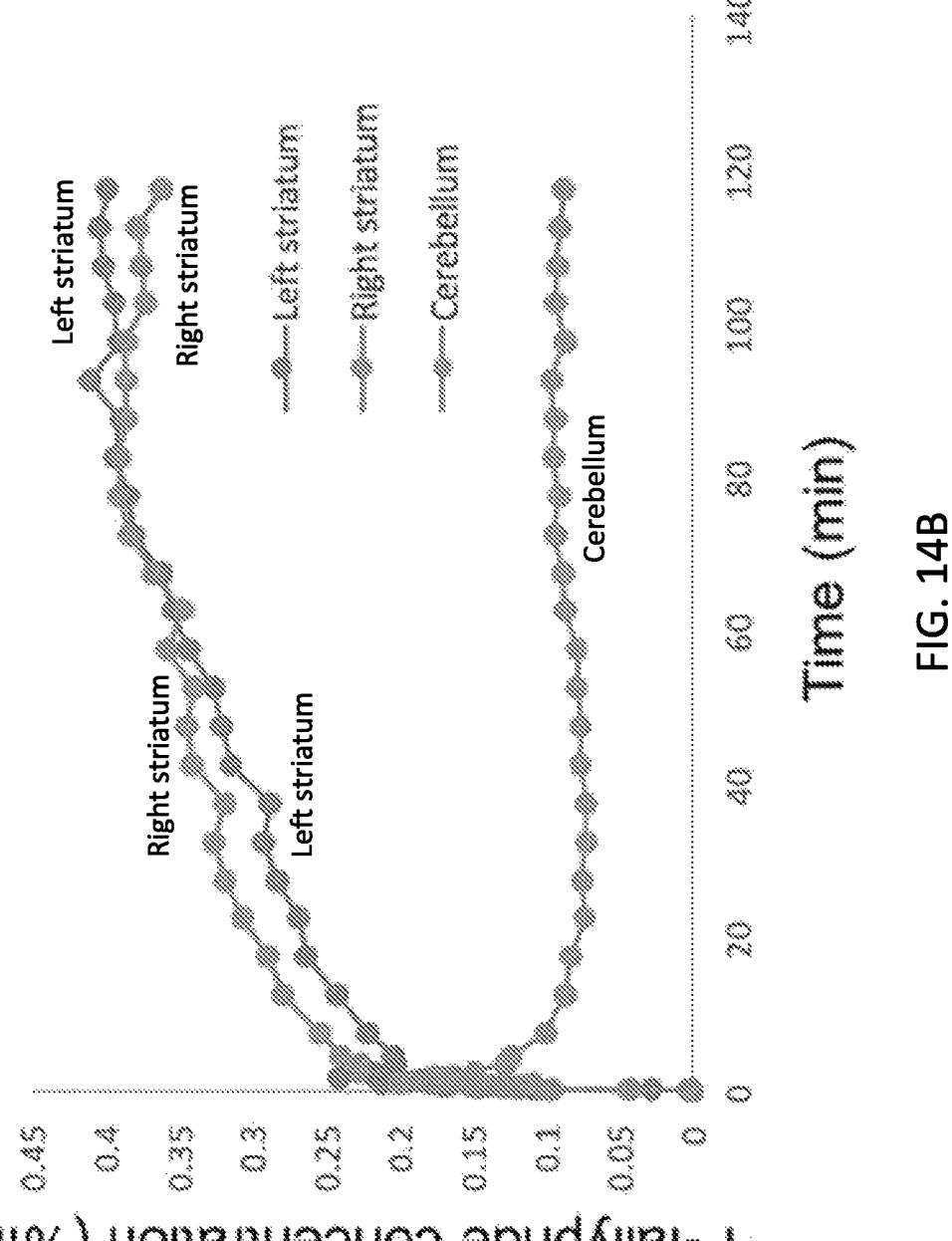
FIG. 14B shows the variation of [$^{18}$F]fallypride concentration imaged in the microPET for 2 hours, according to one embodiment of the invention.

Fluorination Reaction: The fluorination reaction is performed after introducing the fallypride precursor (FIG. 11D), dissolved in a polar aprotic solvent, into the reaction cavity containing the concentrated, dried fluoride-kryptofix complex. Instead of employing a low-boiling-point solvent, such as acetonitrile, the fallypride precursor was dissolved in dimethyl sulfoxide (DMSO) and loaded into the reaction cavity. Though acetonitrile has been widely used in clinical production and has the benefit of being easily removed later, the required temperature for nucleophilic substitution reactions with [$^{18}$F]fluoride (usually around 100° C.), exceeds the boiling point of acetonitrile, which would increase the pressure inside the sealed cavity and possibly lead to leakage. Employing the high boiling point solvent DMSO avoids these issues. Based on a report by Javed et al., the concentration of fallypride precursor plays a significant role in final crude radiochemical yield in a batch microfluidic reactor. To optimize the yield of [$^{18}$F]fallypride in the microfluidic chip according to the invention, the relationship between the concentration of fallypride precursor and the overall conversion efficiency was further investigated. Similar to previous reports, a rise of fluorination efficiency was observed as the concentration of fallypride precursor increases, as shown in FIG. 12. The successful synthesis of [$^{18}$F]fallypride was confirmed via HPLC analysis (FIG. 13A). The result indicated that the labeling efficiency during fluorination process was about 87%, higher than what can be typically obtained using conventional automated methodologies.

Figures 16, 17:
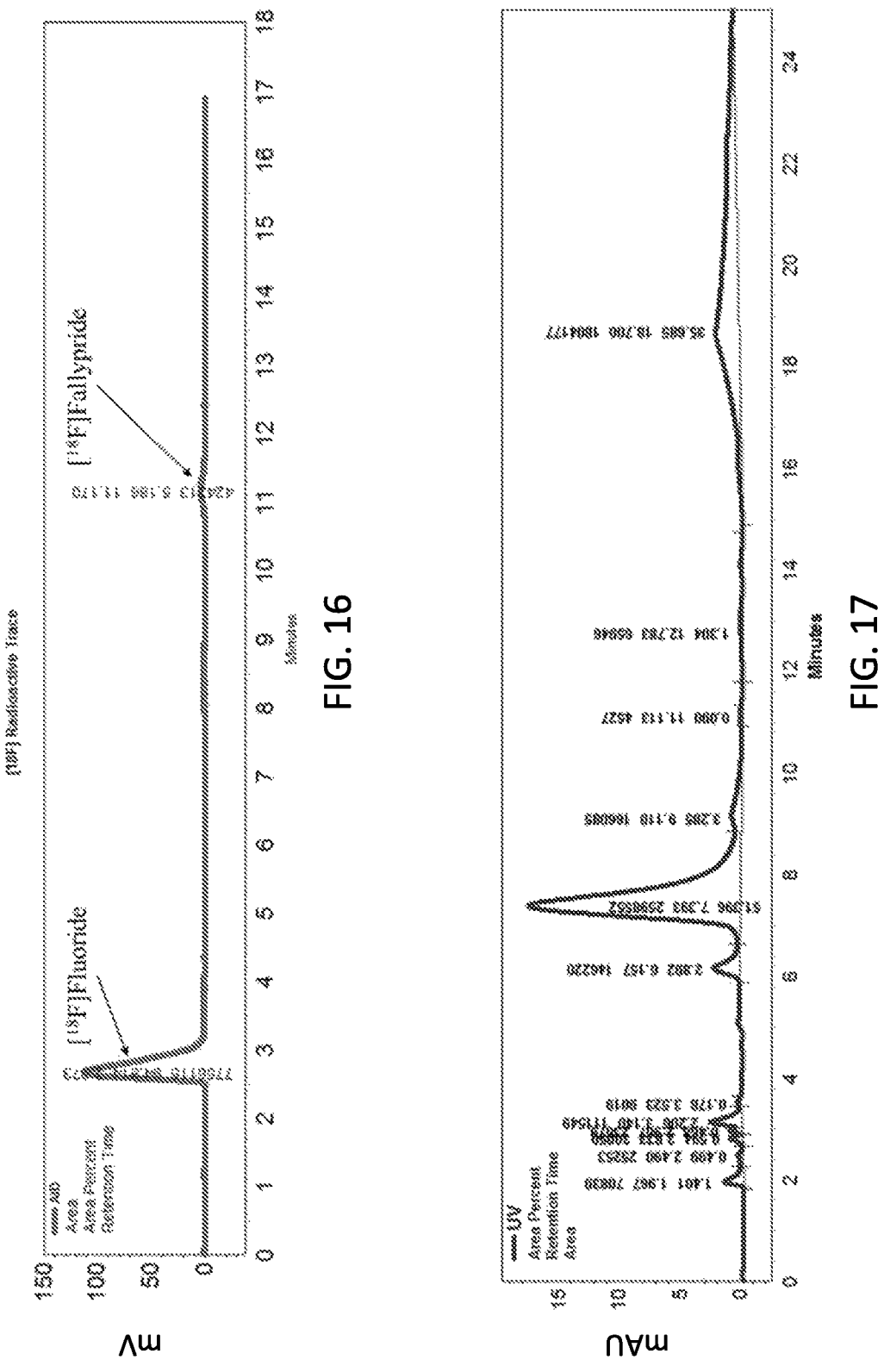
FIG. 16 shows a radio-HPLC analysis of the waste mixture passed through the $C_{18}$ column, according to one embodiment of the invention. This injection was taken using the mixture solution flowing out from the purification column after labelling reaction. 95% [$^{18}$F]fluoride was washed off the purification column, and only 5% [$^{18}$F]fallypride was lost at this step.
FIG. 17 shows an UV spectrum for the purified [$^{18}$F] fallypride, according to one embodiment of the invention, showing product peak at 11.11 min. The presence of minor impurities is observed throughout the spectrum.

[$^{18}$F]Fallypride Purification: After the fluorination reaction, the product exists in a solution containing unwanted quantities of unreacted [$^{18}$F]fluoride, K$_{222}$, and other undesired byproducts. Thus, the crude [$^{18}$F]fallypride mixture must be purified. This is accomplish using an integrated on-chip purification column. The purification column was fabricated in a manner identical to the concentration column. FIG. 10D shows an optical image of silica gel packed inside the purification microchannel forming the purification column. After the fluorination reaction, the hot microfluidic chip was allowed to cool down to approximately room temperature. Meanwhile, 0.1 ml DI water was loaded through the purification column to fully activate the reverse phase C$_{18}$ (FIG. 11D). Next, 1 ml DI water was injected at the inlet of the reaction cavity (FIG. 11E), pushing the reacted solution (with the products in DMSO) through the purification column. To minimize any potential loss of [$^{18}$F]fallypride, the volume ratio of DMSO to water was tuned to 1:10 such that it was able to carry all crude radiochemical mixture in the reaction cavity but did not wash the captured [$^{18}$F]fallypride off the on-chip purification column. HPLC analysis of the outlet waste indicated negligible [$^{18}$F]fallypride loss during this step (FIG. 16).

Finally, the trapped [$^{18}$F]fallypride was released by injecting about 0.1 ml pure ethanol into the inlet of purification column. FIG. 13B shows radio-HPLC analysis of the eluted [$^{18}$F]fallypride, which exhibited 100% radiopurity.

The overall radiochemical yield (RCY) (10±3%, n=5) is calculated as the ratio of the decay-corrected radioactivity of the resulting [$^{18}$F]fallypride released off the chip, divided by the initial radioactivity of [$^{18}$F]fluoride loaded into the microfluidic chip (trapped by the on-chip concentration column). The radioactivity of the [$^{18}$F]fluoride loaded into the microfluidic chip was measured by placing the whole chip in a dose calibrator. The average radioactivity used for those productions was about 50 mCi and the volume of anion exchange beads and reverse phase C$_{18}$ was about 3.2 μl and about 7.2 μl, respectively. The whole process was completed in approximately 60 minutes starting from the loading of [$^{18}$F]fluoride to the collecting of purified [$^{18}$F] fallypride, which could likely be further shortened using automated external valves and programmable syringe pumps. As reported by Elizarov, PDMS may react with [$^{18}$F]fluoride ions, which might reduce the overall radiochemical yield. To reduce this loss, in certain embodiments, the inner walls of the microchannels are coated with an inert layer, and in another embodiments, the chip fabrication material is modified.

To further verify the utility of the resulting [$^{18}$F]fallypride, we produced (using the integrated microfluidic chip) a dose of about 300 μCi with about 19.55 Ci/μmol (723.35 GBq/μmol) of specific activity and about 98.62% of radiochemical purity, and obtained PET data from a rat brain. The time point used to calculate the specific activity was at the end of production, namely the time when the purified [$^{18}$F]fallypride was retrieved from chip. The rat was brought to the imaging lab to habituate about 3 hours prior to imaging. About 0.1 ml purified [$^{18}$F] fallypride was filtered through an about 0.45 μm filter (Millex-HV) and about 0.9 ml saline was added to formulate the PET probe used for rat injection. FIG. 6A shows PET images of rat brain using [$^{18}$F]fallypride produced in a microfluidic chip, and FIG. 6B shows the variation of [$^{18}$F]fallypride concentration imaged in the microPET for about 2 hours. The accumulation and pharmacokinetics of [$^{18}$F]fallypride were as expected when evaluated in the rat brain. A typical UV spectrum, indicating some observable chemical impurities, is given in FIG. 17. Though the chemical purity has been dramatically improved from the crude product mixture, further purification is needed.

A general performance comparison to previously reported results from other platforms (including information regarding fluorination efficiency, purification method, synthesis time, resulting dose amount, specific activity and overall radiochemical yield) is summarized in Table 6. The invented microfluidic platform exhibits comparable performance in terms of fluorination efficiency and specific activity. Further optimization and automation of various operational parameters may increase the overall radiochemical yield and reduce the entire synthesis time.

TABLE 6

Operational performances of our microfluidic platform compared to several reported
results based on microfluidic [18F]fallypride production. All efficiencies and yields are
calculated based on decay-corrected values

| Publication | Lu et al. | Chen et al. | Lebedev et al. | This invention |
|---|---|---|---|---|
| Starting [18F]fluoride | 0.5-2.5 mCi | Not reported | 370 mCi | About 50 mCi |
| Fluorination efficiency | Up to 88% | 65 ± 11% (n = 6) | Not reported | 80 ± 8% (n = 4) |
| Purification method | HPLC | No | HPLC | On-chip module |
| Dose amount | 0.5-1.5 mCi | Not reported | About 27 mCi | About 3 mCi |
| Specific activity | Not Reported | 19 Ci μmol$^{-1}$ | Not reported | 19.55 Ci μmol$^{-1}$ |
| Overall RCY | Not Reported | Not Reported | 37 ± 5% | 10 ± 3% |
| Synthesis time | About 50 min | About 31 min | About 45 ,im | About 60 min |
| PET imaging | No | No | Human | Rat |

In terms of disposability, the microfluidic chip may be discarded after each PET tracer production once any residual on-chip radioactivity has decayed to a safe level. Off-chip flow control components, such as pumps and mechanical valves, may be cleaned using ethanol or other appropriate solvents, and are thus reusable.

In some embodiments, a heating and fluid flow control system (micro-controller, solenoid valves, remote control pump system, etc.) are fully automated, which enables PET probe production to run without the need for operator intervention at every step.

Briefly, in this exemplary example, a simple, economic and efficient microfluidic platform to aid both radiochemistry research efforts and clinical efforts by rapidly producing ultrapure radioactive fallypride on demand. This highly integrated configuration enables all essential steps needed for [18F]fallypride production without any off-chip treatment, starting from reaction reagents and ending with a purified product. These disposable chips may allow high throughput investigations of novel radiotracer chemistry, as well as the mass-production of established PET tracers. By using this microfluidic device, we envision that clinicians may overcome a significant bottleneck imposed by limited access to an onsite cyclotron, as they could easily utilize delivered radionuclides and produce imaging reagents as needed without relying on centralized facilities. The integration of this microfluidic device within current clinical environments would be a relatively straightforward task, and serve as a solution to the high cost of standard radiopharmaceutical production. Though further development of the purification method for [18F]fallypride is still needed, replacing packing materials inside each column may make this microfluidic platform suitable for the production of other PET tracers.

Example 3

Microfluidic Platform with Enhanced
Reproducibility Via on-Chip Heating

In this exemplary example, certain engineering approaches are employed to enhance the reproducibility and ease-of-use of the RAPID platform by employing an integrated on-chip heater and resistive temperature detector (RTD) to enable closed-loop control of reaction temperature to better than +/−1° C.

Figure 18C:
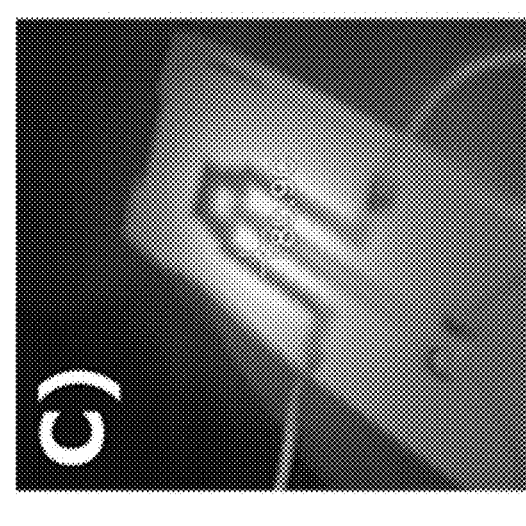
FIGS. 18A-18D show on-chip RTD and heater according to one embodiment of the invention.
Figure 18D:
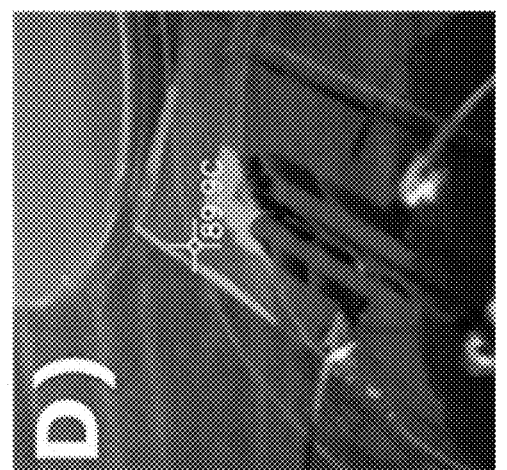
Figure 18A:
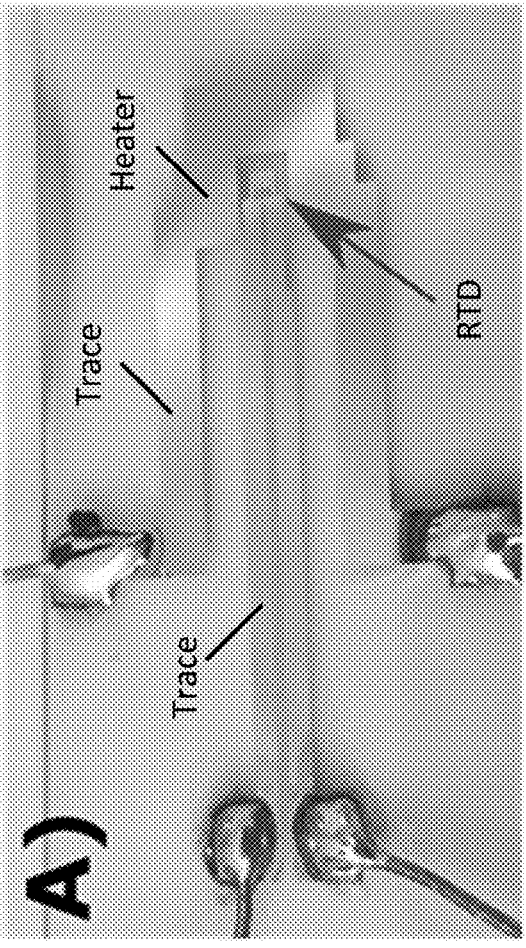
Figures 19A, 19B, 19C, 19D:
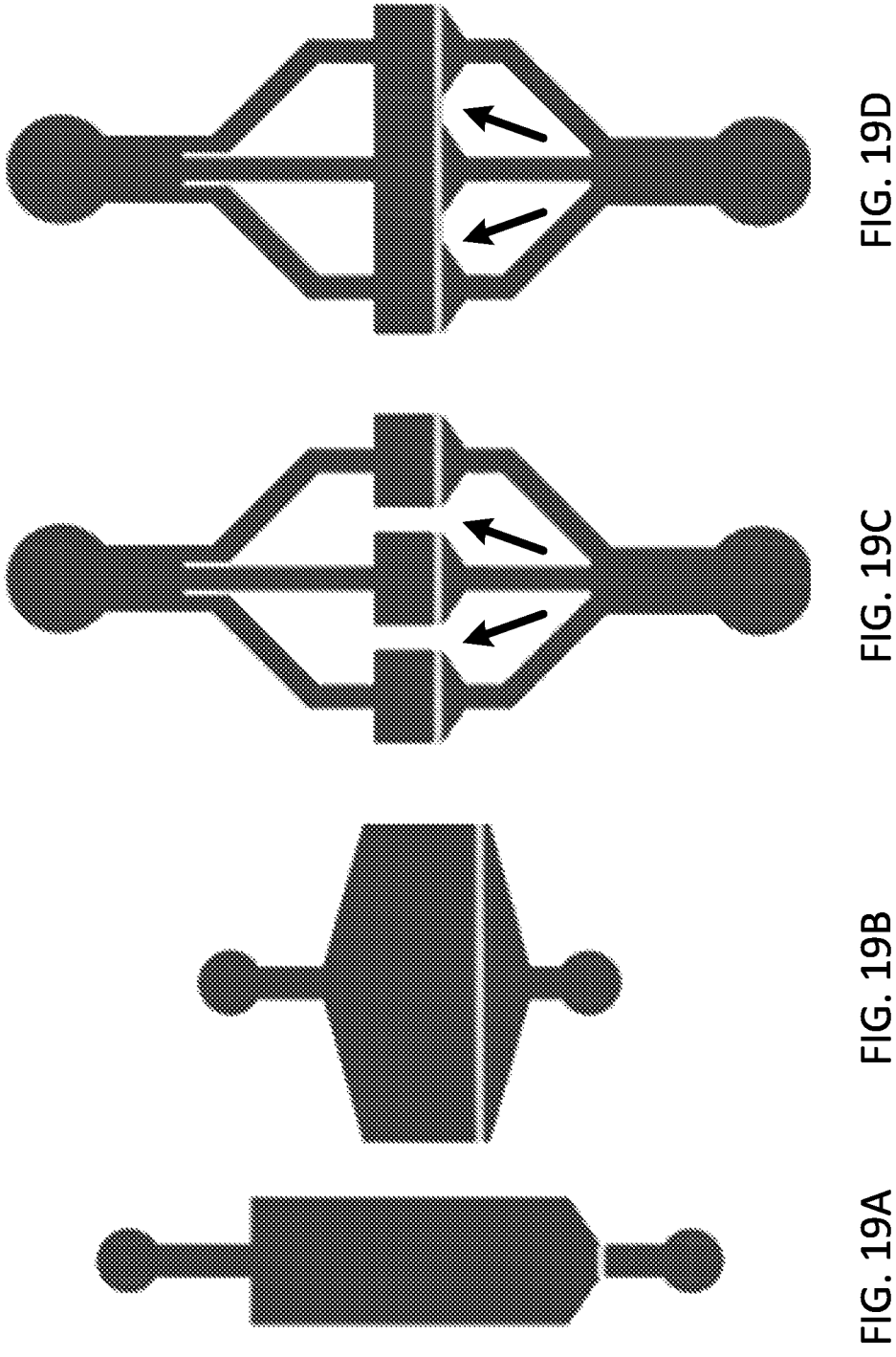
FIGS. 19A-19D show on-chip packed bed designs that enhance the flow rate according to embodiments of the invention.

Specifically, using standard photolithographic techniques, a resistive heater composed of platinum is patterned on a microscope slide. During the same process, a RTD, such as, but not limited to, a platinum RTD that is the most common type of RTD and often called P100 or P1000 depending on 0° C. resistance, is produced near the heater. FIG. 19A is an image of the on-chip heater and RTD. All traces are formed of platinum having a thickness of about 300 nm. To avoid contact between the metallic traces of the heater and RTD and the reactants to be heated, a thin layer of silica (about 50 nm) is deposited by sputtering with regions away from the heater and RTD masks to prevent deposition and enable electrical contact. In operation, the heater controllably heats the local chip temperature (on a microscope slide) to about 90° C., as demonstrated in FIGS. 18C-18D being respectively IR thermal and regular optical images of the on-chip heater and RTD in operation.

Figure 18B:
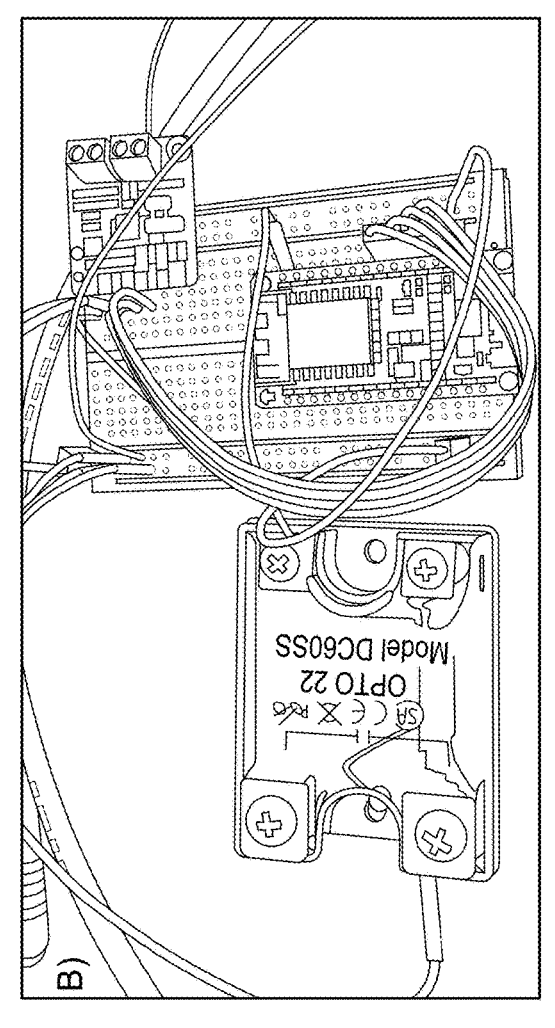

In addition, a microcontroller (e.g., but not limited to, NodeMCU board using an ESP8266 microcontroller chip with WiFi interface) is employed to read the temperature measured by the RTD (e.g., but not limited to, using the MAX31865 RTD sensor interface) and control a solid state relay (SSR) to rapidly connect or disconnect the on-chip heater from a power supply by using a well-established PID (proportional, integral, differential) library (a common approach to achieve tight process control). FIG. 18B shows one embodiment of such a microcontroller and associated hardware (MAX31865 and SSR) for providing PID-based closed-loop control of local temperature. Such architecture ensures to both control the temperature within about 1° C. and enable a wireless interface via a mobile device such as a smartphone.

To validate the performance of the on-chip heater and closed-loop control, a slab of PDMS with a hole punched out from the center (to form a reservoir) is placed on the microscope slide over the heater and RTD. The reservoir is filled with about 500 μL $H_2O$. The control circuit is set to maintain the water at various temperatures (e.g., 60, 70, 80° C.) and the temperature profile as measured by the RTD recorded. To demonstrate temperatures above 100° C., dimethylsulfoxide (DMSO, boiling point of 189° C.) is used. Once the temperature has reached the steady state, an IR thermometer (FLIR One Pro) is used to validate the temperature of the water in the reservoir. Consistent offsets and any other calibration issues can be easily accounted for by the PID algorithm and associated software. The PID algorithm is tuned (i.e., the P, I, and D gain values determined) by a standard autotuning algorithm (part of the PID library).

The reservoir of about 500 μL water can be controllably heated to a specific temperature using a closed loop control algorithm, in a range (for water) of about 35-90° C. with a tolerance of better than +/−1° C. Given the small thermal mass and local heating, the time required to heat from room temperature to the desired setpoint is less than about 60 seconds. The heating system is capable of maintaining this level of control up to at least 130° C. (as tested using DMSO).

It is possible that rapid, localized heating of the microfluidic device may cause the microscope slide on which it is formed to crack due to thermal shock. In this case, one can either slow the heating rate or pattern a larger heater to achieve a more uniform temperature profile across the entire glass slide, which will not impact any of the on-chip radiochemistry. In addition, if the silica protective layer proves problematic (cracking, pinholes, poor uniformity, poor adherence to the substrate), the device can be coated with parylene to prevent contact between the water and the metallic traces. Alternatively, a thin film of PDMS can be spin-coated over the metallic electrodes, and a micropatterned PDMS slab is bonded to that surface. In either case, masking is again used to prevent coating regions of the device (far from the heater and RTD) to be used for electrical contact. In some embodiments, these passivation layers may need to be reduced in thickness to allow better heat transfer between the heater/RTD and the liquid in the reservoir. Moreover, the microfluidic devices can be placed on a Peltier unit to heat (and cool) the chips as needed.

Example 4

Different Microfluidic Architectures for High Throughput Radiofluorination

While the above-disclosed [18F]-radiochemistry device demonstrates impressive on-demand [18F]Fallypride production capabilities, there are still several engineering hurdles that must be overcome to enable the RAPID platform/system to be used in the clinic for on-demand human dosage production of tracers with 18F chemistries. This exemplary study addresses the engineering limitations of the RAPID device to form a platform that is fast, reproducible, and can produce clinically relevant quantities of two important 18F-based tracers in a ready-to-use format.

As disclosed above, the on-chip packed beds are used to capture over about 100 mCi of 18F with over 95% efficiency, and release it with over 98% efficiency (starting with about 6.2 mCi captured). The flow rates used, however, were relatively small at about 30-50 μL/min, due to the high fluidic resistance of the packed beds and resulting pressures required, which led to capture and elution timeframes on the order of about 10 minutes, far too long for the envisioned high throughput production of multiple unique tracers achieved with this platform. To enable rapid processing of large quantities of radionuclide and precursors, several microfluidic architectures are implemented by utilizing two benchmarks: amount of radionuclide processed (i.e., amount of radioactivity) and speed with which a standard dosage can be produced (starting from radionuclide and precursor in separate vials, and ending with a ready-to-use product). As shown in FIGS. 19A-19D illustrating different architectures/embodiments of on-chip packed beds, each microfluidic architecture contains an equivalent mass of resin to determine which one provides the best combination of low fluidic resistance, high capture capability, and narrow band elution of captured concentrated radionuclide. FIG. 19A is a packed bed geometry as disclosed above, with frit at the bottom. FIG. 19B is an alternative embodiment that has an equivalent volume as that of FIG. 19A, but shorter and wider to reduce fluidic resistance. The concern here would be with uniform bead packing. FIG. 19C shows a architecture having three smaller chambers in parallel, leading to reduced fluidic resistance but more uniformity in each chamber. FIG. 19D shows a single chamber with three isolated inlets and outlets to yield enhanced packing uniformity and avoid unequal pressure between chambers. Arrows indicate differences between architectures of FIGS. 19C-19D.

Figure 20A:
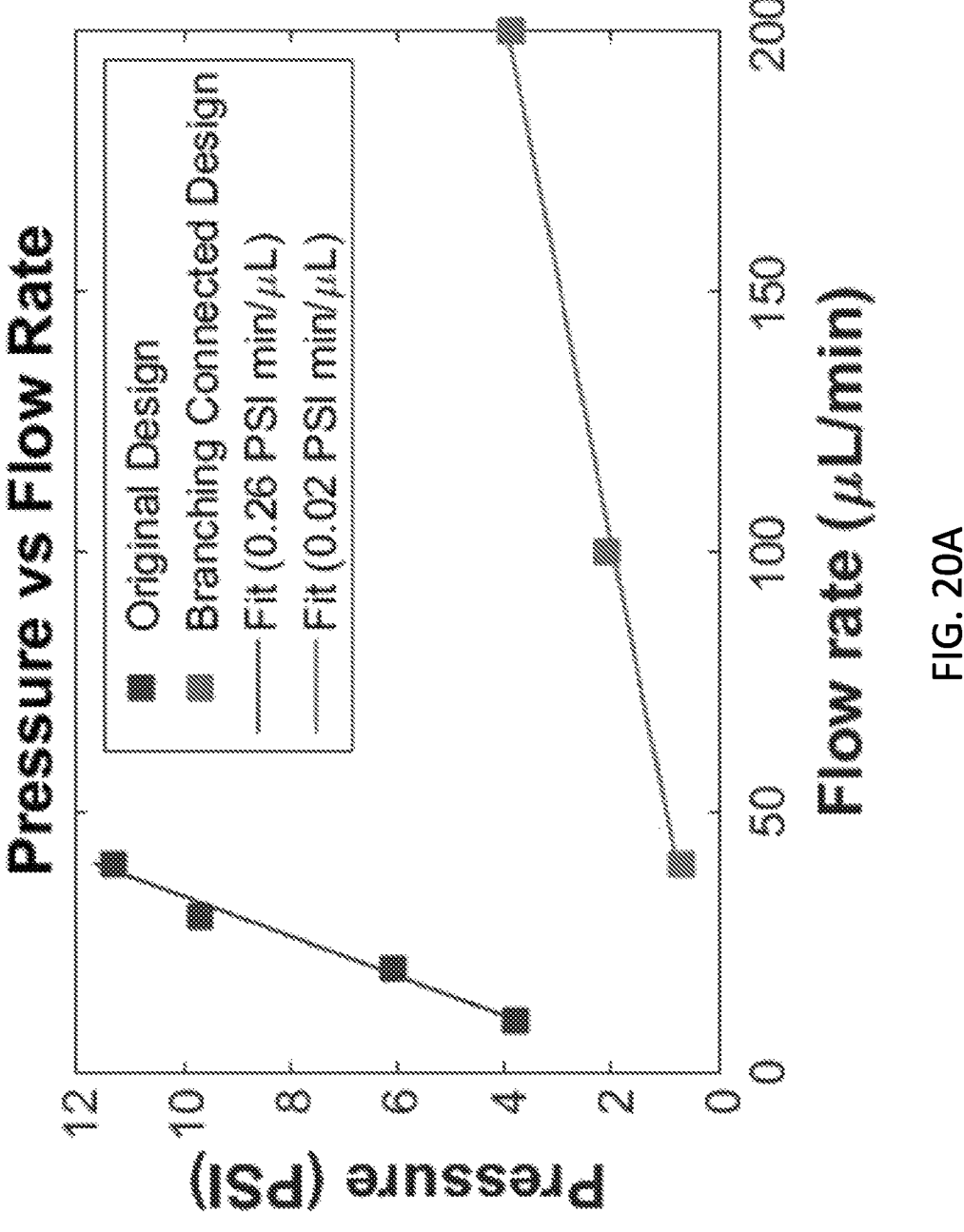
FIG. 20A shows fluidic resistance measurements for the design shown in FIG. 19A and the branching connected design shown in FIG. 19B of approximately equivalent volume of packed beads according to embodiments of the invention.
Figure 20C:
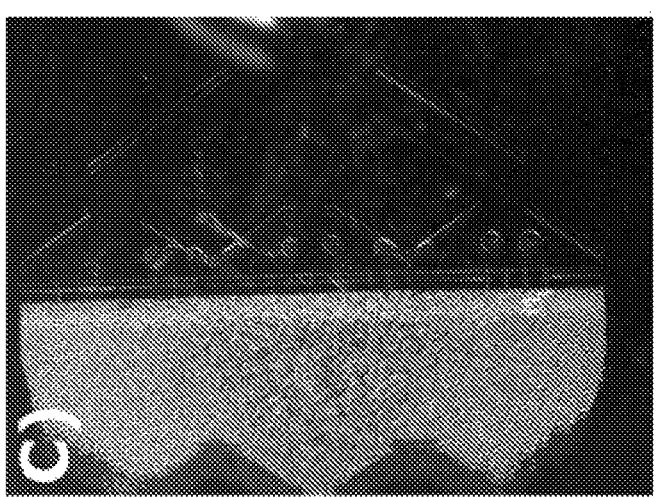
FIGS. 20B-20C are low magnification images of FIGS. 19A and 19B channel designs packed with SCX resin according to embodiments of the invention.
Figure 20B:
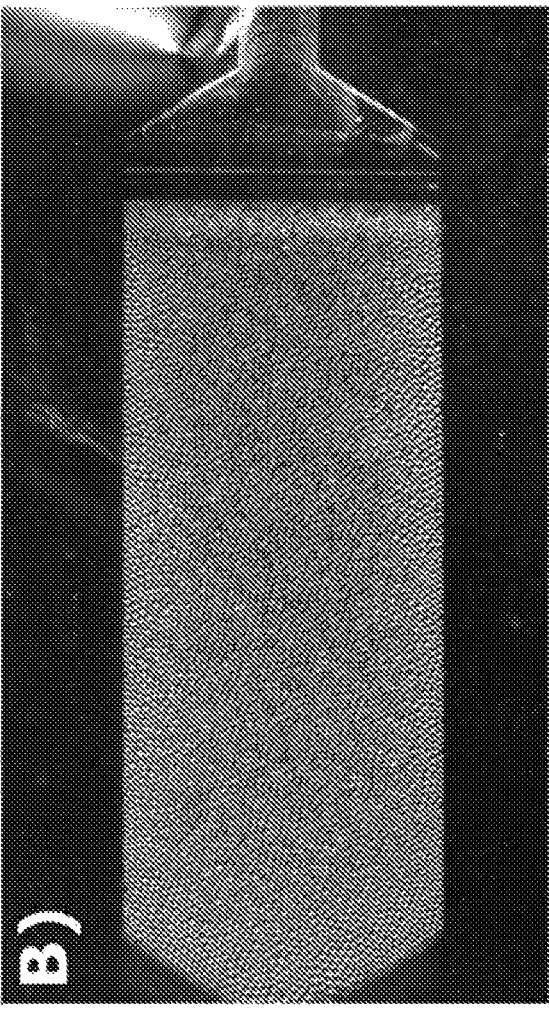

Fluidic resistance through each architecture is modeled using COMSOL and pore size and porosity of the packed beds are predicted. The results of these models using pressure (e.g., Honeywell 26PC flow through pressure sensor and Omega strain meter) and flow (e.g., Sensirion USB-interface flow-meter) meters to quantify fluidic resistance are experimentally validated, as shown in FIG. 20A. In some embodiments, chambers are packed with Maxi-Clean SCX resin (about 600 mg, particle size about 50 μm) by introducing suspensions in ethanol (about 5% w/v) at about 100 μL/min. After conditioning, capture and release uniformity are characterized using about 10 μM solution of Rhodamine B (in DI water) and fluorescence microscopy (to observe spatial variations in capture and ability to elute a narrow band of dye in about 100 μL of ethanol eluting solution) to determine the optimum design. The top three designs, as determined by low fluidic resistance, good trapping uniformity and high capture capability, uniform release in a narrow band, are subsequently packed with anion exchange resin (e.g., Source 15Q, GE healthcare) as described above and tested with [18F]fluoride in [18O]-enriched water from the cyclotron facility at VUMC. The fluidic architecture that functions best, as determined by lowest fluidic resistance while still capable of trapping at least 25 mCi and releasing at least 98% of the trapped activity in about 100 μL of eluting solution, is employed for all on-chip preconcentration columns. Similar processes are employed for on-chip purification columns as well. FIG. 20A is fluidic resistance measurements for the design shown in FIG. 19A and the branching connected design shown in FIG. 19B of approximately equivalent volume of packed beads. Pressure was measured at several flow rates and data was fit with a linear model to extract flow resistance. As fluidic resistance in a short, wide rectangular microchannel scales roughly as Length/Width, and the branching connected bed of FIG. 19B is three-time shorter and three-time wider than the design of FIG. 19A, one would expect a roughly 9-fold decrease in resistance. Experimentally, a 13-fold decrease in resistance was measured, which is not overly dissimilar from the predicted behavior. FIGS. 20B-20C are low magnification images of FIGS. 19A-19B channel designs packed with SCX resin.

For the optimized packed beds, a reduced preconcentration time less than 1 minute is required for to trap and release at least 25 mCi of 18F. The pressures required to achieve this performance is less than 15 PSI. The same concepts used to reduce fluidic resistance in the on-chip preconcentration column is employed for on-chip purification columns and similarly enable high purification performance combined with high flow rates (and thus short timeframes).

Alternatively, in some embodiments, in situ photopolymerized porous monoliths are used for the capture and/or purification columns, where porosity is optimized (e.g., by appropriate choice of porogens and monolith chemistry) to ensure both high capture and low resistance. Another route towards achieving higher flow rates and thus higher throughput is the ability to use higher pressure with these microfluidic devices. PDMS sealed to glass is capable of withstanding pressures up to about 70 PSI with appropriate plasma surface treatments. Instead of glass, silanized PMMA is used in some embodiments to roughly double the device failure pressure, where thermal bonding of embossed PMMA substrates yields an even higher bond strength. In addition, residence time is not a bottleneck in the process.

Example 5

Automated System for Customizable,
Dose-on-Demand Pet Radiopharmaceutical
Production To enable RAPID technology for widespread pre-clinical and clinical usage, it is critical to eliminate the need for a skilled human operator and instead transition to automated operation. Automation of tracer production provides several important benefits including cost reduction, enhanced reproducibility, higher speed, smaller footprint, and dramatically improved safety. Automation is also a key ingredient needed to enable the production of boutique tracers, as automated systems are far better able to switch between a variety of radiochemistries. While the core technology of the approach is the RAPID chip, an automated system built around the microfluidic chip enables the paradigm shift we are pursuing. By including remote control capabilities (via a WiFi or internet connection and scheduling software), a single RAPID platform is accessible to a large number of clinical users who simply need to request tracer production using a networked device (e.g., smartphone, tablet) and can expect the desired material to be available in a timely fashion.

Figure 21:
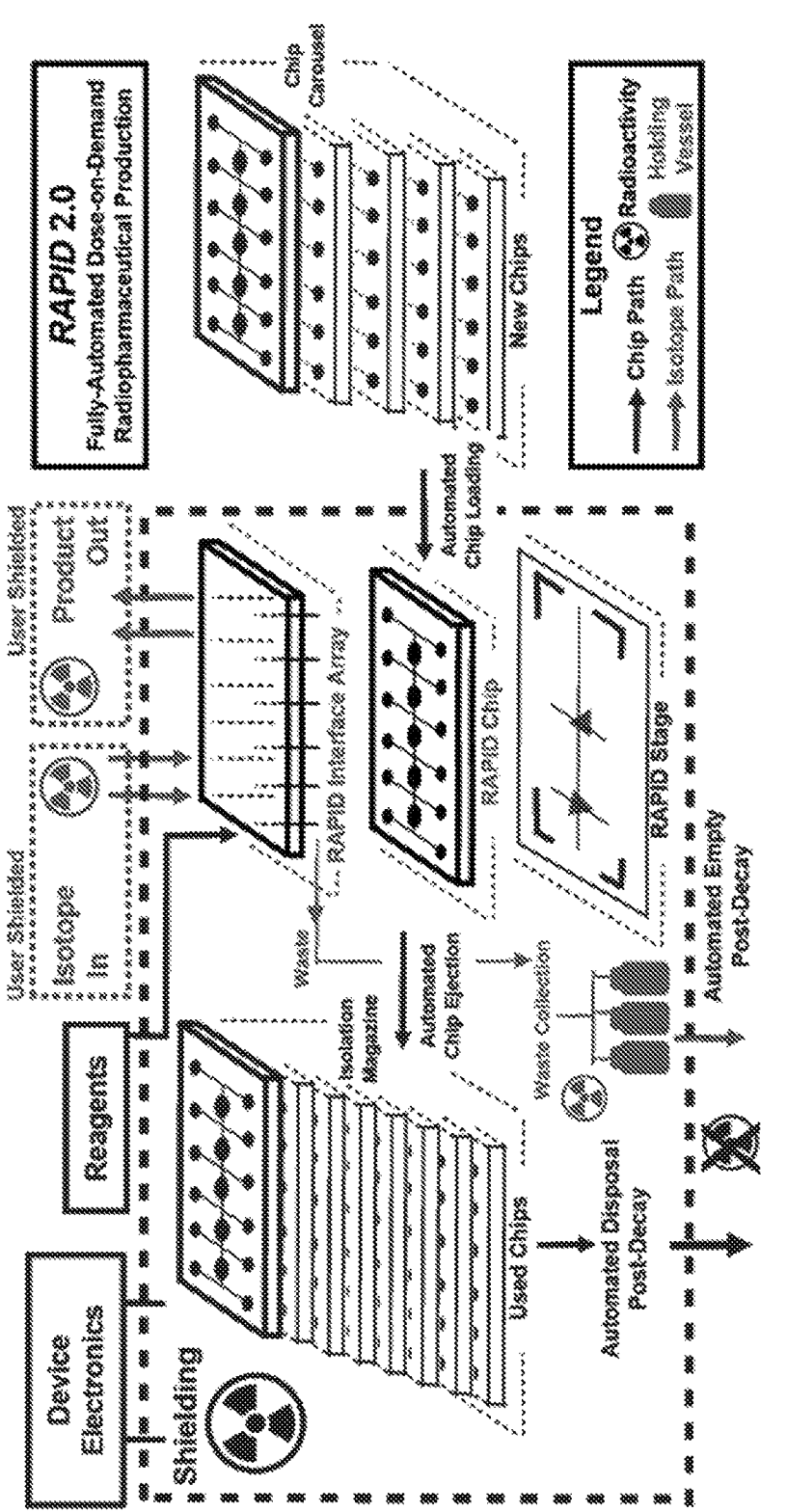
FIG. 21 shows schematic of automation platform to interface with multiple RAPID microfluidic devices and enable remotely scheduled dose-on-demand PET tracer production according to embodiments of the invention.

FIG. 21 shows a schematic overview of the envisioned automated platform according to one embodiment of the invention. All process control is performed using a microcontroller unit (MCU) such as a NodeMCU board. In one embodiment, the ESP8266 microcontroller runs standard Arduino code (a popular microcontroller platform with Java-like coding) and has built-in WiFi capabilities, which enables scheduling of automated tracer production from a mobile device such as a smartphone, as well as multiple general-purpose input and outputs (GPIO) ports, which can be expanded using I/O expanders such as the PCF8575. These GPIO ports are used to control solenoid valves, pumps, and other aspects of automated liquid handling systems, and can additionally interface to a wide range of sensors for process monitoring. In certain embodiments, Upchurch CV900-100 Compact Valves, which are extremely small and fast and have effectively zero dead volume, are used. Pumping is provided by custom built, microcontroller-controlled peristaltic pump platform for scheduled fluid handling. In certain embodiment, wash steps and gas purges between batches are employed to ensure cleanliness of the fluid paths (vales, tubing, etc.) and prevent cross-contamination. A robotic vial handling system is constructed so that it is possible to dispense specified dosages into multiple separate containers. Silicon photomultipliers interfaced to the process controller are employed at multiple critical locations to 1) monitor the amount of radioactivity captured in the on-chip concentration column, 2) ensure that purge steps adequately eliminate residual isotope in the apparatus tubing, 3) verify that used RAPID devices have undergone an adequate "cool-down" time period and no longer exhibit dangerous levels of radioactivity before they are ejected into a disposal bin, and 4) as part of an interlock system prohibiting users from opening the shielded box unless radiation levels are safe. Codes in the microcontroller keep track of the process timing (critical due to decay of the radionuclide) so that the activity in any given vial is known (i.e., each vial has a timestamp). Both fresh (unused) and waste (used) RAPID chips are housed in magazines handled by the robotic handling system developed. In certain embodiment, electrical contact to on-chip thermal control is made using pogo-pins. Reagents and isotopes are sourced from septum-sealed vials, with shielding in place as needed. According to some embodiments of the invention, the entire automated apparatus (capable of starting with radionuclide and precursors and resulting in ready-to-use human dosages) fits in a lead-lined box roughly the size of a mini-fridge.

Figure 22A:
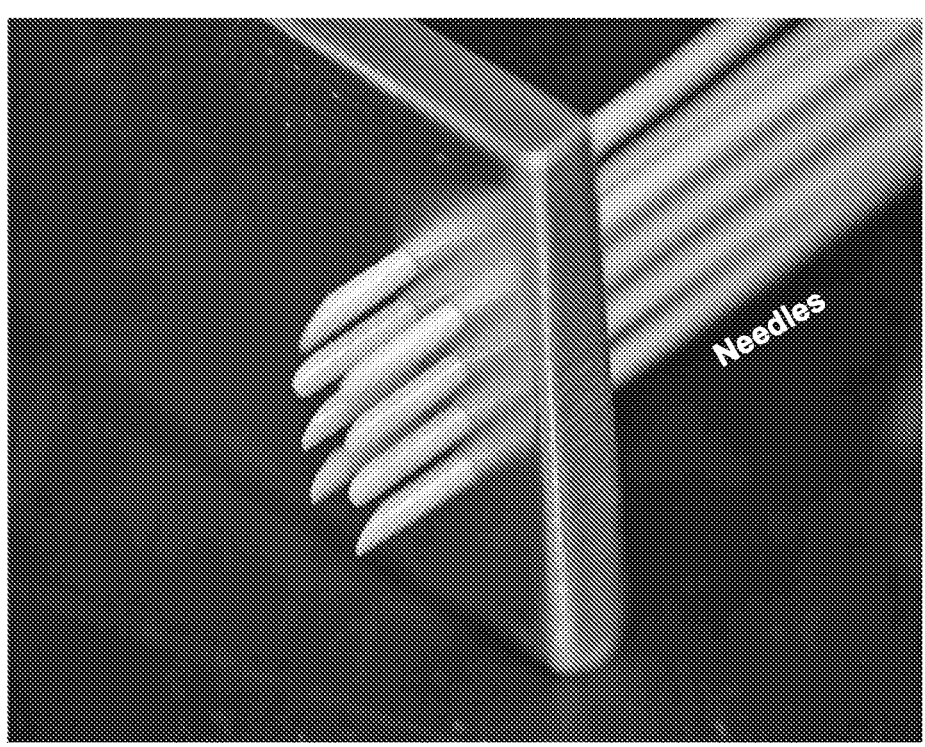
FIGS. 22A-22B show PEEK needle array multiplexed interconnect system according to embodiments of the invention.
Figure 22B:
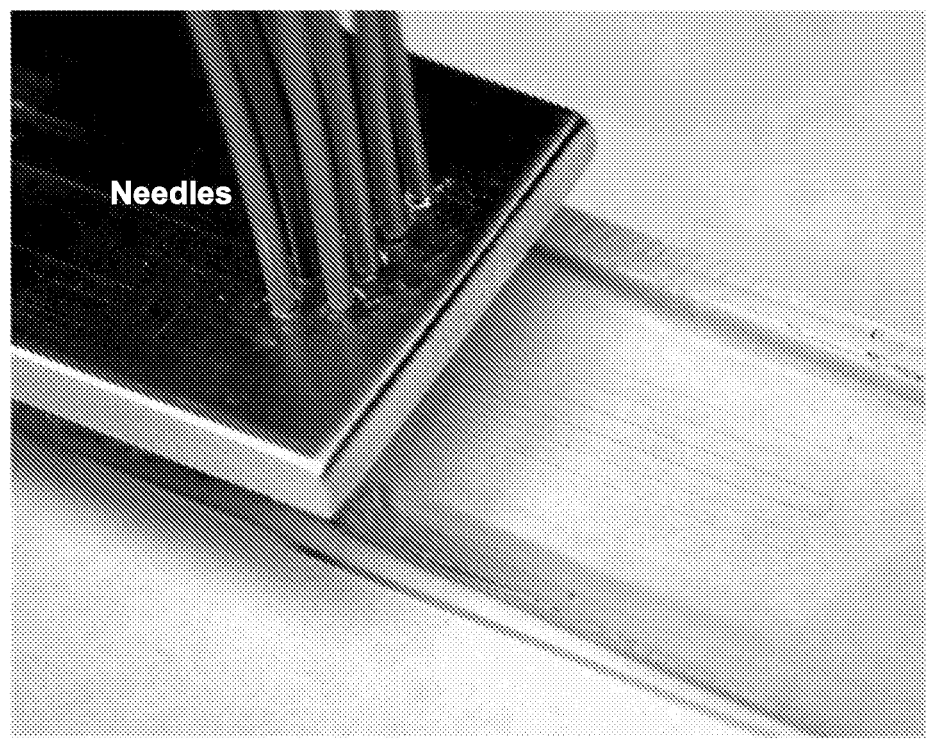

As noted above, multiplexed interconnectivity to microfluidic chips is non-trivial; while it is possible to manually insert a large number of tubing pieces into the necessary ports on a chip, there are limited options for automating this process at this scale, and commercial options for multiplexed repeated connect/disconnect microfluidic interconnects are immature and few and far between (Dolomite offers a custom solution for their own chips; additional engineering would be needed to interface to the PDMS-based devices). As such, one goal with the chip designs is to minimize and simplify interconnectivity to the off-chip world. The prior chips required only 6 (for $^{18}$F-fallypride) or 7 (for $^{68}$Ga-PSMA) off-chip connections total, including inlet, outlet, and valve connections. When envisioning automated use, it is important to consider how to reproducibly fluidically connect and disconnect to a microfluidic device, and how to standardize this interconnectivity between chip designs so that a single automated system can work with multiple device architectures (for various radiochemistries). Additionally, it is critical to minimize the off-chip fluidic path lengths for mid-process steps to avoid the need for excessive reagents or flow times. By employing relatively low pressures throughout the production process (about 15 PSI), the requirements on the chip-to-world interconnect seal are reduced. The interconnect design includes an array of PEEK needles, as shown in FIGS. 22A-22B for example, connected to the rest of the automation apparatus. This needle array is pressed against the RAPID chip in use such that the needles form fluidic connections with laser-drilled ports on the microfluidic chip. In some embodiments, a standardized port layout is used such that there is no need to rearrange the needles for different RAPID chip architectures (i.e., $^{18}$F vs $^{68}$Ga). Burst pressure of the interface is quantified. In addition, connection reliability testing is performed to ensure a minimum lifetime for the needle array (e.g., perform an automated run of 10,000 connect/disconnect cycles and ensure the burst pressure does not decrease). In certain embodiments, RAPID chips are produced and loaded with the necessary resins (or monoliths) in a clean, sterile environment, after which a thin PDMS film is used to seal the top surface. In EXAMPLE 2 above, such a film is employed to seal only the top of the reaction chamber. In some embodiments, however, a larger film is employed to seal the ports as well to prevent contamination in iterations involving automation, so that all RAPID chips are sealed until the PDMS film covering the ports is pierced by the needle array, ensuring device sterility.

After the automated system is constructed, it is validated for both $^{18}$F and $^{68}$Ga radiochemistries using appropriate RAPID chips. For each batch, less than 15 minutes is required to go from the initial concentration step to the final ready-to-use (purified and sterile) tracer product (at least 20 mCi), which is much shorter and has much better efficiency, compared to a complete manual production run shown in EXAMPLE 2 above, which takes about 60 minutes and yields 3 mCi $^{18}$F-fallypride.

In certain embodiments, reproducibility is demonstrated by producing 25 batches of a $^{18}$F tracer (e.g., $^{18}$F-fallypride) and 25 batches of a $^{68}$Ga tracer (e.g., $^{68}$Ga-PSMA), with each batch using a fresh RAPID chip and alternating tracers between each individual batch. Doses collected in vials after this 50-batch run are characterized by using standard analytical methods associated with routine clinical production and validation of each tracer. These include HPLC assays of chemical purity, radiochemical identity and purity, as well as strength. The absence of endotoxins and sterility is also confirmed for each batch, for example, using Limulus amoebocyte lysate [LAL] testing.

According to the invention, the automated RAPID platform is capable of producing multiple, unique doses of ready-to-use PET tracers that are reliably pass all FDA-acceptable release criteria. In addition, software on the NodeMCU allows for remote control and scheduled dose production requests via an online web or smartphone app interface. Interlock features and lead shielding prevent inadvertent exposure to harmful levels of radiation and ensure that used RAPID chips are provided adequate cool-down time prior to disposal.

In certain embodiments, multiplexed fluidic interconnect approach are used. Alternatively, the commercially available chip headers and interconnects (e.g., sold by Dolomite) can also be employed. In certain embodiments, the microcontroller-driven peristaltic pump system are utilized. In other embodiments, a wide range of 3D-printable syringe pumps that may be controlled with the same microcontrollers can be employed. In these embodiments, reagents are loaded in syringes (as opposed to vials) and placed in the appropriate sections of the apparatus. In certain embodiments, the septum-sealed vial approach described above is preferred.

In certain embodiments, in-line pressure and flow sensors are employed to monitor any batch-to-batch variation, which these are easily interfaced to the process controller or temporary debugging equipment. The inline pressure sensors operably check to ensure backpressure is not too high (indicating clogging) or too low (indicating membrane damage). To ensure product sterility, in-line 0.22 μm sterile filters are also employed in the fluidic path between the RAPID device outlet and robotic system for dispensing into sterile vials. These filters can be changed periodically if needed.

According to the invention, the robust microfluidic platforms are capable of high throughput production of custom PET tracers that are immediately ready to use in humans. This platforms employ novel, low cost microfluidic chips that take commercially available reagents and isotope in, and produce purified ready-to-use tracers. By establishing dose-on-demand PET tracer production in a small, automated platform, one enables a paradigm shift in PET tracer production that facilitates molecular imaging for precision medicine.

According to the invention, there are benefits of microfluidics for radiopharmaceuticals. Given the tremendous costs of radiotracer production and development, there has been considerable interest in leveraging microfluidics to increase efficiency in radiosynthesis. Immediate benefits of microfluidic radiosynthesis modules include decreased physical footprint, which in turn reduces laboratory/clinical space requirements for large radiation-shielded environments (so-called "hot cells"). While being fully sufficient for producing clinically meaningful dosages, chip-scale approaches also lend themselves to decreased reaction volume requirements and higher overall reaction concentrations. Accordingly, production times are decreased relative to macro scale production due to increased heat transfer, higher surface-to-volume ratio, and controllable mixing. In turn, radiochemical yield, radiochemical purity, molar activity, and overall production reproducibility are all significantly enhanced. Collectively, these benefits enable a reduction in the initial radioactivity necessary for a successful production, and accordingly, decreased radiation shielding requirements which could, in future instances, eliminate the need for large, costly hot cells altogether. Below we describe a portion of salient features and considerations related to microfluidic radiosynthesis modules.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

Some references, which may include patents, patent applications, and various publications, are cited and discussed in the description of the invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

REFERENCES LIST (1) Ametamey, S. M.; Honer, M.; Schubiger, P. A. *Chem. Rev.* 2008, 108 (5), 1501-1516.

(2) Fortt, R.; Gee, A. *Future Med. Chem.* 2013, 5 (3), 241-244.

(3) Rensch, C.; Jackson, A.; Lindner, S.; Salvamoser, R.; Samper, V.; Riese, S.; Bartenstein, P.; Wängler, C.; Wängler, B. *Molecules* 2013, 18 (12), 7930-7956.

(4) Audrain, H. *Angew. Chemie Int. Ed.* 2007, 46 (11), 1772-1775.

(5) Elvira, K. S.; i Solvas, X. C.; Wootton, R. C. R.; DeMello, A. *J. Nat. Chem.* 2013, 5 (11), 905-915.

(6) Philippe, C.; Pichler, V.; Hacker, M.; Mitterhauser, M.; Wadsak, W. 2018, 5997-6004.

(7) Miller, P. W. *J. Chem. Technol. Biotechnol.* 2009, 84 (3), 309-315.

(8) Chen, S.; Javed, M. R.; Kim, H. -K.; Lei, J.; Lazari, M.; Shah, G. J.; van Dam, R. M.; Keng, P.; Kim, C. -J. "CJ." *Lab Chip* 2014, 14 (5), 902-910.

(9) Arima, V.; Pascali, G.; Lade, O.; Kretschmer, H. R.; Bernsdorf, I.; Hammond, V.; Watts, P.; De Leonardis, F.; Tarn, M. D.; Pamme, N.; Cvetkovic, B. Z.; Dittrich, P. S.; Vasovic, N.; Duane, R.; Jaksic, A.; Zacheo, A.; Zizzari, A.; Marra, L.; Perrone, E.; Salvadori, P. A.; Rinaldi, R. *Lab Chip* 2013, 13 (12), 2328.

(10) Pascali, G.; Nannavecchia, G.; Pitzianti, S.; Salvadori, P. A. *Nucl. Med. Biol.* 2011, 38 (5), 637-644.

(11) Bejot, R.; Elizarov, A. M.; Ball, E.; Zhang, J.; Miraghaie, R.; Kolb, H. C.; Gouverneur, V. *J. Label. Compd. Radiopharm.* 2011, 54 (3), 117-122.

(12) Zeng, D.; Desai, A. V; Ranganathan, D.; Wheeler, T. D.; Kenis, P. J. A.; Reichert, D. E. *Nucl. Med. Biol.* 2013, 40 (1), 42-51.

(13) von Eyben, F. E.; Baumann, G. S.; Baum, R. P. *Clin. Transl. Imaging* 2018, 6 (2), 145-148.

(14) Afshar-Oromieh, A.; Zechmann, C. M.; Malcher, A.; Eder, M.; Eisenhut, M.; Linhart, H. G.; Holland-Letz, T.; Hadaschik, B. A.; Giesel, F. L.; Debus, J.; Haberkorn, U. *Eur. J. Nucl. Med. Mol. Imaging* 2014, 41 (1), 11-20.

(15) Afshar-Oromieh, A.; Haberkorn, U.; Eder, M.; Eisenhut, M.; Zechmann, C. M. *Eur. J. Nucl. Med. Mol. Imaging* 2012, 39 (6), 1085-1086.

(16) Ahmadzadehfar, H.; Eppard, E.; Kürpig, S.; Fimmers, R.; Yordanova, A.; Schlenkhoff, C. D.; Gartner, F.; Rogenhofer, S.; Essler, M. *Oncotarget* 2016, 7 (11), 12477-12488.

(17) Zhang, X.; Liu, F.; Knapp, K. A.; Nickels, M. L.; Manning, H. C.; Bellan, L. M. *Lab Chip* 2018, 18, 1369-1377.

(18) Mueller, D.; Breeman, W. A. P.; Klette, I.; Gottschaldt, M.; Odparlik, A.; Baehre, M.; Tworowska, I.; Schultz, M. K. *Nat. Protoc.* 2016, 11 (6), 1057-1066.

(19) Mueller, D.; Klette, I.; Baum, R. P.; Gottschaldt, M.; Schultz, M. K.; Breeman, W. A. P. 2012.

(20) Mueller, D.; Klette, I.; Baum, R. P.; Gottschaldt, M.; Schultz, M. K.; Breeman, W. A. P. *Bioconjug. Chem.* 2012, 23 (8), 1712-1717.

What is claimed is:

1. A device for synthesizing a radioisotope-labelled target tracer, the device comprising:

(a) a substrate and a microfluidic chip comprising a patterned layer on the substrate or an etched layer on the substrate, and a strong cation exchange (SCX) module, a strong anion exchange (SAX) module, and a passive in-plane mixing and reaction module, wherein the SCX module is configured to cationically concentrate and capture a radioisotope from a radioisotope solution delivered from a radioisotope generator, and release the captured radioisotope from the SCX module;

the SAX module is in fluidic communication with the SCX module and is configured to anionically purify the released radioisotope; and the passive in-plane mixing and reaction module is in fluidic communication with the SAX module and is configured to mix the purified radioisotope and a target precursor and synthesize the radioisotope-labelled target tracer in the passive in-plane mixing and reaction module by performing a labelling reaction;

(b) a heating means positioned proximate to the microfluidic chip for heating the microfluidic chip during the labelling reaction; and (c) a first valve fluidically coupled with the SCX module and the SAX module and a second valve fluidically coupled with the SAX module and the passive in-plane mixing and reaction module, the first valve and the second valve for operably controlling a first transit of various substances among the SCX module, the SAX module, and the passive in-plane mixing and reaction module or a second transit of various mixtures among the SCX module, the SAX module, and the passive in-plane mixing and reaction module, wherein the passive in-plane mixing and reaction module comprises a flow focusing means, a mixing channel and a reaction chamber, wherein the mixing channel comprises a mixing channel entrance and the flow focusing means is disposed at the mixing channel entrance and is configured to flow focus the purified radioisotope and the target precursor onto the mixing channel such that the purified radioisotope and the target precursor mix in the mixing channel and form a mixture for loading into the reaction chamber for performing the labelling reaction in the reaction chamber and wherein the flow focusing means comprises a target precursor inlet, a first radioisotope inlet and a second radioisotope inlet wherein the first radioisotope inlet is configured to enable a first portion of the purified radioisotope to flow into the focusing means in a first flow direction, the second radioisotope inlet is configured to enable a second portion of the purified radioisotope to flow into the focusing means in a second flow direction, the first flow direction facing the second flow direction, and the target precursor inlet is configured to enable the target precursor to be injected into the focusing means in a third flow direction having an angle greater than zero relative to the first flow direction and the second flow direction.

2. The device of claim 1, further comprising one or more pumps fluidically coupled with the first valve or with the second valve or with both for operably controlling the first transit or the second transit or both.

3. The device of claim 1, wherein the SCX module comprises an SCX module inlet, an SCX module outlet, a SCX microchannel disposed between the SCX module inlet and the SCX module outlet and a SCX module trapping mechanism disposed in the SCX module microchannel proximate to the SCX outlet and wherein the SAX module comprises an SAX module inlet, an SAX module outlet, a SAX module microchannel disposed between the SAX module inlet and the SAX module outlet, and a SAX module trapping mechanism disposed in the SAX module microchannel proximate to the SAX module outlet.

4. The device of claim 3, wherein the SCX module microchannel comprises a SCX module microchannel inner wall and the SAX module microchannel comprises a SAX module microchannel inner wall and the SCX module microchannel inner wall is coated with a first inert layer or the SAX module microchannel inner wall is coated with a second inert layer or the SAX module microchannel inner wall is coated with the first inert layer and the SCX module inner wall is coated with the second inert layer.

5. The device of claim 3, wherein the SCX module microchannel has a first length, a first width, and a first height and the SAX module microchannel has a second length, a second width and a second height, wherein the first height and the second height have a range between 1 and 100 μm and wherein the length is greater than the width, or the length is equal to or less than the width.

6. The device of claim 3, wherein the SCX module microchannel comprises a first plurality of parallel chambers or the SAX module microchannel comprises a second plurality of parallel chambers or the SCX module microchannel comprises the first plurality of parallel chambers and the SAX module microchannel comprise the second plurality of parallel chambers.

7. The device of claim 3, wherein the SCX module microchannel comprises no more than a SXC module chamber or the SAX module microchannel comprises a no more than a SAX module single chamber, or the SCX module chamber comprises no more than the SAX module single chamber and the SCX module microchannel comprises no more than the SCX chamber single chamber wherein the SCX module single chamber has a first plurality of sub-inlets and a first plurality of sub-outlets, the first plurality of sub-inlets and the first plurality of sub-outlets to yield a first enhanced packing uniformity and the SAX module single chamber has a second plurality of sub-inlets and a second plurality of sub-outlets, the second plurality of sub-inlets and the second plurality of sub-outlets to yield a second enhanced packing uniformity.

8. The device of claim 3, wherein the SCX module trapping mechanism comprises a first row of pillars, each pillar or the first row of pillars having a first predefined gap or the SAX module trapping mechanism comprises a second row of pillars, each pillar of the second row of pillar having a second predefined gap or the SCX module trapping mechanism comprises the first row of pillars and the SAX module trapping mechanism comprises the second row of pillars.

9. The device of claim 3, wherein the SCX module has a SXC module column comprising a first plurality of microparticles and the SAX module has a SAX column comprising a second plurality of microparticles, the first plurality of microparticles and the second plurality of microparticles for radioactivity concentration or for purification, wherein the SCX module microchannel is configured to enable the first plurality of microparticles to be suspended in a first solution within the SXC module microchannel and the SAX module microchannel is configured to enable the second plurality of microparticles to be suspended in a second solution within the SAX module microchannel.

10. The device of claim 9, wherein the first plurality of microparticles comprises a SCX resin, and the second plurality of microparticles comprises a SAX resin.

11. The device of claim 1, wherein the mixing channel has a zigzag shape.

12. The device of claim 1, wherein the mixing channel has a plurality of obstructions disposed within the mixing channel.

13. The device of claim 1, wherein the heating means comprises a hot plate placed under the substrate.

14. The device of claim 2, wherein the heating means comprises an on-chip resistive heater and an on-chip resistive temperature detector (RTD), the on-chip resistive heater and the RTD configured to enable a closed-loop control of a reaction temperature in a predefined range.

15. The device of claim 14, wherein the on-chip resistive heater comprises a first plurality of metals traces and a first plurality of metal electrodes patterned on the substrate, and the on-chip RTD comprises a second plurality of metal electrodes patterned on the substrate proximate to the plurality of metal traces of the on-chip resistive heater.

16. The device of claim 15, wherein the heating means further comprises a protective layer formed over the first plurality of metal electrodes and the second plurality of metal electrodes.

17. The device of claim 14, wherein the on-chip RTD is configured to measure a temperature and the device further comprises a microcontroller configured to read the temperature measured by the on-chip RTD and control a solid state relay (SSR) to connect and disconnect the on-chip resistive heater from a power supply by using a proportional, integral and differential (PID) library.

18. The device of claim 17, wherein the first valve is configured to operate at a first operation and the second valve is configured to operate at a second operation and the microcontroller is further configured to control the first operation of the first valve, the second operation of the second valve and the one or more pumps so as to control the first transit or the second transit.

19. The device of claim 18, wherein the microcontroller is further configured to control the first valve, the second valve, the one or more pumps, and the heating means via one or more user computer interfaces or via one or more user a mobile device user interfaces, the one or more user computer or the one or more user mobile device interfaces in a wired communication or in a wireless communication and wherein the radioisotope comprises Galium-68 ($^{68}$Ga) or Lutetium-177 ($^{177}$Lu), and the target precursor comprises prostate-specific membrane antigen (PSMA), and wherein the radio-isotope-labelled target tracer is $^{68}$Ga-labelled PSMA or $^{177}$Lu-labelled PSMA.

* * * * *